(12) United States Patent
Yamazaki et al.

(10) Patent No.: US 7,923,012 B2
(45) Date of Patent: Apr. 12, 2011

(54) ANTIBODY AGAINST FIBROBLAST GROWTH FACTOR-23

(75) Inventors: Yuji Yamazaki, Gunma (JP); Takashi Shimada, Gunma (JP); Takeyoshi Yamashita, Gunma (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 10/500,296

(22) PCT Filed: Jan. 6, 2003

(86) PCT No.: PCT/JP03/00017
§ 371 (c)(1),
(2), (4) Date: Jun. 28, 2004

(87) PCT Pub. No.: WO03/057733
PCT Pub. Date: Jul. 17, 2003

(65) Prior Publication Data
US 2005/0048058 A1    Mar. 3, 2005

(30) Foreign Application Priority Data

Dec. 28, 2001   (JP) .................................. 2001-401689
Sep. 6, 2002    (JP) .................................. 2002-262020

(51) Int. Cl.
*A61K 39/395* (2006.01)
(52) U.S. Cl. .................................. 424/145.1; 530/388.24
(58) Field of Classification Search ........................ None
See application file for complete search history.

(56) References Cited

U.S. PATENT DOCUMENTS

| | | | |
|---|---|---|---|
| 5,585,089 A | 12/1996 | Queen et al. | |
| 5,958,879 A | 9/1999 | Kopchick et al. | |
| 6,001,358 A | 12/1999 | Black et al. | |
| 6,617,118 B2 | 9/2003 | Roffler et al. | |
| 7,094,551 B2 | 8/2006 | Zahradnik et al. | |
| 7,223,563 B2 | 5/2007 | Econs et al. | |
| 7,314,618 B2 | 1/2008 | Econs et al. | |
| 2002/0156001 A1* | 10/2002 | Econs et al. ............... | 514/12 |
| 2004/0082506 A1* | 4/2004 | Yamashita et al. ............ | 514/12 |
| 2004/0171825 A1 | 9/2004 | Bougueleret et al. | |
| 2006/0160181 A1 | 7/2006 | Luethy et al. | |
| 2009/0110677 A1 | 4/2009 | Yamashita et al. | |
| 2009/0148461 A1 | 6/2009 | Yamazaki et al. | |

FOREIGN PATENT DOCUMENTS

| | | |
|---|---|---|
| CA | 2418215 | 1/2002 |
| CN | 1446227 A | 10/2003 |
| EP | 120694 | 10/1984 |
| EP | 125023 | 11/1984 |
| EP | 0314161 A1 | 10/1988 |
| EP | 1466925 A1 | 10/2004 |
| GB | 2188638 A | 10/1987 |
| JP | S-61-178926 | 11/1986 |
| JP | H-02-117920 | 2/1990 |
| WO | WO 99/60017 | 11/1999 |
| WO | WO 00/10383 | 3/2000 |
| WO | WO 00/60085 A1 | 10/2000 |
| WO | WO 00/73454 A1 | 12/2000 |
| WO | WO 01/66595 | 3/2001 |
| WO | WO 01/66596 | 3/2001 |
| WO | WO 01/40466 A2 | 6/2001 |
| WO | WO 01/42451 A2 | 6/2001 |
| WO | WO 0149740 A1 * | 7/2001 |
| WO | WO 01/60850 A1 | 8/2001 |
| WO | WO 01/61007 * | 8/2001 |
| WO | WO 02/08271 A1 | 1/2002 |
| WO | WO 02/14504 * | 2/2002 |
| WO | WO 02/76467 | 3/2002 |
| WO | WO 02/088358 A2 | 11/2002 |
| WO | WO 02/043478 | 5/2004 |
| WO | WO 2006/078072 A1 | 7/2006 |
| WO | WO 2008/092019 A1 | 7/2008 |

OTHER PUBLICATIONS

Campbell, A.M., Monoclonal antibody technology, Elsevier Science Publishers, Inc., 1984, pp. 1-32.*
Wen et al., Proc. Natl. Acad. Sci. USA 98 (8): 4622-27 (2001).*
Superti-Furga, et al., American Journal of Medical Genetics (Semin. Med. Genet.) 106: 282-93 (2001).*
Lorenz-Depiereux et al., Eur. J. Human Genetics 9 (Supplement 1) pp. P0772 (2001).* Yu et al., Endocrinology. Nov. 2005;146(11):4647-56.*
Bost et al., Immunol. Invest. 1988; 17:577-586.*
Mohammadi et al., Cytokine Growth Factor Rev. Apr. 2005;16(2):107-37.*
International Search Report.
Takashi Shimada et al., "Cloning and characterization of FGF23 as a causative factor of tumor-induced osteomalacia", Proc. Natl. Acad. Sci., USA, May 22, 2001, vol. 98, Issue 11, pp. 6500-6505.
Yuji Yamazaki et al., "Increased circulatory level of biologically active full-length FGF-23 in patients with hypophosphatemic rickets/osteomalacia", The Journal of Clinical Endocrinology & Metabolism, (Nov. 2002), vol. 87, No. 11, pp. 4957-4966.

(Continued)

Primary Examiner — Zachary Skelding
(74) Attorney, Agent, or Firm — Stephen A. Bent; Foley & Lardner LLP

(57) ABSTRACT

The purpose of the present invention is to provide an antibody against fibroblast growth factor 23. The antibody is obtained by immunizing an animal with a polypeptide which comprises an amino acid sequence represented by SEQ ID NO: 1, or an amino acid sequence derived from the amino acid sequence represented by SEQ ID NO: 1 by deletion, substitution, or addition of 1 or several amino acids, and has fibroblast growth factor-23 activity and activity to control phosphate metabolism or vitamin D metabolism, and is shown by the following (a), (b), or (c):

(a) an antibody, which recognizes an amino acid sequence between the $180^{th}$ and the $194^{th}$, or the $237^{th}$ and the $251^{st}$ amino acid residues represented by SEQ ID NO: 1;
(b) an antibody, which is produced by a hybridoma whose accession number is FERM BP-7838, FERM BP-7839, FERM BP-7840, or FERM BP-8268; or
(c) an antibody, which is competitive with the antibody produced by the hybridoma whose accession number is FERM BP-7838, FERM BP-7839, FERM BP-7840, or FERM BP-8268 upon binding with the polypeptide comprising the amino acid sequence represented by SEQ ID NO: 1.

3 Claims, 42 Drawing Sheets
(3 of 42 Drawing Sheet(s) Filed in Color)

OTHER PUBLICATIONS

Yuji Yamazaki et al, "Detection of Circulating FGF-23 by Monoclonal Antibodies Against Recombinant Human FGF-23", Journal of the American Society of Nephrology, (Sep. 2002), vol. 13, (Program and Abstract Issue), p. 499A.

Takashi Shimada et al, "FGF-23 Is a Novel Humoral Factor Regulating Vitamin D Metabolism", Journal of the American Society of Nephrology, (Sep. 2002), vol. 13, (Program & Abstract Issue), p. 28A.

Takashi Shimada et al., "Mutant FGF-23 responsible for autosomal dominant hypophosphatemic rickets is resistant to proteolytic cleavage and causes hypophosphatemia in vivo", Endocrinology, (Aug. 2002), vol. 143, No. 8 pp. 3179-3182.

Yuji Yamazaki et al, "Development of the ELISA System Using Monoclonal Antibodies against FGF-23 and Demonstration of Increased Plasma Concentration of FGF-23 in Tumor-Induced Osteomalacia", ENDO, 2002, The Endocrine Society's 84th Annual Meeting, Program & Abstract, p. 66.

Y. Yamazaki et al., "FGF-23 Protein is Present in Normal Plasma and Is increased in Patients with Tumor-Induced Osteomalacia", (Sep. 2002), The Journal of Bone and Mineral Research, vol. 17, suppl. 1, p. 159.

Kenneth E. White et al., "Autosomal-dominant hypophosphatemic rickets (ADHR) mutation stabilize FGF-23", Kidney International, vol. 60 (2001), pp. 2079-2086.

Non-Final Office Action for U.S. Appl. No. 10/344,339 dated Jan. 18, 2008.

Advisory Action for U.S. Appl. No. 10/344,339 dated Dec. 7, 2007.

Final Office Action for U.S. Appl. No. 10/344,339 dated Jun. 22, 2007.

Non-Final Office Action for U.S. Appl. No. 10/344,339 dated Sep. 27, 2006.

Notice of Allowance for Korean Patent Application No. 10-2003-7001931 dated Nov. 26, 2008—international, counterpart to U.S. Appl. No. 10/344,339.

Office Action for Canadian Patent Application No. 2,418,802 dated Feb. 13, 2009—international, counterpart to U.S. Appl. No. 10/344,339.

Supplementary European Search Report of European Patent Application No. EP 01 95 8379 dated May 27, 2005—international, counterpart to U.S. Appl. No. 10/344,339.

International Search Report of PCT Patent Application No. PCT/JP2008/052918 dated Mar. 13, 2008—international, counterpart to U.S. Appl. No. 12/030,593.

Aono et al., "The improving effect of anti FGF23 neutralizing antibody on hypophosphatemia and rickets of Hyp mice", The Japanese Society for Bone and Mineral Research (JSBMR), Annual Meeting of the JSBMR, 22nd Program, Aug. 2004, vol. 22, pp. 137.

Ando, et al., Tan-Clone-Kotai-Jikken-Manual ("Experimental Manual for Monoclonal Antibody") (written by and published by Kodansha Scientific, Ltd., Tokyo, Japan (1991).

Antibody Engineering, A Practical Approach, IRL Press, 1996.

Antibody Engineering, A Practical Guide, W.H. Freeman and Company, 1992.

Aschinberg et al., "Vitamin D-resistant rickets associated with epidermal nevus syndrome: Demonstration of a phosphaturic substance in the dermal lesions," The Journal of Pediatrics, vol. 91, No. 1, Jul. 1997, pp. 56-60, The C.V. Mosby Company, St. Louis, Mo.

Baker and Worthley, "The Essentials of Calcium, Magnesium and Phosphate Metabolism: Part II. Disorders," Critical Care & Resuscitation., 2000, vol. 4, pp. 307-315.

Better et al., "Escherichia coli Secretion of an Active Chimeric Antibody Fragment," Science, May 20, 1998 (nti), vol. 240, pp. 1041-1043.

Benjannet et al., "α1 -Antitrypsin Portland Inhibits Processing of Precursors Mediated by Proprotein Convertases Primarily within the constitutive Secretory Pathway," The Journal of Biological Chemistry, vol. 272, No. 42, Oct. 17, 1997, pp. 2610-2618, The American Society for Biochemistry and Molecular Biology, Inc.

Briand et al., "Application and limitations of the multiple antigen peptide (MAP) system in the production and evaluation of anti-peptide and anti-protein antibodies", Journal of Immunnological Methods, vol. 156, No. 2, 1992, pp. 255-265, Elsevier Science Publishers B.V.

Bruggemann, et al., "The Immunogenicity of Chimeric Antibodies", J. Exp. Med., Dec. 1989, vol. 170, No. 6, pp. 2153-2157.

Cai et al., "Brief Report: Inhibition of Renal Phosphate Transport by a Tumor Product in a Patient with Oncogenic Osteomalcia", The New England Journal of Medicine, vol. 330, No. 23, Jun. 9, 1994, pp. 1645-1649, The Massachusetts Medical Society.

Carter, et al., "High Level Escherichia coli Expression and Production of a Bivalent Humanized Antibody Fragment," Bio/Technology, 1992, vol. 10, pp. 163-167.

Delves, P. J., "Antibody Production Essential Techniques", Monoclonal Antibodies, Ed. Shepherd and Dean, Oxford University Press, 2000.

Drezner, "PHEX gene and hypophosphatemia", Kidney International, vol. 57, No. 1, Jan. 2000, pp. 9-18, The International Society of Nephrology.

Ecarot et al., "Defective Bone Formation by Hyp Mouse Bone cells Transplanted into Normal Mice: Evidence in Favor of an Intrinsic Osteoblast Defect", Journal of Bone and Mineral Research, vol. 7, No. 2, Feb. 1992, pp. 215-220, Mary Ann Liebert, Inc.

Econs et al., "Autosomal Dominant Hypophosphatemic Rickets Is Linked to Chromosome 12p13", The Journal of Clinical Investigation, vol. 100, No. 11, Dec. 1, 1997, pp. 2653-2657, The Rockefeller University Press.

Econs et al., "Tumor-Induced Osteomalacia- Unveiling a New Hormone", The New England Journal of Medicine, vol. 330, No. 23, Jun. 9, 1994, pp. 1679-1681, The Massachusetts Medical Society.

Econs, "New Insights Into The Pathogenesis Of Inherited Phosphate Wasting Disorders" Bone, vol. 25, No. 1, Jul. 1999, pp. 131-135 Pergamon Press, Oxford, GB.

Fishwild, et al., "High-avidity Human IgGκ Monoclonal Antibodies from a Novel Strain of Minilocus Transgenic Mice," Nat Biotechnol., Jul. 1996, vol. 14, No. 7, pp. 845-851.

Fukagawa, et al., "FGF23: its Role in Renal Bone Disease", Pediat. Nephrol, 2006, vol. 21, pp. 1802-1806.

Fukumoto et al., "Diagnostic Utility of Magnetic Resonance Imaging Skeletal Survey in a Patient With Oncogenic Osteomalacia", Bone, vol. 25, No. 3, Sep. 1999, pp. 375-377, Elsevier.

Goding, J. W., Monoclonal Antibodies: Principles and Practice, Academic Press, 1993 and 1995.

Gupta, et al., "FGF-23 is Elevated by Chronic Hyperphosphatemia," J. Clin. Endocrinol.& Metab., 2004. vol. 89, No. 9, pp. 4489-4492.

Han et al., "Epinephrine translocates GLUT-4 but inhibits insulin-stimulated glucose transport in rat muscle", American Journal of Physiology, vol. 274, No. 4, Apr. 1998, p. E700-7, The American Physiological Society.

Imel, et al., "FGF23 Concentrations Vary with Disease Status in Autosomal Dominant Hypophosphatemic Rickets," J. of Bone and Mineral Research, 2007, vol. 22, pp. 520-526.

Ishida & Lonberg, IBC's 11th Antibody Engineering, Abstract 2000.

Jonsson, et al., "Fibroblast Growth Factor 23 in Oncogenic Osteomalacia and X-Linked Hypophosphatemia," N. Engl. J. Med., Apr. 24, 2003, vol. 348, No. 17, pp. 1656-1663.

Karlsson, et al., "Kinetic Analysis of Monoclonal Antibody-Antigen Interactions with a New Biosensor Based Analytical System," Journal of Immunological Methods, 1991, vol. 145, pp. 229-240.

Kearney, et al., "A New Mouce Myeloma Cell Line that has Lost Immunoglobulin Expression but Permits the Construction of Antibody-Secreting Hybrid Cell Lines", J. Immunology, Sep. 1979, vol. 123, No. 3, pp. 1548-1550.

Kessler et al., "A Modified Procedure For The Rapid Preparrtion Of Efficiently Transporin Vesicles From Small Intestinal Brush Border Membranes", Biochimica et Biophysica Acta, vol. 506, No. 1, Jan. 4, 1978, pp. 136-155, Elsevier/North-Holland Biomedical Press.

King, D.J., Applications and Engineering of Monoclonal Antibodies, T. J. International Ltd, 1998.

Kitamura, et al., "A B Cell-deficient Mouse by Targeted Distribution of the Membrane Exon of the Immunoglobulin μ Chain Gene," Nature, 1991, vol. 350, No. 4, pp. 423-426.

Kohler, et al., "Derivation of Specific Antibody-producing Tissue Culture and Tumor Lines by Cell Fusion", *European J. Immunology*, 1966, vol. 6, pp. 511-519.

Lah, et al., "Phage Surface Presentation and Secretion of Antibody Fragments using an Adaptable Phagemid Vector," *Human Antibodies & Hybridomas*, 1994, vol. 5, Nos. 1 and 2, pp. 48-56.

Lajeunesse et al., "Direct demonstration of a humorally-mediated inhibition of renal phosphate transport in the *Hyp* mouse", *Kidney International*, vol. 50, No. 5, Nov. 1996, pp. 1531-1538, The International Society of Nephrology.

Larsson, et al., "Circulating Concentration of FGF-23 Increases as Renal Function Declines in Patients with Chronic Kidney Disease, but does not Change in Response to Variation in Phosphate Intake in Healthy Voluneers," *Kidney International*, 2003, vol. 64, pp. 2272-2279.

Lau et al., "Evidence for a Humoral Phosphaturic Factor in Oncogenic Hypophospatemic Osteomalacia", *Clinical Research*, vol. 27, No. 2, Apr. 1979, p. 421A.

Lorenz-Depiereux et al., "Autosomal Dominant Hypophosphatemic Rickets (ADHR) Is Caused By Mutations in a Gene Encoding A Novel Member of the Fibroblast Growth Factor Family(FGF-21)" *American Journal of Human Genetics*, vol. 67, No. 4, suppl. 2, Oct. 2000, p. 12.

Lorenz-Depiereux, et al., "DMP1 Mutations in Autosomal Recessive Hypophosphatemia Implicate a Bone Matrix Protein in the Regulation of Phosphate Homeostasis," *Nature Genetics*, Nov. 2006, vol. 38, No. 11, pp. 1248-1250.

Lu et al., "Chemically Unambiguous Peptide Immunogen: Preparation, Orientation and Antigenicity of Purified Peptide Conjugated to the Multiple Antigen Peptide System", *Molecular Immunology*, vol. 28, No. 6, Jun. 1991, pp. 623-630, Pergamon Press, Great Britain.

Mark, et al., "Site-specific Mutagenesis of the Human Fibroblast Interferon Gene", *Proc Natl Acad Sci U.S.A.*, Sep. 1984, vol. 81, No. 18, pp. 5662-5666.

Meyer et al., "Parabiosis Suggests a Humoral Factor Is Involved inX-Linked Hypophosphatemia in Mice", *Journal of Bone and Mineral Research*, vol. 4, No. 4, Aug. 1989, pp. 493-500, Mary Ann Leibert, Inc.

Miyauchi et al, Hemangiopericytoma-Induced Osteomalacia: Tumor Transplantation in Nude Mice Causes Hypophosphatemia and Tumor Extracts Inhibit Renal 25-Hydroxyvitamin D 1-Hydroxylase Activity', *Journal of Clinical Endocrinology and Metabolism*, vol. 67, No. 1, Jul. 1988, pp. 46-53, The Endocrine Society.

NCBI GenBank Accession No. NP_065689 (Mar. 25, 2007).

NCBI GenBank Accession No. NM_020638 (Mar. 25, 2007).

NCBI GenBank Accession No. AY566236 (Mar. 16, 2004).

Nelson et al., "Oncogenic osteomalacia: is there a new phoshate regulating hormone?", *Clinical Endocrinology*, vol. 47, No. 6, Dec. 1997, pp. 635-642, Blackwell Science Ltd.

Nykjaer et al., "An Endocytic Pathway Essential for Renal Uptake and Activation of the Steroid 25-(OH) Vitamin $D_3$", *Cell*, vol. 96, No. 4, Feb. 19, 1999, pp. 507-515,Cell Press.

Ornitz, et al., "Fibroblast Growth Factors," *Genome Biology*, 2001, vol. 2, No. 3, pp. 3005.1-3005.12.

Popovtzer et al., "Tumor-Induced Hypophosphatemic Osteomalacia (TUO): Evidence for a Phosphaturic Cyclic AMP-Independent Action of Tumor Extract", *Clinical Research*, vol. 29, No. 2, Apr. 1981, p. 418A.

Posnett et al., "A Novel Method for Producing Anti-peptide Antibodies", *The Journal of Biological Chemistry*, vol. 263, No. 4, Feb. 5, 1998, pp. 1719-1725, The American Society for Biochemistry and Molecular Biology, Inc.

Preissner, et al., "Evaluation of the Immutopics Human FGF-23 (C-term) Elisa Kit", *Clinical Chemistry*, vol. 52, No. 6, Suppl. S, Jun. 2006, p. A174.

Reiter, et al., "Engineering Interchain Disulfide Bonds into Conserved Framework Regions of Fv Fragments: Improved Biochemical Characteristics of Recombinant Immunotoxins Containing Disulfide-stabilized Fv", *Protein Engineering*, 1994, vol. 7, No. 5, pp. 697-704.

Riechmann, et al., "Reshaping Human Antibodies for Therapy", *Nature*, Mar. 1988, vol. 332, No. 6162, pp. 323-327.

Riminucci, et al., "FGF-23 in Fibrous Dysplasia of Bone and its Relationship to Renal Phosphate Wasting," *J. Clin. Invest.*, 2003, vol. 112, No. 5, pp. 683-692.

Rowe et al., "Candidate 56 and 58 kDa Protein(s) Responsible for Mediating the Renal Defects in Oncogenic Hypophosphatemic Osteomalacia", *Bone*, vol. 18, No. 2, Feb. 1996, pp. 159-169, Elsevier.

Rowe et al., "MEPE, a New Gene Expressed in Bone Marrow and Tumors Causing Osteomalacia", *Genomics*, vol. 67, No. 1, Jul. 1, 2000, pp. 54-68, Academic Press.

Shibata et al., "Monoclonal Antibodies Against Recombinant Human FGF-23", J. Am. Soc. Nephrol., Sep. 2002, vol. 13, p. 499A (SU-P0151).

Shimada, T. "FGF23 and Phosphorus metabolism", *The Japanese Society for Bone and Mineral Research (JSBMR)*, Annual Meeting of the JSBMR, $23^{rd}$ Program, Jun. 20, 2005, vol. 23, pp. 121.

Shinichi Aizawa, "Biotechnology Manual Series 8, Gene Targeting," Yodosha, 1995.

Shirahata et al., "E1A and *ras* Oncogenes Synergistically Enhance Recombiant Protei Production under Control of the Cytomegalovirus Promoter in BHK-21 Cells", *Biosci. Biotech. Biochem.*, vol. 59, No. 2, Feb. 1995, pp. 345-347, Japan Society For Bioscience, Biotechnology, and Agrochemistry.

Shulman, et al., "A Better Cell Line for Making Hybridomas Secreting Specific Antibodies", *Nature*, Nov. 1978, vol. 276, No. 5685, pp. 269-270.

Strom et al., "*Pex* gene deletions in Gy and Hyp mice provide mouse models for X-linked hypophosphatemia", *Human Molecular Genetics*, vol. 6, No. 2, Feb. 1997, pp. 165-171, The Oxford University Press.

Sunaga, et al., "Efficient Removal of *lox*P-Flanked DNA Sequences in a Gene-Targeted Locus by Transient Expression of Cre Recombinanse in Fertilized Eggs," *Molecular Reproduction and Development*, 1997, vol. 46, pp. 109-113.

Tatsumi et al., "Identification of Three Isoforms for the $NA^+$-dependent Phosphate Cotransporter (NaPi-2) in Rat Kidney", *The Journal of Biological Chemisty*, vol. 273, No. 44, Oct. 30, 1998, pp. 28568-28575, The Society for Biochemistry and Molecular Biology, Inc.

Tomizuka, et al., "Double Trans-Chromosomic Mice: Maintenance Of Two Individual Human Chromosome Fragments Containing Ig Heavy And Antibodies", *Proc Natl Acad Sci U.S.A.*, 2000, vol. 97, No. 2, pp. 722-727.

Urakawa, et al., "Klotho Converts Canonical FGF Receptor into a Specific Receptor for FGF23," *Nature*, Dec. 2006, vol. 444, pp. 770-774.

Van Kroonenbergh, et al., "Human Immunological Response to Mouse Monoclonal Antibodies in the Treatment or Diagnosis of Malignant Diseases," *Nuclear Medicine Communications.*, 1988, vol. 9, pp. 919-930.

White, et al., "Autosomal Dominant Hypophosphataemic Rickets is Associated with Mutations in FGF23", *Nature Genetics*, Nov. 2000, vol. 26, pp. 345-348.

White et al., "Molecular cloning of a novel human UDP-GalNAc: polypeptide N-acetylgalactosaminyltransferase, GalNAc-T8, and analysis as a candidate autosomal dominant hypophosphatemic rickets (ADHR) gene", Gene, Elsevier Biomedical Press, Amsterdam NL, vol. 246, No. 1-2, Apr. 2000, pp. 347-356.

Wilkins et al., "Oncogenic Osteomalacia: Evidence for a Humoral Phosphaturic Factor", *Journal of Clinical Endocrinology and Metabolism*, vol. 80, No. 5, Oct. 22, 2000, pp. 1628-1634, The Endocrine Society.

Wright, et al., "High Level Expression of Active Human Alpha-1-Antitrypsin in the Milk of Transgenic Sheep", *Bio/Technology*, Sep. 1991, vol. 9, No. 9, pp. 830-834.

Yamamoto, et al., "The Role of Fibroblast Growth Factor 23 in Hypophosphatemia and Abnormal Regulation of Vitamin D Metabolism in Patients with McCune-Albright Syndrome," *J. Bone Miner. Metab.*, 2005, vol. 23, pp. 231-237.

Yamashita, et al., "Identification of a Novel Fibroblast Growth Factor, FGF-23, Preferentially Expressed in the Ventrolateral Thalamic Nucleus of the Brain," *Biochemical and Biphysical Research Communications*, 2000, vol. 277, pp. 494-498.

Yamazaki, et al., "Anti-FGF23 neutralizing antibodies show the physiological role and structural features of FGF23", *Journal of Bone and Mineral Research,* vol. 23, No. 9, Sep. 2008, pp. 1509-1518.

Yelton, et al., "Fusion of Mouse Myeloma and Spleen Cells", *Current Topics in Microbiology and Immunology,* 1978, vol. 81, pp. 1-7.

Japanese Office Action 2003-5580417 dated Aug. 20, 2009.

Yukihiro Hasegawa et al., "Vitamin D-Resistant Hypophosphatemic Rickets", The Bone, vol. 15, No. 6, Nov. 2001, pp. 1-9.

Ann E. Bowe et al., "FGF-23 Inhibits Renal Tubular Phosphate Transport and Is a PHEX Substrate", Biochemical and Biophysical Research Communications 284, 977-981 (2001).

Supplementary European Search Report EP 08 71 1707 dated Feb. 9, 2010.

Japanese Office Action Application No. JP 2003-558047 dated Jan. 26, 2010.

Takashi Shimada et al., "Possible Roles of Fibroblast Growth Factor 23 in Developing X-Linked Hypophosphatemia", Clin. Pediatr. Endocrinol. 2005; 14(Suppl23) 33-37.

Satoshi Toyoshima, "Experiment Techniques II", Hirokawa Publishing Co., 1995, first edition, pp. 110-113.

Non-Final Office Action U.S. Appl. No. 12/030,593 dated Apr. 6, 2010.

Marc Drezner, Reviews in Endocrine & Metabolic Disorders 2001;2: 175-186.

Razzaque et al., Nephrol Dial Transplant, Oct. 2005; 20(10):2032-2035.

Inaba et al., Osteoporos Int. Oct. 2006; 17(10):1506-1513.

Vajdos et al., J. Mol. Biol. Jul. 5, 2002; 320(2):415-428.

Webster's New World Dictionary, Third College Edition, 1988, pp. 1067-1068.

Kobayashi et al., Eur J. Endocrinol. Jan. 2006;154(1)93-99.

First Office Action Chinese Application No. 200810086683.1 dated Mar. 8, 2010.

* cited by examiner

Fig. 7
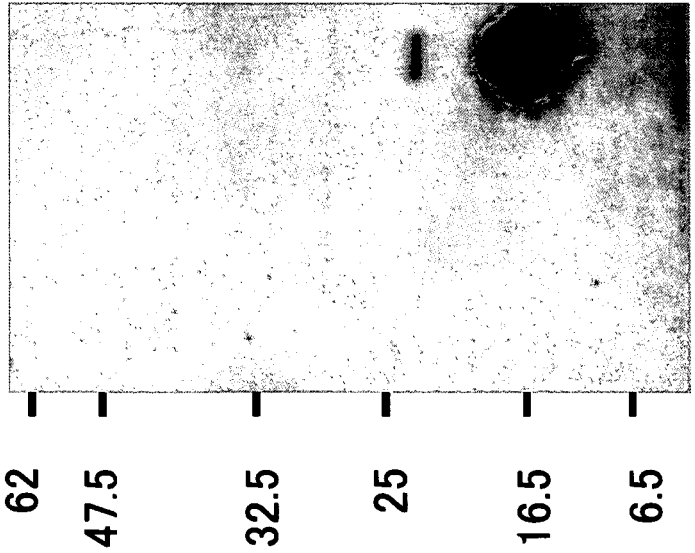

| Group composition | Substance administered | Number of mice | Phosphate (mg/dL) | Calcium (mg/dL) | 1,25(OH)$_2$D (pg/mL) |
|---|---|---|---|---|---|
| Group 1: | PBS | 4 | 8.95 +/- 0.31 | 9.41 +/- 0.20 | 118.1 +/- 8.1 |
| Group 2: | 1D6A | 4 | 6.65 +/- 0.47 * | 9.50 +/- 0.17 | 84.0 +/- 2.6 * |
| Group 3: | 2C3B | 4 | 10.73 +/- 1.22 | 9.74 +/- 0.14 | 192.5 +/- 3.9 * |
| Group 4: | 3C1E | 4 | 11.76 +/- 0.42 * | 9.49 +/- 0.04 | 78.5 +/- 2.2 * |
| Group 5: | Anti-TPO antibody | 4 | 8.93 +/- 0.41 | 9.41 +/- 0.08 | 147.9 +/- 3.8 * |

Fig. 23

| | Age | Gender | FGF-23(ng/L) | Mutation in PHEX gene |
|---|---|---|---|---|
| Case 1 | 3 months old | man | 111.3 | 2071-1 g→a (Intron20) |
| | 1 year old | | 380.3 | |
| Case 2 | 38 years old | woman | 39.0 | 2071-1 g→a (Intron20) |
| Case 3 | 5 years old | woman | 55.7 | 849+1 g→a (Intron 7) |
| | 13 years old | | 68.6 | |
| Case 4 | 15 years old | woman | 115.0 | 2071-2 a→g (Intron20) |
| Case 5 | 18 years old | woman | 107.6 | 2071-2 a→g (Intron20) |
| Case 6 | 67 years old | woman | 96.5 | Q189X (Exon 5) |

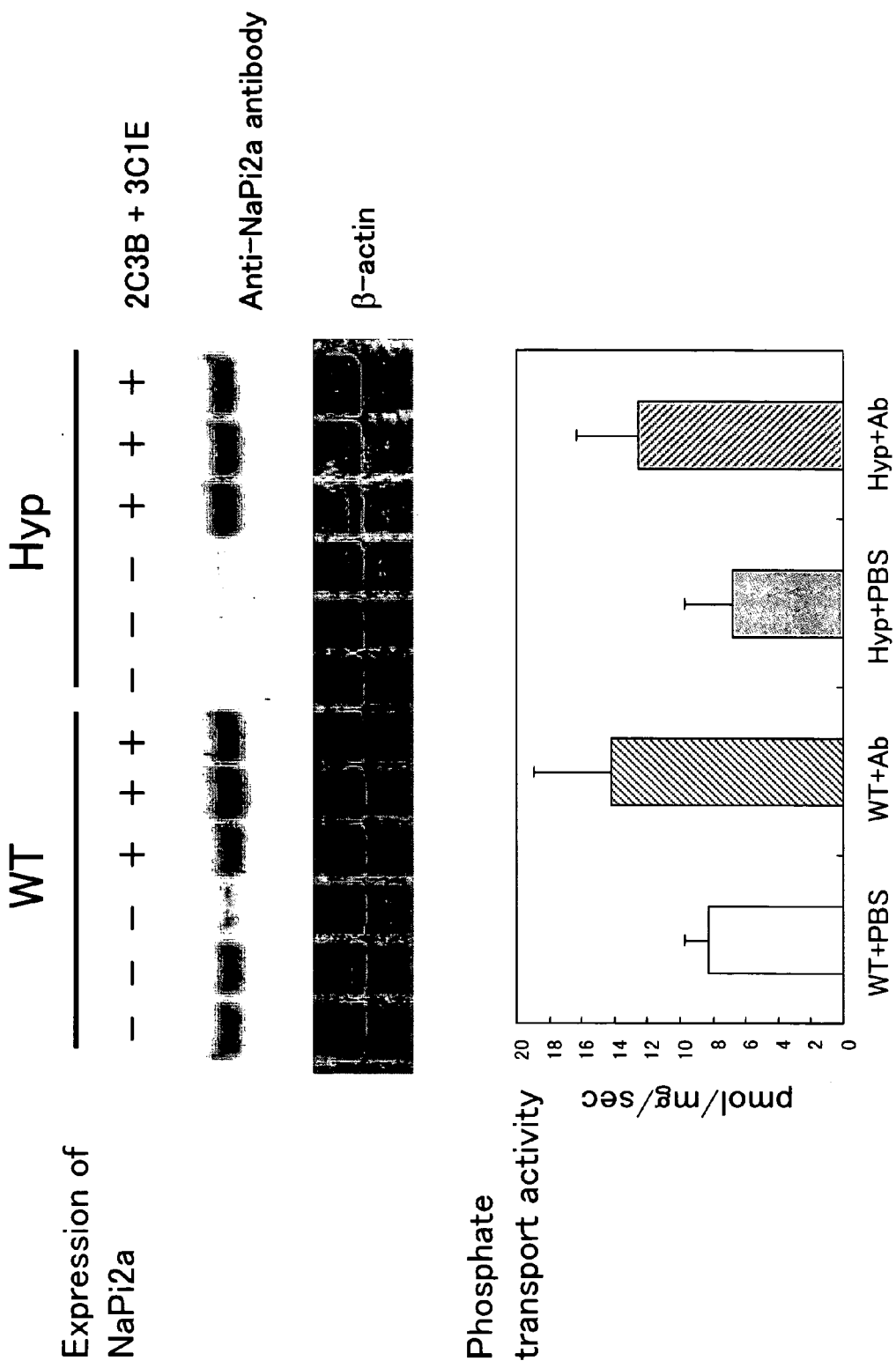

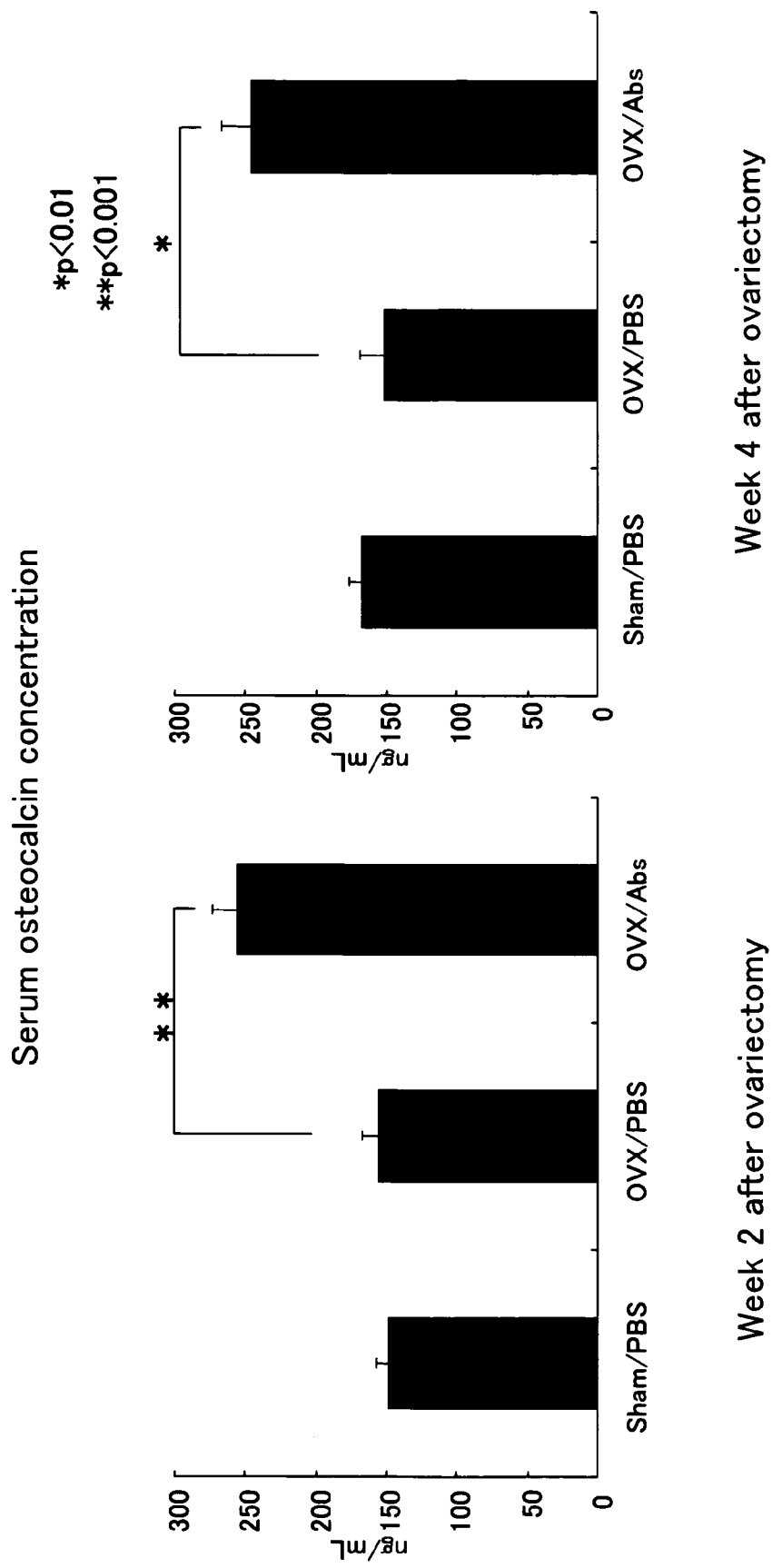

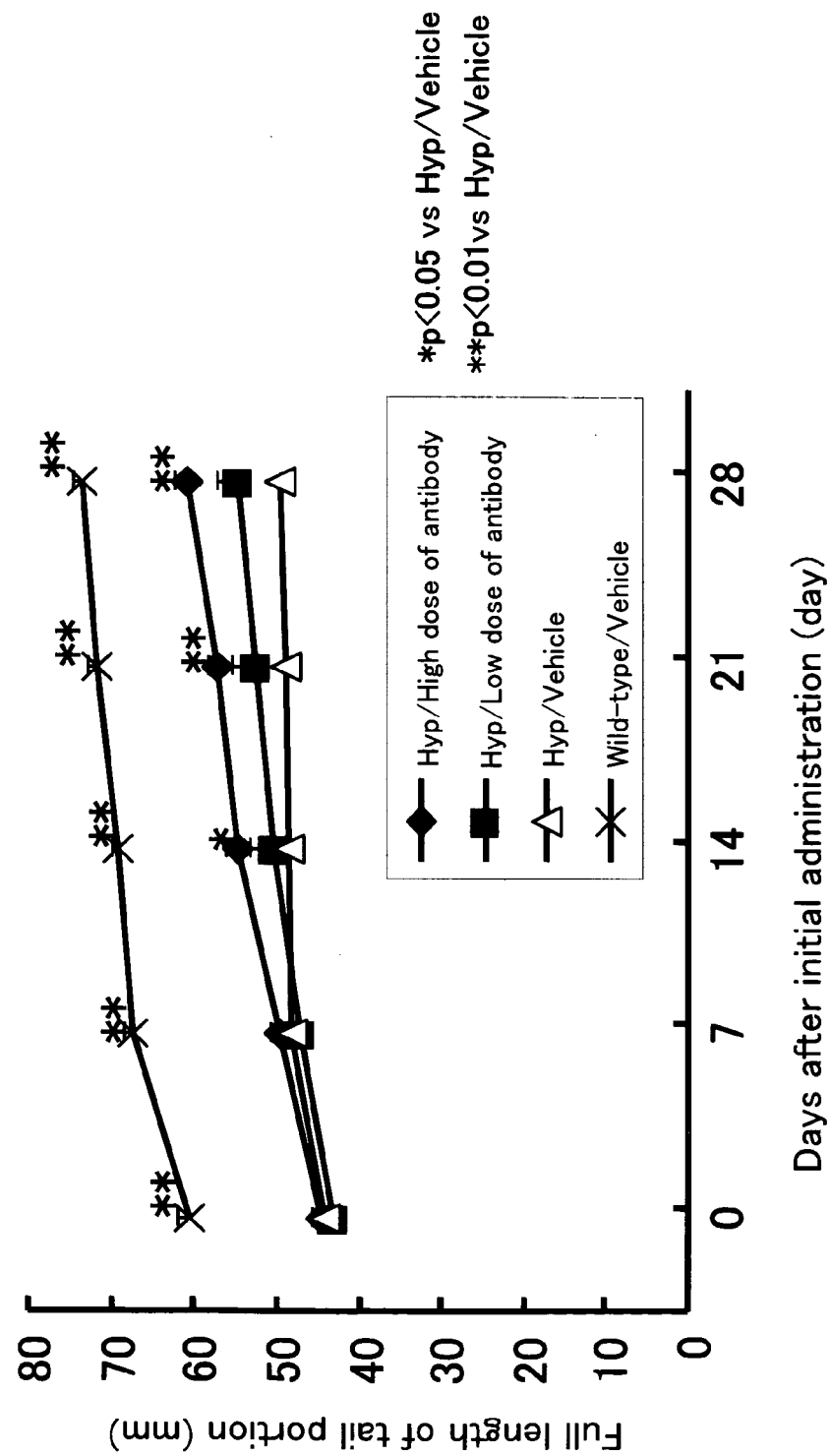

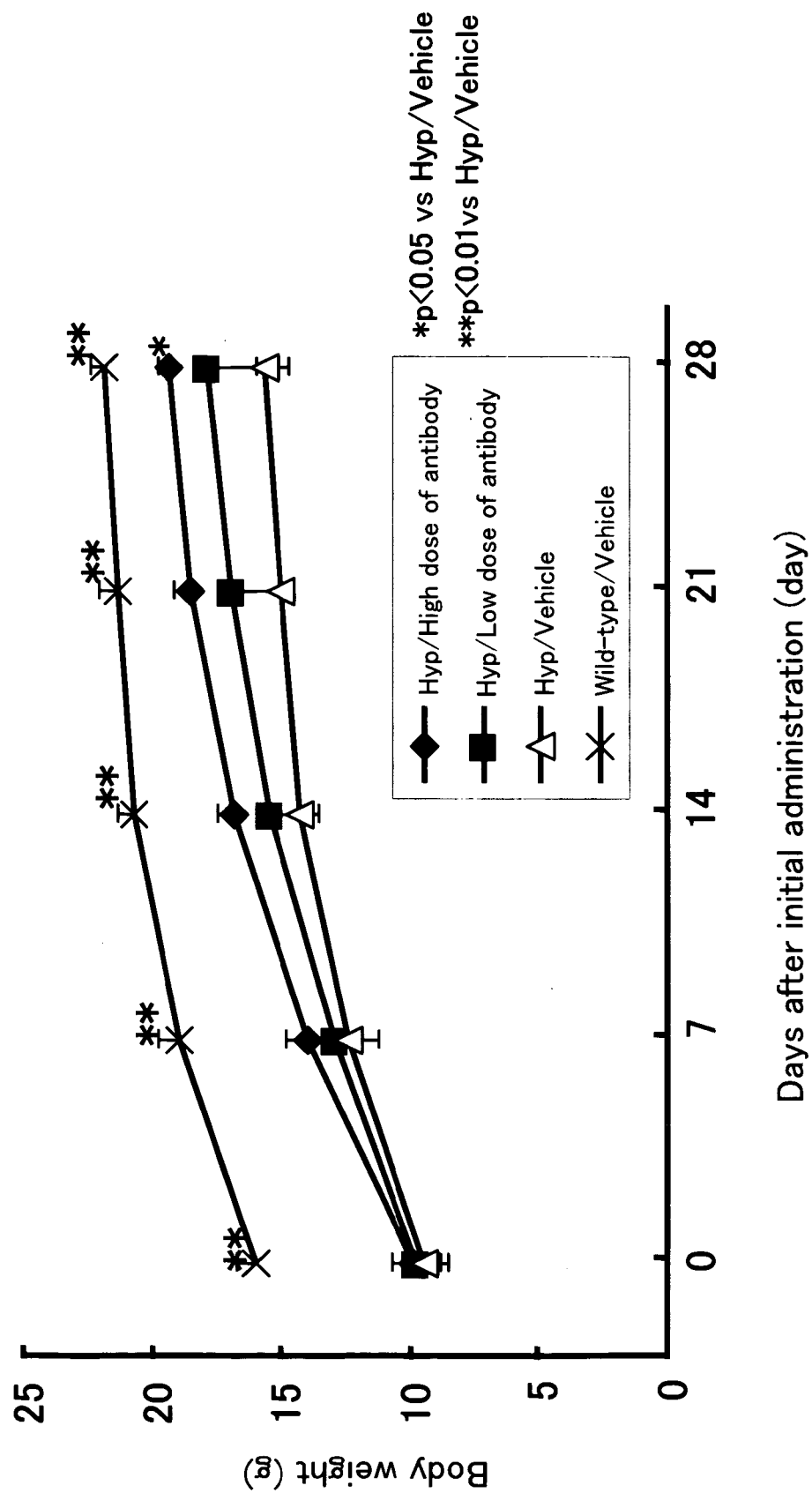

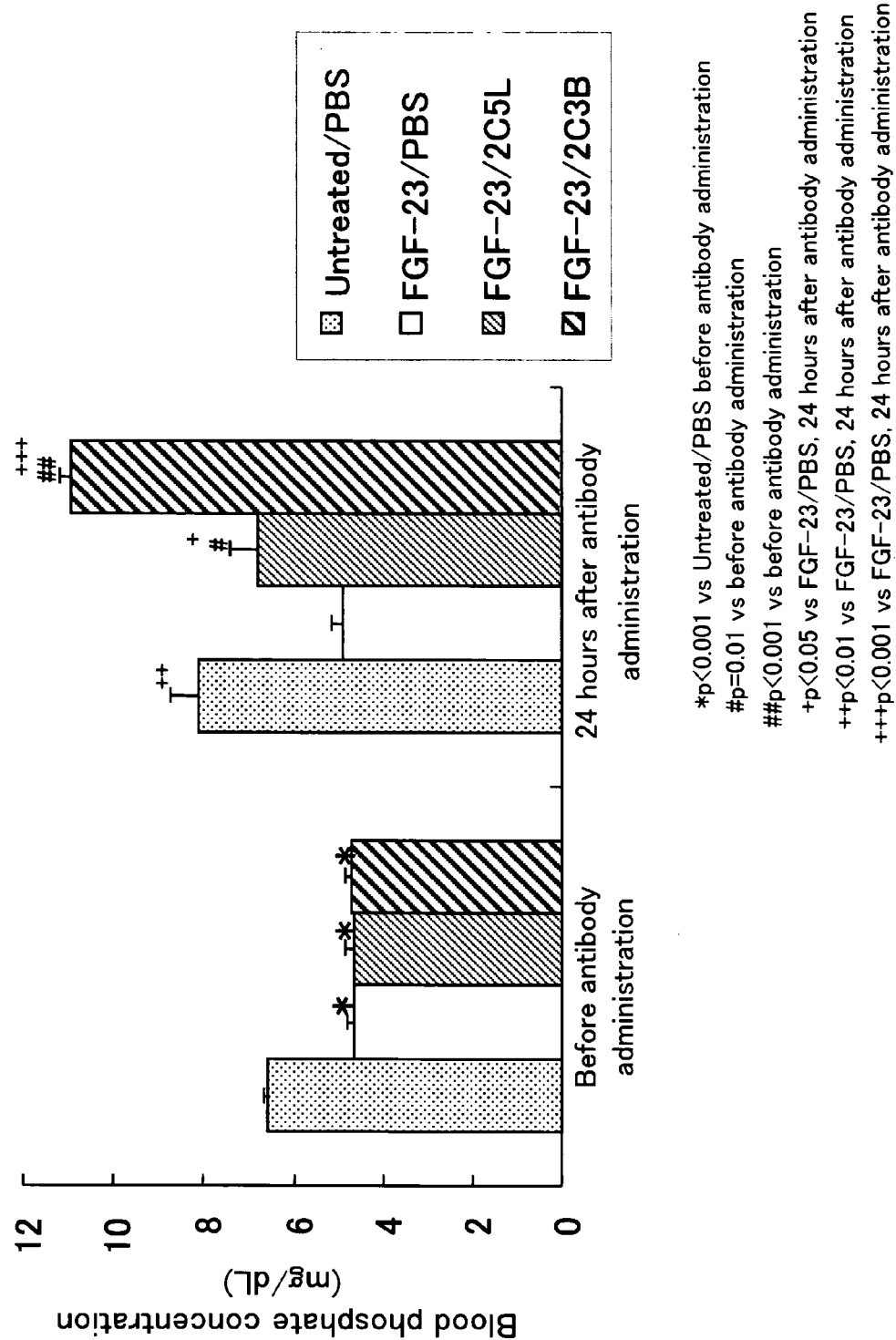

ANTIBODY AGAINST FIBROBLAST GROWTH FACTOR-23

TECHNICAL FIELD

The present invention relates to antibodies against a fibroblast growth factor-23 (FGF-23).

More particularly, the present invention relates to antibodies that provides a method for diagnosing diseases or pathological conditions accompanied by accumulation of or decreases in an FGF-23 protein in vivo by properly detecting and measuring FGF-23, and that enables improvement or treatment of the conditions of diseases or pathological conditions resulting from the excessive action of FGF-23 by suppressing FGF-23, and also relates to a method for preparing and a method for using an antibody.

BACKGROUND ART

Fibroblast growth factor was purified for the first time from the hypophysis of cattle as a substance that stimulates the growth of a fibroblast line NIH3T3. Thereafter, analogous proteins were identified in various tissues, and a group of these substances forms a polypeptide family (FGF family). To date, 22 types of protein belonging to the FGF family have been identified in vertebrates. As the biological activities of these types of protein, not only the fibroblast-growth stimulating activity, but also a wide range of actions are known, such as growth of the mesoderm and the neuroectoderm, angiogenesis, and limb bud formation in the developmental stage. FGF family members vary in terms of expression sites and expression times of genes. The genes thereof are often expressed only at specific sites in the developmental stage or in adults. As genes encoding the receptors of FGF, at least 4 types are known: FGFR1, FGFR2, FGFR3, and FGFR4. In addition, it is known that in FGFR1, FGFR2, and FGFR3, receptor proteins differing in terms of their extracellular domains are independently present due to differences in splicing. Furthermore, it is known that heparin and heparan sulfate proteoglycan interact with FGF and FGF receptors, so as to regulate the action. Furthermore, there are many proteins belonging to the FGF family because of structural similarity, but their biological activities, their receptor-binding abilities, and the like remain almost unknown. Characteristics of the FGF family have been completed as reviews (Ornitz D. M. and Itoh N. Fibroblast growth factors. Genome biology 2: 3005. 1-3005. 12, 2001).

FGF-23 was cloned for the first time from a mouse by data base search utilizing its homology with FGF-15 and the PCR method, and then human FGF-23 was cloned utilizing its sequence homology with that of mouse FGF-23 (Yamashita T., Yoshioka M., and Itoh N. Identification of a Novel Fibroblast Growth Factor, FGF-23, Preferentially Expressed in the Ventrolateral Thalamic Nucleus of the Brain. Biochem. Biophy. Res. Commun. 277: 494-498, 2000). Subsequently, in research on autosomal dominant hypophosphatemic rickets/osteomalacia (hereinafter referred to as ADHR), missense mutations were characteristically discovered in the FGF-23 genes of ADHR patients while narrowing the region of mutant genes in ADHR patients and identifying responsible genes (The ADHR Consortium. Autosomal dominant hypophosphatemic rickets is associated with mutations in FGF-23. Nature Genet. 26: 345-348, 2000). This discovery has strongly suggested physiological importance of FGF-23 in vivo. However, the biological activities of FGF-23 have remained unknown. In the meantime, the biological activity of FGF-23 has been determined by research on tumor-induced osteomalacia. It has been thought that in this disease, a tumor responsible for the disease produces and secretes a humoral factor inducing the disease, and by the action of this factor, morbidity such as hypophosphatemia or osteomalacia is developed.

In search of this disease-inducing factor produced by such responsible tumor, FGF-23 has been cloned as a gene that is expressed at high levels in tumors. Furthermore, it has been shown that by the administration of this factor, hypophosphatemia and osteomalacia are reproduced (Shimada T., Mizutani S., Muto T., Yoneya T., Hino R., Takeda S, Takeuchi Y., Fujita T., Fukumoto S and Yamashita T., Cloning and characterization of FGF23 as a causative factor of tumor-induced osteomalacia. Proc Natl. Acad. Sci. 98: 6500-6505, 2001). This research has shown the involvement of FGF-23 in in vivo metabolic control relating to phosphorus and calcium, and suggested that FGF-23 acts as a systemic factor expressing its action while circulating in vivo. However, the in vivo concentration and metabolism required for the expression of the action of FGF-23 have not been shown, and the physiological role of FGF-23 remains largely unknown. Moreover, as a disease presenting conditions analogous in clinical findings, X-linked hypophosphatemic rickets is known. However, the involvement of FGF-23 in the morbidity has not been revealed. Except for ADHR and tumor-induced osteomalacia, there are no known diseases that have been proven to be associated with FGF-23.

The above tumor-induced osteomalacia is characterized by showing abnormally low levels of blood phosphorus and 1α,25-dihydroxyvitamin D (hereinafter referred to as 1,25D) along with tumorigenesis. It is accompanied by decreased muscle force, or osteomalacia, and may result in dysbasia or dysstasia. In most cases, the responsible tumor for this disease is a benign tumor derived from mesenchymal cells. Most responsible tumors are poor in growth ability, and notable increases are barely observed during follow-up. Furthermore, although the progression of morbidity is observed, detailed examination such as whole body scanning by MRI inspection is often required to find a responsible tumor. Accordingly, some cases where confirmed diagnosis is not given and a diagnosis of hypophosphatemia with unknown causes is made are suspected of being tumor-induced osteomalacia. Currently the only method that results in a confirmed diagnosis of tumor-induced osteomalacia is to confirm recovery from conditions of the disease by tumorectomy. This is because there are no methods for examining the cause and effect relationship between tumorigenesis and conditions of disease by clinical tests. In some cases, removal of non-responsible tumors that are completely independent from conditions of disease has been conducted. To improve such circumstances, development of a method for clinical tests whereby differential diagnosis can be made for tumor-induced osteomalacia has been expected.

The fact that FGF-23 has action controlling in vivo phosphorus metabolism has been discovered. Parathyroid hormones and 1,25D that have been known to have action controlling phosphorus metabolism play a more important role in controlling calcium metabolism rather than in phosphorus metabolism. No molecules mainly controlling phosphorus metabolism have been known, and FGF-23 is expected to have such activity. In the meantime, a close relationship between phosphorus metabolism and calcium metabolism is clinically known. In particular, in terms of calcification of bone tissues and pathological ectopic calcification, it is difficult to consider the two separately. Based on the facts that FGF-23 in an excessive state induces osteomalacia and FGF-23 has action lowering 1,25D, FGF-23 may be involved not only in phosphorus metabolism but also extensively in controlling calcification and bone metabolism. Moreover, some of diseases with abnormalities in organs controlling mineral metabolism consisting mainly of the intestinal tract, the kidney, and the bone tissues may be associated with the excessive accumulation and the deficiency state of FGF-23. Development of a method for testing in vivo concentrations of FGF-23 is also expected to result in an understanding of such diseases, and in precise treatment of the diseases.

Suppression or removal of FGF-23 in morbidity induced by excessive FGF-23 can be a therapeutic method for the disease. One possible method is the inhibition of ligand-receptor interaction using an antagonist for the receptor of FGF-23 or a substance binding to FGF-23, and another possible method involves the removal of FGF-23 using a substance binding to FGF-23. However, there are no known substances that selectively suppress or remove FGF-23 by the above-mentioned methods.

SUMMARY OF THE INVENTION

An object of the present invention is to provide an antibody recognizing FGF-23, and a diagnosis method, a therapeutic method, and a prophylactic method using the antibody against diseases in which FGF-23 is involved.

As a result of intensive studies to achieve the above objectives, we have completed the present invention by obtaining an antibody that specifically recognizes and binds to a partial structure of an FGF-23 protein, and discovering that FGF-23 can be detected using the antibody.

The present invention is as follows.

(1) An antibody obtained by immunizing an animal with a polypeptide which consists of an amino acid sequence represented by SEQ ID NO: 1, or an amino acid sequence derived from the amino acid sequence represented by SEQ ID NO: 1 by deletion, substitution, or addition of 1 or several amino acids, and has fibroblast growth factor-23 activity, which has activity controlling phosphate metabolism or vitamin D metabolism, and is shown by the following (a), (b), or (c):
  (a) an antibody which recognizes an amino acid sequence between the 180th and the $194^{th}$, or the $237^{th}$ and the $251^{st}$ amino acid residues represented by SEQ ID NO: 1;
  (b) an antibody which is produced by a hybridoma whose accession number is FERM BP-7838, FERM BP-7839, FERM BP-7840, or FERM BP-8268; or
  (c) an antibody which is competitive with the antibody produced by the hybridoma whose accession number is FERM BP-7838, FERM BP-7839, FERM BP-7840, or FERM BP-8268 upon binding with the polypeptide consisting of the amino acid sequence represented by SEQ ID NO: 1.

(2) A pharmaceutical composition, which comprises the above antibody as an active ingredient.

The pharmaceutical composition of the present invention may comprise an antibody that recognizes the amino acid sequence between the 180th and the 194th amino acid residues represented by SEQ ID NO: 1. The composition of the present invention is effective against at least one disease selected from tumor-induced osteomalacia, ADHR, XLH, renal osteodystrophy, dialysis osteopathy, osteoporosis, hypophosphatemia, rickets, osteomalacia, dysfunction of the renal tubule, osteopenia, hypocalcemia, disorder of bone extension, disorder of bone calcification, hyperparathyroidism, ectopic calcification, itching, osteosclerosis, Paget's disease, hypercalcemia, hypoparathyroidism, ostealgia, decreased muscle force, skeletal deformation, failure to thrive, and hypo-1,25D-hemia (disease characterized by low levels of 1.25D in blood), and can be used for treating or preventing these diseases.

The pharmaceutical composition comprises an agent promoting osteogenesis comprising the above antibody as an active ingredient.

(3) A method for detecting a fibroblast growth factor-23, which comprises causing an antibody that recognizes a part of an amino acid sequence between the $25^{th}$ and the $179^{th}$ amino acid residues represented by SEQ ID NO: 1 and an antibody that recognizes a part of an amino acid sequence between the 180th and the $251^{st}$ amino acid residues represented by SEQ ID NO: 1 to react with a test sample.

An example of such an antibody (the antibody that recognizes a part of an amino acid sequence between the $180^{th}$ and the $251^{st}$ amino acid residues represented by SEQ ID NO: 1) used in the above detection method is an antibody that recognizes an amino acid sequence between the $180^{th}$ and the $196^{th}$ amino acid residues represented by SEQ ID NO: 1. In addition, a thrombin inhibitor can also be used in the detection method of the present invention.

(4) A kit for detecting a fibroblast growth factor-23, which contains an antibody that recognizes a part of the amino acid sequence between the $25^{th}$ and the $179^{th}$ amino acid residues represented by SEQ ID NO: 1 and an antibody that recognizes a part of the amino acid sequence between the 180th and the 251st amino acid residues represented by SEQ ID NO: 1.

The kit of the present invention contains an antibody that recognizes the amino acid sequence between the 180th and the 196th amino acid residues represented by SEQ ID NO: 1 as an antibody that recognizes a part of the amino acid sequence between the 180th and the 251st amino acid residues represented by SEQ ID NO: 1.

(5) An anti-fibroblast growth factor-23 antibody-binding material, to which at least one antibody selected from the above antibodies is bound.

(6) A medical appliance, which is provided with the above binding material. The medical appliance of the present invention is used for removing the fibroblast growth factor-23 in blood.

(7) A pharmaceutical composition, which comprises as active ingredients at least 2 types of the above antibodies that recognize different sites.

The present invention is explained in detail as follows.

FGF-23 is known to be expressed at high levels in tumors responsible for tumor-induced osteomalacia. When cells secreting FGF-23 are experimentally transplanted into a nude mouse, hypophosphatemia, or osteomalacia, which is a characteristic of tumor-induced osteomalacia, is reproduced. Thus, FGF-23 is thought to be an inducer of tumor-induced osteomalacia. Independently, research and studies have been conducted on a gene responsible for autosomal dominant hypophosphatemic rickets (ADHR), which is one mode of hereditary hypophosphatemia. Thus, FGF-23 has been identified as a gene whose mutations are specifically observed in ADHR patients. These results suggest the involvement of FGF-23 as a pathogenic factor of hypophosphatemic diseases. For the biological activity of FGF-23, it has been confirmed that FGF-23 induces hypophosphatemia in experiments where a recombinant FGF-23 is administered to mice. Based on these results, it is assumed that FGF-23 acts in vivo as a humoral factor to control phosphorus metabolism and bone metabolism. Hence, quantitative and qualitative evaluation of in vivo FGF-23 is very useful in understanding and diagnosing diseases. Furthermore, controlling the biological activity of FGF-23 is expected not only to be able to cure hypophosphatemic diseases for which the involvement of FGF-23 has been shown as described above, but also to enable the control of phosphorus metabolism and bone metabolism, and to apply to therapies for abnormalities in mineral metabolism, metabolic bone diseases, and the like.

The present invention will be described in detail by showing the meanings of the terms used in the present invention.

Single alphabet characters used to denote amino acids in this specification and in drawings of the present application are as follows: (G) glycine, (A) alanine, (V) valine, (L) leucine, (I) isoleucine, (S) serine, (T) threonine, (D) aspartic acid, (E) glutamic acid (N) asparagine, (Q) glutamine, (K) lysine, (R) arginine, (C) cysteine, (M) methionine, (F) phenylalanine, (Y) tyrosine, (W) tryptophan, (H) histidine, and (P) proline. In addition, the meaning of single alphabet characters used to denote the components of DNA is as follows: (A) adenine, (C) cytosine, (G) guanine, and (T) thymine.

Activity controlling phosphate refers to activity controlling phosphate concentrations in blood.

Activity controlling vitamin D metabolism refers to changes in absolute levels of vitamin D existing in vivo and metabolites synthesized in vivo by the use of vitamin D, or potency controlling changes in the existence rate thereof.

1. Antibody Recognizing FGF-23

Human FGF-23 used in the present invention is a polypeptide having the amino acid sequence (SEQ ID NO: 1) described below, and has the above-illustrated characteristics (activity). Furthermore, FGF-23 and a part thereof in the present invention encompass a human FGF-23 derivative having an amino acid sequence substantially the same as that of the primary structure of a natural-type FGF-23, and a part of the human FGF-23 derivative, as long as the later described antibody of the invention of the present application has reactivity.

Here, the term "human FGF-23 derivative having substantially the same amino acid sequence" refers to a protein having an amino acid sequence derived from the amino acid sequence by substitution, deletion, and/or modification of 1 or several amino acids, as long as it has properties (activity) substantially equivalent to those of natural-type human FGF-23. Moreover, a plural number of such substitution, deletion, modification, and addition may be combined. The activity of the human FGF-23 refers to activity that can induce hypophosphatemia or osteomalacia similarly to the above case.

Human FGF-23 of the present invention can be produced appropriately using a method known in the technical field, such as a chemical synthesis method, a cell culture method, or a modified method thereof, in addition to gene recombination techniques. Moreover, a partial sequence of human FGF-23 can also be produced by gene recombination techniques or the chemical synthesis method according to a method known in the technical field described below, or a modified method thereof, or can be produced by appropriately cleaving human FGF-23 isolated by the cell culture method using a proteolytic enzyme or the like.

The antibody in the present invention is an antibody having reactivity to human FGF-23 as defined above or a part thereof, or is a part of such antibody. The antibody of the present invention encompasses a monoclonal antibody comprising a heavy chain and/or light chain having an amino acid sequence derived from the amino acid sequence of each heavy chain and/or light chain composing the antibody by deletion, substitution, or addition of 1 or several amino acids, and can bind to FGF-23. The above-described partial alteration of amino acids (deletion, substitution, insertion, and addition) can be introduced into the amino acid sequence of the human FGF-23 or the antibody of the present invention by partially altering a nucleotide sequence encoding the amino acid sequence. Techniques for these alterations are known by persons skilled in the art, and a commercially available kit for introducing mutations or the like can be used.

(1) Antibody Specifically Recognizing and Binding to a Partial Structure of FGF-23 Protein To obtain an antibody that is useful in detecting FGF-23 and controlling the biological activity of FGF-23, it is effective to obtain an antibody recognizing the structural characteristic of FGF-23, an antibody having high affinity therefor, an antibody capable of neutralizing biological activity, or the like. Since the structure and antigenicity of FGF-23 have been unknown, a plural number of peptides corresponding to partial sequences of FGF-23 were synthesized and antibodies against each peptide were obtained. FGF-23 secreted by expression cells was detected by Western blotting using these antibodies, revealing that the culture supernatant of the expression cells contained a large quantities of low-molecular-weight peptides derived from FGF-23 protein in addition to mature FGF-23 protein. Furthermore, the obtained antibodies exhibited a variety of binding specificities against mature FGF-23 and peptides generated by the cleavage of mature FGF-23.

Furthermore, the binding activities of the antibodies in the liquid phase were revealed by an immunoprecipitation method. Furthermore, a combined use of these site-specific antibodies made it possible to detect peptides having specific sequence regions from various peptides derived from FGF-23. Details concerning the modification and the metabolism of FGF-23 have not been shown. We revealed, when FGF-23 is expressed in CHO cells, the presence of not only full-length protein lacking signal sequences, but also metabolites resulting from cleavage between the $179^{th}$ Arg residue and the $180^{th}$ Ser residue, by carrying out detection experiments using various antibodies obtained in the present invention. In addition, we have revealed that whereas in plasma FGF-23 is present in its full-length form, in serum, cleavage occurs between the $196^{th}$ Arg residue and the $197^{th}$ Ala residue of FGF-23, by conducting an experiment wherein blood samples of plasma and those of serum containing FGF-23 were collected, and the metabolites were detected, as well as an experiment wherein the purified recombinants were admixed with serum. This may be due to thrombin, and cleavage may also occur between the $198^{th}$ Arg and the $199^{th}$ Met.

(2) Production of Antibody

The antibody of the present invention can be produced by the following production method, as an example. Specifically, for example, a non-human mammal such as a human-antibody-producing transgenic mouse is immunized with a product bound with the above-defined human FGF-23 or a part thereof, or their binding complex with an appropriate substance (e.g., bovine serum albumin) for enhancing the antigenicity of an antigen, together with an adjuvant (e.g., Freund's Adjuvant), if necessary. Alternatively, immunization can be conducted by administering an expression vector having FGF-23 incorporated therein. Polyclonal antibodies can be obtained from serum obtained from immunized animals. In addition, monoclonal antibodies can be produced by preparing hybridomas from antibody-producing cells obtained from immunized animals and myeloma cells incapable of producing antibodies by theirselves, cloning the hybridomas, and selecting clones that produce monoclonal antibodies showing specific affinity for the antigens used for immunization.

More specifically, monoclonal antibodies can be produced as described below. Hybridomas secreting monoclonal antibodies can be prepared by, and according to Köhler and Milstein et al.'s method (Nature, 1975 Vol. 256: 495-497).

Specifically, a hybridoma is prepared by fusing antibody-producing cells contained in the spleen, the lymph node, the bone marrow, the tonsils, or the like obtained from an animal immunized as described above, and preferably the lymph node or the spleen, with myeloma cells incapable of producing antibodies derived preferably from mammals such as mice, rats, guinea pigs, hamsters, rabbits, or humans. Screening for hybridoma clones producing monoclonal antibodies can be performed by culturing hybridomas in, for example, a microtiter plate, measuring the reactivity to the immunogens in the culture supernatant in wells where growth is observed by, for example, an enzyme immunoassay method such as ELISA.

Monoclonal antibodies can be produced from hybridomas by culturing hybridomas in vitro and isolating antibodies from the culture supernatant, or by culturing hybridomas in vivo, such as in the ascites of mice, rats, guinea pigs, hamsters, or rabbits, and then isolating antibodies from the ascites.

Moreover, recombinant antibodies can be prepared by cloning a gene encoding a human monoclonal antibody from an antibody-producing cell such as a hybridoma, incorporating the gene into an appropriate vector, introducing the vector into a host (e.g., mammalian cell lines, *Escherichia coli*, yeast cells, insect cells, and plant cells), and then causing the production of antibodies using gene recombination techniques (P. J. Delves, ANTIBODY PRODUCTION ESSENTIAL TECHNIQUES., 1997 WILEY; P Shepherd and C Dean, Monoclonal Antibodies., 2000 OXFORD UNIVERSITY PRESS, J. W. Goding, Monoclonal Antibodies: principles and practice, 1993 ACADEMIC PRESS). Furthermore, transgenic cattle, goats, sheep, or pigs wherein a gene of a target antibody has been incorporated into an endogenous gene using transgenic animal production techniques are produced, and then monoclonal antibodies derived from the antibody gene can be obtained in large quantities from the milk of the transgenic animals. When a hybridoma is cultured in vitro, in accordance with various conditions including the properties of the cell type to be cultured, the purpose of tests and research, culture method, and the like, hybridomas can be grown, maintained, and stored using known types of nutrient media that are used for producing monoclonal antibodies in culture supernatant, or any type of nutrient media induced and prepared from known basic media.

Regarding the polyclonal antibody of the present invention, as shown in Example 5, a chemically synthesized partial peptide of FGF-23 was bound to a bovine thyroglobulin (the carrier protein) and a rabbit was immunized with the product. Then antibodies, which had been induced to act against each peptide by immunization, were purified with an affinity column to which the peptides used for immunization had been immobilized. The properties of the thus obtained antibodies were examined by Western blotting and ELISA, so that the reactivities against the FGF-23 protein were made clear.

Regarding the preparation of the monoclonal antibody of the present invention, immunization was performed by two methods shown in Example 3. The properties of monoclonal antibodies produced by the thus obtained hybridomas, that is, reactivities against immobilized FGF-23 partial peptides shown in Example 9 and reactivity against the FGF-23 protein in the immunoprecipitation experiment shown in Example 10, were examined, so that the binding properties of each antibody with FGF-23 and the specificities of recognition sites were revealed.

2. Method for Detecting FGF-23

(1) Method for Quantitatively Detecting FGF-23 and the Metabolites thereof in Biological Samples While Distinguishing the Two In clinical test, precise measurement of FGF-23 having activity in a biological sample is required. However, fragmentation products resulting from the cleavage of the FGF-23 protein upon the production of FGF-23 or the cleavage of the FGF-23 protein upon the preparation of blood samples, which we have discovered, may be factors that disturb the measurement of FGF-23. In particular, we have shown that activity was lost by cleavage between the $179^{th}$ and the $180^{th}$ amino acid residues represented by SEQ ID NO: 1. Therefore, to detect FGF-23 having activity in a biological sample, the sandwich ELISA method using a combination of an antibody recognizing a part of the amino acid sequence between $25^{th}$ and the $179^{th}$ amino acid residues represented by SEQ ID NO: 1 and an antibody recognizing a part of an amino acid sequence between the $180^{th}$ and the $251^{st}$ amino acid residues represented by SEQ ID NO: 1 is effective. This can be conducted by combining a 2C3B antibody or a 2C5L antibody, the N-terminal side recognition antibody that we have obtained, with a 3C1E antibody or a 1D6A antibody, the C-terminal side recognition antibody (FIG. 5). Furthermore, when a serum sample is used in preparation of a blood sample, the full-length FGF-23 existing in blood may be cleaved at a position between the $196^{th}$ and the $197^{th}$ amino acid residues, or the $198^{th}$ and the $199^{th}$ amino acid residues. In this case, when an antibody recognizing a portion of the $197^{th}$ and the following amino acid residues on the C-terminal side is used, it becomes impossible to carry out measurement reflecting the original quantity of the protein existing in blood. Since this cleavage cannot be observed in plasma (Example 26), even when a serum sample is used, the use of the 3C1E antibody, which we have obtained and which recognizes a position between the $180^{th}$ and the $196^{th}$ amino acid residues, as an antibody for recognizing the C-terminus makes it possible to carry out measurement reflecting the original quantity of the protein existing in blood.

Moreover, upon preparation of a serum sample, thrombin was shown to be an enzyme cleaving FGF-23 (Example 17). Hence, it is also possible to avoid effects resulting from the cleavage of FGF-23 in detection by adding a thrombin inhibitor upon preparation of a serum sample, so as to suppress most cleavages of FGF-23 accompanying the preparation of the serum sample. The thrombin inhibitor may be any of those that do not obstruct the detection of FGF-23, and is preferably hirudin.

Moreover, the present application relates to a kit for detecting FGF-23 containing an antibody recognizing a part of the amino acid sequence between the $25^{th}$ and the $179^{th}$ amino acid residues represented by SEQ ID NO: 1 and an antibody recognizing a part of the amino acid sequence between the $180^{th}$ and the $251^{st}$ amino acid residues represented by SEQ ID NO: 1. In addition to anti-FGF-23 antibodies, if necessary, a stabilizer, a pH adjuster, or the like may be contained in the kit for detecting FGF-23 of the present application.

(2) Method for Detecting FGF-23 with High Sensitivity

Elucidation of the relationship between the in vivo action of FGF-23 and morbidity is clinically useful and is useful in differential diagnosis of tumor-induced osteomalacia and diagnosis of hereditary hypophosphatemic rickets (ADHR, XLH: X-linked hypophosphatemic rickets). Hypophosphatemia, rickets, and osteomalacia, for which no dystrophia and family history are confirmed, are diseases the causes of which are unable to be specified, and thus diagnoses therefor are currently difficult. When an elevated concentration of FGF-23 in blood is observed in such a patient, it is possible to draw up therapeutic guidelines by confirming differential diagnosis of hereditary diseases based on the confirmation of gene mutations, or by finding tumors using a detailed method for detecting tumors that makes it enable the treatment of tumor-induced osteomalacia. Furthermore, because of the possible deep involvement of FGF-23 in biofunctions as a factor controlling phosphorus metabolism and/or a factor controlling vitamin D metabolism, it is thought that the blood concentration fluctuates in morbidity of diseases accompanied by abnormal mineral metabolism, diseases of renal functions, diseases of bone metabolism, and the like. Thus, comparison of the average concentration of FGF-23 in the blood of the healthy adult with a concentration of FGF-23 in the blood of a patient with such a disease may be useful in understanding the morbidity, selecting a therapeutic method, and determining a therapeutic plan. To construct such a FGF-23 detection system, detection sensitivity allowing the FGF-23 concentrations in blood to be measured is required. We have examined by the sandwich ELISA method various combinations of antibodies that we have obtained, thereby enabling quantitative measurement of FGF-23 concentrations in the blood of a healthy adult and a patient with such a disease.

Examples of a method for detecting a substance (referred to as an antigen molecule) that is recognized by an antibody utilizing an antibody include a method of collecting detectable quantities of substrates utilizing the binding of antibodies with antigen molecules, a method of detecting the presence of antigen molecules by detecting antibodies specifically binding to the antigen molecules to be detected, and a method of detecting the presence of antigen molecules by measuring competition that occurs when the antigen molecules to be detected are allowed to be present in specific binding of a known quantity of substrates with antibodies. Examples of qualitative detection methods utilizing these methods include Western blotting, an immunoprecipitation method, and an immunostaining method. Furthermore, examples of quantitative measurement methods that are generally known include radioimmunoassay, ELISA, FACS and the like. When modified or cleaved, antigen molecules to be recognized by antibodies will take a variety of forms. As a detection method that involves specifying a part of these forms, combining antibodies that recognize different sites of a target substance is effective. A representative example of this method is sandwich ELISA.

Upon the completion of the detection method of FGF-23 of the present invention, the presence of a plurality of molecular species resulting from cleavage of the FGF-23 protein is clearly shown in FIG. 1A. In particular, as shown in Example 16, it was shown that FGF-23 existing as a full-length protein in blood is cleaved in serum. As such, there has been a need to develop a detection system considering such cleavage in order to quantitatively and precisely detect FGF-23 in vivo. For this purpose, the combined use of the above antibodies recognizing partial sequences of the FGF-23 protein has proven very useful. Regarding ELISA using polyclonal antibodies, as shown in Example 7, it was shown that the FGF-23 protein and the cleaved fragments thereof can be selectively measured. Moreover, regarding anti-FGF-23 monoclonal antibodies obtained in Examples 3 and 4, specificities to the recognition sites of the FGF-23 protein were analyzed, so that it was revealed that characteristics of binding with FGF-23 can be applied to sandwich ELISA. It was revealed that among the obtained antibodies, the 1D6A antibody, the 2C3B antibody, and the 3C1E antibody can be independently used as immobilized antibodies, and can also be used as antibodies for detection. On the other hand, the 2A2B antibody was improper for any of these uses. Furthermore, it was revealed that the FGF-23 protein is cleaved in vivo and upon the preparation of serum. By combining antibodies respectively recognizing a sequence region between the $25^{th}$ and the $179^{th}$ amino acids of the FGF-23 protein, a sequence region between the $180^{th}$ and the $196^{th}$ amino acids, and a sequence region between the $197^{th}$ and the $251^{st}$ amino acids represented by SEQ ID NO: 1, detection and measurement of the metabolites of the FGF-23 protein can be realized. Among the antibodies of present invention, the 2C3B antibody recognizes the sequence region between the $25^{th}$ and the $179^{th}$ amino acids, and the 3C1E antibody recognizes the sequence region between the $180^{th}$ and the $196^{th}$ amino acids of the FGF-23 protein represented by SEQ ID NO: 1. The 1D6A antibody recognizes the sequence region between the $237^{th}$ and the $251^{st}$ amino acids in SEQ ID NO: 1. In particular, to detect the FGF-23 protein having activity for the purpose of clinical tests or the like, a combination of the antibody recognizing a sequence region between the $25^{th}$ and the $179^{th}$ amino acids with the antibody recognizing the sequence region between the $180^{th}$ and the $196^{th}$ amino acids is preferred in terms of cleavage that occurs upon the preparation of serum. Particularly, a detection system with high sensitivity was realized using the 2C3B antibody or the 2C5L antibody as an immobilized antibody and the 3C1E antibody as an antibody for detection. Moreover, to detect the full-length FGF-23 protein, a combination of the antibody recognizing the sequence region between the $25^{th}$ and the $179^{th}$ amino acids with the antibody recognizing the sequence region between the $237^{th}$ and the $251^{st}$ amino acids is preferred. Particularly, a detection system with high sensitivity was realized using the 2C3B antibody as an immobilized antibody and the 1D6A antibody as an antibody for detection.

3. Diagnosis Methods for Hypophosphatemic Diseases, Rickets, and Osteomalacia

It has been suggested that in ADHR patients, missense mutations of the FGF-23 gene are involved in the induction of hypophosphatemic diseases (The ADHR Consortium. Autosomal dominant hypophosphatemic rickets is associated with mutations in FGF23. Nature Genet. 26: 345-348, 2000). Furthermore, we have identified FGF-23 as a factor inducing diseases, whereby tumors are produced in tumor-induced osteomalacia (Shimada T, Mizutani S, Muto T, Yoneya T, Hino R, Takeda S, Takeuchi Y, Fujita T, Fukumoto S, and Yamashita T. Cloning and characterization of FGF23 as a causative factor of tumor-induced osteomalacia. Proc Natl. Acad. Sci. 98: 6500-6505, 2001). These studies have revealed the possible involvement of FGF-23 in diseases accompanied by hypophosphatemic diseases, rickets, or osteomalacia. However, there have been no methods for quantitatively analyzing FGF-23 in a living body. In the present invention, we have established a specific FGF-23 detection system as described above. Using this system as shown in Example 19, FGF-23 contained in blood samples collected from patients with tumor-induced osteomalacia before tumorectomy and the same collected after tumorectomy were quantitatively measured. As shown in FIG. 14B, although significantly high blood FGF-23 levels were shown before operation, after tumorectomy, the blood FGF-23 concentrations decreased to near the detection limit. In tumor-induced osteomalacia, tumors are generally small, and although symptoms such as hypophosphatemia, decreased muscle force, ostealgia, or osteomalacia are exhibited, causative tumors may not be found. In addition, when tumors are observed, it is impossible to confirm that the tumor produces FGF-23, so that diagnosis differentiating between tumor-induced osteomalacia and other hypophosphatemic diseases showing similar symptoms is difficult. The measurement of the present invention enables detection of increased levels of FGF-23 in blood in tumor-induced osteomalacia, and thus enables diagnosis of cases that have conventionally been impossible to diagnose.

It is said that XLH, which is a disease with the highest incidence rate among patients with hereditary hypophosphatemia, is said to be present in approximately 1 out of 20,000 people. The gene responsible for XLH has been identified as PHEX. This gene comprises 22 exons, and the gene region spans 220 kb, so that it is currently impossible to analyze mutations causing this hereditary hypophosphatemia for the purpose of diagnosis. The presence of cases involving sudden onset and types characterized by onset in adults has been suggested. So far the relationship between PHEX and FGF-23 has not been clarified. As an XLH model animal, an Hyp mouse, which is a spontaneous mutant mouse, is known. The lack of the 3' region of the PHEX gene has been confirmed in this mouse, and the mouse is known to develop hypophosphatemia, rickets, or osteomalacia. By the use of the measurement system of the present invention, as shown in Example 23, we measured blood concentrations of FGF-23 in Hyp mice, and discovered that the FGF-23 concentrations therein were significantly high.

Accordingly, it was shown that the antibody of the present invention, and the detection method or the measurement method using the antibody, enable diagnosis of tumor-induced osteomalacia and XLH. Moreover, it is considered that the measurement method of the present invention can be used for ADHR, which is another form of hypophosphatemic disease and may be caused by mutations in FGF-23.

FGF-23 has activity of decreasing phosphorus concentrations and 1,25D concentrations in blood. However, the physiological role thereof has not yet been well elucidated. By conducting the later-described experiment of the neutralization of FGF-23 activity, we revealed that FGF-23 has an important role in maintaining the metabolic balance of phosphorus or 1,25D even under normal conditions. Therefore, FGF-23 may be involved in phosphorus metabolism, and morbidity of renal diseases, intestinal diseases, mineral metabolic disorders, and diseases with abnormal vitamin D metabolism, with which phosphorus metabolism is deeply involved. Furthermore, also in patients to which 1,25D or a derivative thereof has been administered, fluctuations in FGF-23 may affect morbidity and therapeutic effects. The measurement system of the present invention is thought to make it possible to deepen the understanding of the morbidity of these diseases, and to implement more precise medical practice.

4. Therapeutic Methods Against Diseases, Characterized by Suppressing FGF-23 Activity It is known in tumor-induced osteomalacia and ADHR that the excessive action of FGF-23 induces the diseases. Furthermore, in the present invention, we also revealed that in the case of XLH, high levels of FGF-23 were exhibited in blood. Suppression of FGF-23 is thought to lead to improve hypophosphatemia, rickets, or osteomalacia. In terms of the fact that FGF-23 acts on epithelial cells of the proximal tubule of the kidney, the suppression of FGF-23 may be useful in treating kidney tubule dysfunction. Moreover, in terms of the role of FGF-23 in controlling phosphorus metabolism and vitamin D metabolism, FGF-23 may act so as to provide unfavorable effects in diseases involving abnormal phosphorus metabolism, diseases involving abnormal Ca metabolism, diseases involving abnormal bone metabolism, diseases involving abnormal metabolism accompanying decreased renal functions, metabolic abnormalities accompanying hemodialysis conducted for renal failure, and diseases accompanying kidney transplantation. Similarly, it has been reported that hypophosphatemia is recognized at high frequencies after kidney transplantation and the disease is accompanied by osteopenia, suggesting the involvement of FGF-23 also in these cases. In such cases, not only recovering normal levels of FGF-23 from abnormally elevated levels, but also further decreasing FGF-23 showing normal values as pharmacological treatment may be required. It is considered that antibodies shown in Examples 27 and 28 capable of neutralizing or modifying the activity of FGF-23 are useful in treating various diseases. As shown in Example 25, it was discovered that animals exhibiting hyperphosphatemia due to decreased renal functions exhibit significantly high levels of FGF-23. It is considered that at least a part of abnormalities in vitamin D metabolism accompanying decreased renal functions is an effect resulting from the elevated levels of FGF-23. It is also considered that diseases accompanying the abnormally elevated levels of FGF-23 can be treated by neutralizing or removing the activity of FGF-23 using the antibodies of the present invention. In particular, it is considered that since phosphorus metabolism, calcium metabolism, and vitamin D metabolism are corrected by the antibodies of the present invention, these antibodies may be useful against diseases accompanying abnormalities in mineral metabolism, such as hypocalcemia, hyperparathyroidism, ectopic calcification, and itching, or diseases involving abnormalities in bone metabolism accompanying decreased renal functions, such as renal osteodystrophy, and dialysis osteopathy. Moreover, the use of the antibodies of the present invention may also be useful against cardiovascular hypofunction accompanied by calcification, which is a problem in hemodialysis patients. Moreover, as shown in Example 27, it was revealed that even under normal metabolic conditions, FGF-23 has an important role in mineral metabolism and vitamin D metabolism. In view of not only the above fact that FGF-23 is induced in hyperphosphatemia, but also the facts that FGF-23 rapidly decreases 1,25D and FGF-23 is rapidly induced by 1,25D, the antibodies of the present invention capable of neutralizing or modifying the activity of FGF-23 may have extensive usefulness against diseases with abnormalities in mineral metabolism. This is because the antibodies not only control phosphorus metabolism, vitamin D metabolism, and calcium metabolism by suppressing the action of FGF-23, but also indirectly control hormones for calcium metabolism, such as parathyroid hormones and calcitonin. In particular, the antibodies of the present invention are expected to be effective for treating osteoporosis, osteopenia, osteosclerosis, or Paget's disease exhibiting various forms of morbidity in association with the balance in mineral metabolism and metabolic turnover, or hypercalcemia or hypoparathyroidism. As described above, the antibodies of the present invention may be useful against one or more of the diseases described above.

5. Antibody for Neutralizing the Biological Activities of FGF-23

FGF-23 is thought to have an important role in metabolic control in a living body, as described above. A method for controlling the biological activities of such a factor is thought to be useful for therapies against and prevention of various diseases. An antibody is characterized by specific binding with an antigen molecule, and is known to have an effect on the structure and functions of an antigen molecule, depending on its recognition site. Thus, we aimed at isolation and identification of an antibody capable of controlling the functions of FGF-23, and particularly, capable of suppressing the biological activities of FGF-23. As shown in Examples 27 and 28, we have discovered that administration of an antibody recognizing FGF-23 causes increases in serum phosphorus and in serum 1,25D concentrations. In particular, the antibodies of the present invention used in these examples caused the complete disappearance of the activity of human FGF-23 to lower serum phosphorus and 1,25D, which had been experimentally produced in vivo in mice. Furthermore, in control mice that had not been caused to produce human FGF-23, elevated levels of serum phosphorus and vitamin D were confirmed. This phenomenon was completely opposite to the changes observed when FGF-23 had been administered. Thus, the antibody of the present invention is thought also to suppress mouse endogenous FGF-23. Furthermore, this phenomenon shows that FGF-23 functions as a factor controlling phosphorus metabolism and vitamin D metabolism not only in a state of morbidity, but also in a normal state. The antibodies of the present invention capable of causing the disappearance or attenuation of the biological activity of FGF-23 can control physiological and pathological conditions that are the reflection of the biological activity of FGF-23. The range of the biological activity of FGF-23 that the antibody of the present invention can control is not limited only to phosphorus metabolism and vitamin D metabolism. The antibody can control every biological activity and physiological activity of FGF-23.

Moreover, two or more types of antibodies recognizing different sites of FGF-23 as shown in Example 31, that is, different epitopes, may be used. In this case, the neutralization activity of the antibodies is enhanced, so that the action time of the antibodies can also be maintained for a long period of time. Examples of a combination of 2 or more types of antibodies include an antibody recognizing an amino acid sequence between the $180^{th}$ and the $194^{th}$ or between the $237^{th}$ and the $251^{st}$ amino acid residues represented by SEQ ID NO: 1, and an antibody produced by a hybridoma whose accession number is FERM BP-7838, FERM BP-7839, FERM BP-7840 or FERM BP-8268.

6. Pharmaceutical Composition Comprising Anti-FGF-23 Antibody

The antibody or the pharmaceutical composition of the present invention can be applied for therapies or prevention of various diseases or symptoms in which FGF-23 produced in vivo or in cells expressing FGF-23 is involved. The antibody of the present invention can be used as a pharmaceutical composition against tumor-induced osteomalacia, ADHR, and XLH, and can be expected to have an effect of improving the conditions, which are observed in common among these diseases, of hypoposphatemia, failure of bone calcification, ostealgia, decreased muscle force, skeletal deformation, growth disease, and hypo-1,25D-hemia (disease characterized by low levels of 1,25D in blood). As described above, FGF-23 plays an important role in physiological conditions. The antibody of the present invention can be used as a pharmaceutical composition therapeutically and prophylactically against diseases resulting from abnormalities in mineral metabolism or vitamin D metabolism such as osteoporosis, rickets, hypercalcemia, hypocalcemia, ectopic calcification, osteosclerosis, disorders of bone extension, disorders of bone calcification, Paget's disease, hyperparathyroidism, hypoparathyroidism, and itching, by controlling the phosphorus metabolism-controlling action of FGF-23, or the calcium-metabolism-controlling action mediated by vitamin D metabolism that is controlled by FGF-23. Furthermore, it is clear that blood FGF-23 concentrations increase in renal failure. Hence, the antibody of the present invention can be used therapeutically and prophylactically as a pharmaceutical composition against complications of renal failure or blood dialysis, represented by renal osteodystrophy, dialytic osteopathy, dysfunction of renal tubules, and the like.

Moreover, the antibody of the present invention bound with a therapeutic reagent can be used as a pharmaceutical composition. In tumor-induced osteomalacia, it is known that a tumor excessively produces FGF-23 so as to induce morbidity. Currently, a sole therapeutic method involves the removal of the causative tumor. However, a causative tumor is often small. There have been many case reports of causative tumor being finally discovered by energetic MRI search. In addition, there may be many cases where a diagnosis of hypophosphatemia or osteomalacia with unknown causes is made, because no tumors could be found. The antibody of the present invention is considered to be accumulated in FGF-23-producing tumors in such diseases, because of affinity for FGF-23. As a method for degenerating tumors using this property, it is effective to use a therapeutic reagent bound to the antibody of the present invention. Examples of a therapeutic reagent to be bound to the antibody include (1) radiation isotopes such as iodo (131 Iodine: 131I; 125 Iodine: 125I), yttrium (90Yttrium: 90Y), indium (111 Indium: 111In), and technetium (99m Technetium: 99mTc) (J. W. Goding, Monoclonal Antibodies: principles and practice, 1993 ACADEMIC PRESS), (2) bacterial toxins such as Pseudomonas toxin (Pseudomonas exotoxin), diphtheria toxin, and ricin, and (3) chemotherapeutants such as methotrexate, mitomycin, and calicheamicin (D. J. King, Applications and Engineering of Monoclonal Antibodies, 1998 T. J. International Ltd, M. L. Grossbard., Monoclonal Antibody-Based Therapy of Cancer., 1998 Marcel Dekker Inc). More preferably, a prodrug such as Maytansinoid is preferred (Chari et al., Cancer Res., 1992 Vol 52: 127, Liu et al., Proc Natl Acad Sci USA., 1996 Vol93:8681).

In addition, the scope of the present invention also encompasses a pharmaceutical preparation comprising a purified product of the anti-human FGF-23 antibody. Such a pharmaceutical preparation preferably contains a physiologically acceptable diluent or carrier in addition to an antibody, and may be a product mixed with other antibodies or other drugs such as antibiotics. Examples of an appropriate carrier include, but are not limited to, physiological saline, phosphate buffered saline, phosphate buffered saline glucose solution, and buffered physiological saline. Alternatively, antibodies may be frozen and dried (freeze-dry), and the above buffered aqueous solution may be added to the antibodies, if necessary, so as to reconstitute and use the antibodies. The route of administration may be oral or non-enteral, including intravenous, intramuscular, subcutaneous, and intraperitoneal injections or drug delivery.

When the pharmaceutical composition of the present invention is administered to a patient, the effective dosage per administration is selected from the range between 20 ng and 200 mg per kg of body weight. Alternatively, a dosage of 0.001 to 10000 mg/body weight, preferably 0.005 to 2000 mg/body weight, and more preferably 0.01 to 1000 mg/body weight per patient can be selected. However, the dosage of the pharmaceutical composition of the present invention is not limited to these dosages.

7. Medical Appliances Containing Anti-FGF-23 Antibody

In therapeutic techniques for hemodialysis, plasma exchange, and cell collection, substances in a living body are removed, exchanged, and collected from a part of collected body fluids or body fluids subjected to extracorporal circulation. In such therapeutic techniques, the antibody of the present invention is useful in selective removal of FGF-23 molecules in a living body and selective collection of cells expressing FGF-23, utilizing the property of specifically binding with FGF-23 molecules. In hemodialysis and plasma exchange, a potential method involves the antibody of the present invention being immobilized to parts of materials with which body fluids come into contact. As materials of a dialysis membrane, in addition to a cellulose membrane, a synthetic polymer membrane such as a polyacrylonitrile membrane, a polymethylmethacrytate membrane, an ethylene vinyl alcohol membrane, a polysulfone membrane, a polyamide membrane, a polyethersulfone/polyarylate membrane, and the like are used. Such a membrane to which the antibodies are immobilized by covalent binding can be used for hemodialysis. Furthermore, there may be a method for separating body fluids using a column filled with beads, such as sepharose beads, to which the antibodies have been bound. In addition, another possible method involves immobilizing the antibodies on magnetic beads, admixing the antibodies with antibody-binding molecules to promote binding, and then collecting complexes of the antibodies and target substances using a magnet. Cells are collected by such a method and used for therapies. As described above, the antibody of the present invention that is bound to a base material that is appropriate as a medical device can be used as a medical appliance.

8. Method for Controlling the Molecular Structure and Biological Activity of FGF-23

An important point for maintaining the biological activity of a protein in vivo is to allow the protein to exist while maintaining the three-dimensional structure thereof in vivo. Among biofactors, as observed in the case of an insulin-like growth factor (IGF) or a transforming growth-factor β (TGF-β), there are many cases where a biofactor binds in vivo to another protein so as to control biological activity. For FGF-23, no binding protein is known to date. Examples of the antibody of the present invention include the 2C3B antibody that is thought to strongly recognize the structure of FGF-23 without binding to a partial peptide as shown in Example 9. It is conceivable to be able to control the biological activity of FGF-23 in vivo by creating a state where these antibodies or parts of these antibodies are bound to FGF-23.

9. Method for Efficiently Removing FGF-23

Significantly decreased renal functions require the removal of uremic substances from the body. For the removal of uremic substances with low molecular weights, hemodialysis using a dialytic membrane is practically used. However, the removal of protein with high molecular weights is still a problem. The antibody of the present invention can be used for the specific removal of FGF-23. As performed in hemodialysis, blood for extracorporeal circulation is brought into contact with a material to which the antibody of the present invention has been immobilized, so that FGF-23 can be selectively removed. The use of the antibody as a therapeutic tool is possible for diseases where FGF-23 exists excessively. As shown in Example 25, based on the fact that high levels of FGF-23 are shown at the time of renal failure, FGF-23 may be a factor inducing dialysis complications. In particular, since FGF-23 has action to lower 1, 25D, there is a high probability that FGF-23 functions as a factor inducing a decrease in 1,25D accompanying decreased renal functions. Thus, a method for removing FGF-23 using the antibody of the present invention in dialysis patients may be useful in therapy for dialysis complications.

As described above, we have completed the present invention by obtaining an antibody that can not only recognize FGF-23, but also control physiological, pharmacological, and pathological actions in which FGF-23 is involved, and can be applied for treating, preventing, and diagnosing diseases.

10. Specification of Competitive Antibody

Upon binding with FGF-23, an antibody that recognizes the same site as that of the antibody of the present invention or a site very close to such site is considered to exhibit properties equivalent to the characteristics shown herein. Such a substantially equivalent antibody can be distinguished from other antibodies by conducting experiments related to competitiveness. When 2 or more types of antibodies are allowed to coexist, antibodies showing the property of binding exclusively to each other upon binding with antigens are defined as competitive antibodies. To specify the competitive antibody of the present invention, under conditions where a labeled antibody of the invention binds to the FGF-23 protein, unlabeled antibodies are allowed to exist in excessive quantities, so that determination can be performed. When added antibodies significantly lower the binding of the antibodies of the invention with the FGF-23 protein, it can be determined that the added antibodies compete with the antibodies of the invention.

The specification includes part or all of the contents as disclosed in the specifications and/or drawings of Japanese Patent Application Nos. 2001-401689 and 2002-262020, which are priority documents of the present application.

BRIEF DESCRIPTION OF DRAWINGS

The application contains at least one drawing executed in color. Copies of this patent or patent application publication with color drawing(s) will be provided by the Office upon request and payment of the necessary fee.

FIG. 7 shows the results as detected using the 2A2B and 1C3H antibodies after collecting by an immunoprecipitation method the FGF-23H protein contained in serum collected from nude mice having CHO-FGF23H cells transplanted therein using resins onto which the 1C3H, 1D6A, and 2C3B antibodies were immobilized, and then separating the protein by SDS-polyacrylamide gel electrophoresis. (Example 15)

FIG. 23 shows the gender, identified mutation sites of a phex gene, age upon blood collection, and serum FGF-23 concentrations of 6 patients with X-linked hypophosphatemic rickets (XLH). (Example 30)

FIG. 25C shows the expression amount (upper case) of NaPi2a protein in BBMV prepared from the kidney as analyzed by the Western blotting method, and phosphate transport activity (lower case) thereof on day 4 after single administration of the mixture of antibodies (Ab), the 2C3B antibody and the 3C1E antibody, or a vehicle (PBS) was performed for wild-type mice (WT) and Hyp mice (Hyp). To correct the protein levels of BBMV subjected to the test, the blot used for Western blotting was subjected to CBB staining, and an image of stained beta-actin is shown at the same time. Results of measuring phosphate transport activity are expressed with average value+/−standard deviation and n=3 for each case. (Example 32)

FIG. 29A shows blood osteocalcin concentrations (IRMA kit, Immutopics, Inc.) on week 2 after ovariectomy of established groups: a group (sham/PBS) of mice subjected to sham operation to which vehicles (PBS) were administered, a group (OVX/Abs) of mice subjected to ovariectomy to which the mixture of antibodies, comprised of the 2C3B antibody and the 3C1E antibody, were administered, or a group (OVX/PBS) of mice subjected to ovariectomy to which vehicles (PBS) were administered. Blood osteocalcin concentrations are expressed with average value+/−standard error. "*" and "**" indicate p<0.01, and p<0.001, respectively, which are the results of tests of significance conducted by Student-t. (Example 34)

FIG. 29B shows blood osteocalcin concentrations (IRMA kit, Immutopics, Inc.) on week 4 after ovariectomy of established groups: a group (sham/PBS) of mice subjected to sham operation to which vehicles (PBS) were administered, a group (OVX/Abs) of mice subjected to ovariectomy to which the mixture of antibodies, comprised of the 2C3B antibody and the 3C1E antibody, were administered, or a group (OVX/PBS) of mice subjected to ovariectomy to which vehicles (PBS) were administered. Blood osteocalcin concentrations are expressed with average value+/−standard error. "*" and "**" indicate p<0.01, and p<0.001, respectively, which are the results of tests of significance were conducted by Student-t. (Example 34)

FIG. 31A shows the full-lengths of caudal vertebra as periodically measured after repeated subcutaneous administration (once a week) of vehicles to Hyp mice (Hyp/vehicle), the mixture of antibodies, comprised of the 2C3B antibody and the 3C1E antibody, at 4 mg/kg to Hyp mice (Hyp/low dose of antibodies), the same mixture at 16 mg/kg to Hyp mice (Hyp/high dose of antibodies), or vehicles to wild-type mice (wild-type/vehicle). Results are expressed with average value+/−standard deviation. "*" and "**" indicate p<0.05 and p<0.01, respectively, which are the results of tests of significance conducted by Student-t, when compared with the Hyp group to which vehicles were administered. (Example 35)

FIG. 31C shows changes in body weight as periodically measured after repeated subcutaneous administration (once a week) of a vehicle to Hyp mice (Hyp/vehicle), the mixture of antibodies, comprised of the 2C3B antibody and the 3C1E antibody, at 4 mg/kg to Hyp mice (Hyp/low dose of antibodies), or the same mixture at 16 mg/kg to Hyp mice (Hyp/high dose of antibodies), and a vehicle to wild-type mice (wild-type/vehicle). Results are expressed with average value+/−standard deviation. "*" and "**" indicate p<0.05, and p<0.01, respectively, which are the results of tests of significance conducted by Student-t, when compared with the Hyp group to which a vehicle were administered. (Example 35)

FIG. 34 shows blood phosphate concentrations before administration and at 24 hours after administration of a vehicle to a group (untreated/vehicle) of untreated normal mice, and a vehicle (FGF-23/PBS), the 2C5L antibody (FGF-23/2C5L), or the 2C3B antibody (FGF-23/2C3B) to each group that had been continuously administered with human recombinant FGF-23 using an osmotic pump. Results are expressed with average value+/−standard deviation. "*" indicates p<0.001 which is the result of a test of significant conducted by Student-t for each group before antibody administration, when compared with a group to which a vehicle was administered. "#" and "##" indicate p<0.01 and p<0.001, respectively, which are the results of tests conducted by Student-t for each group before and at 24 hours after administration of the antibodies. "+", "++," and "+++" indicate p<0.05, p<0.01, and p<0.001, respectively, which are the results of tests for significant conducted by Student-t for each group after administration of the antibodies, when compared with those of the group 24 hours after administration of FGF-23/PBS. (Example 38)

SEQUENCE LISTING FREE TEXT

Figure 1:
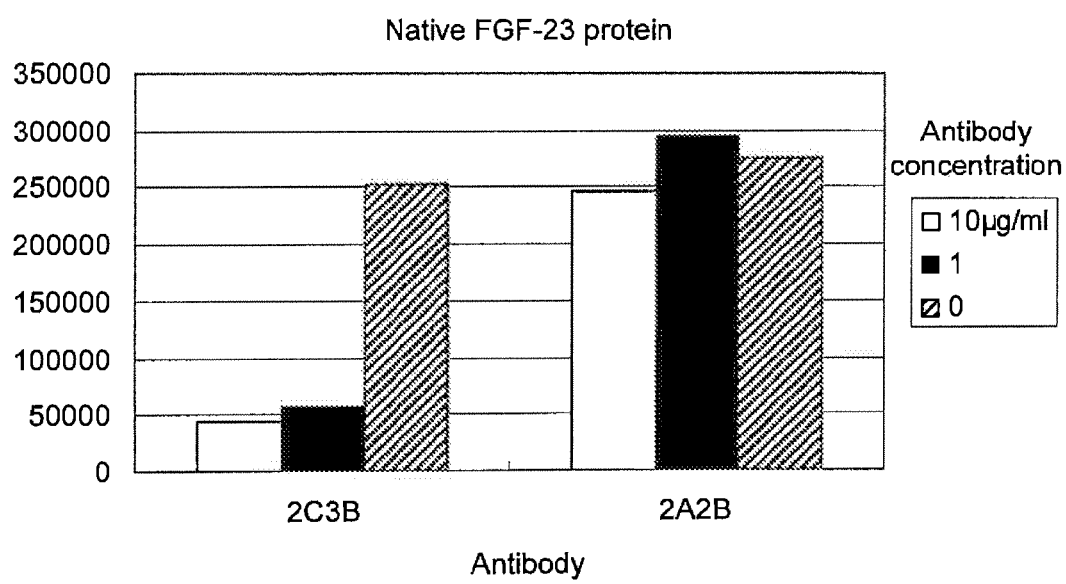
FIG. 1A shows recombinant FGF-23 protein and the metabolites thereof as detected by Western blotting using anti-FGF-23 polyclonal antibodies after the separation of the culture supernatant of CHO-FGF23H cells by SDS-polyacrylamide gel electrophoresis. In the culture supernatant, the full-length FGF-23H protein, and the N-terminal fragment and the C-terminal fragment generated by cleavage between the $179^{th}$ and the $180^{th}$ amino acid residues in the amino acid sequence of SEQ ID NO: 1, are present. The full-length FGF-23H protein and the N-terminal fragment peptide were recognized using hFGF23-48 antibodies and hFGF23-148 antibodies. As N-terminal fragment, the presence of small fragmented peptides was observed. The full-length protein and the C-terminal fragment were detected using anti-His6-tag antibodies. (Example 2)
FIG. 1B shows the FGF-23 full-length protein, the N-terminal fragment and the C-terminal fragment purified from the culture supernatant of CHO-FGF23 cells as detected by CBB staining after separation by SDS-polyacrylamide gel electrophoresis. (Example 2)
FIG. 1C shows a recombinant FGF-23 protein, a recombinant FGF-23RQ protein, and the metabolite thereof as detected by Western blotting using an anti-FGF 23-148 antibody after separately obtaining the culture supernatants of CHO-FGF23H and CHO-FGF23RQ cells, and then separating the cells by SDS-polyacrylamide gel electrophoresis. (Example 5)

SEQ ID NOs: 2-8: synthetic DNA
SEQ ID NOs: 9-24: synthetic peptide
SEQ ID NOs: 25-36: synthetic DNA

BEST MODE FOR CARRYING OUT THE INVENTION

The present invention will be explained more specifically with reference to examples, but the present invention is not limited to the embodiment or technical scope described in the examples.

Example 1

Construction of Recombinant FGF-23 Expression Vector (1) Preparation of FGF-23H Protein Expression Vector cDNA encoding FGF-23 was amplified after keeping the temperature at 96° C. for 1 minute by performing 35 cycles of PCR process, each cycle consisting of 96° C. for 30 seconds, 55° C. for 30 seconds, and 72° C. for 30 seconds using a cDNA library of a responsible tumor of neoplastic osteomalacia as a template, and a F1EcoRI primer (SEQ ID NO: 2), a LHisNot primer (SEQ ID NO: 3), and LA-Taq DNA polymerase. The F1EcoRI primer was annealed to a sequence that is present further upstream on the 5' side of a nucleotide sequence encoding FGF-23, so as to add an EcoR I restriction enzyme site to the 5' side of a region of the amplification fragment encoding FGF-23. The LHisNot primer contains a sequence annealing with a sequence on the 5 side of the termination codon of a sequence encoding FGF-23, and a sequence encoding a His6-tag sequence (His-His-His-His-His-His), followed by the termination codon and a Not I restriction enzyme sequence. As a result, the amplification fragment encoded a sequence of the FGF-23 protein having the His6-tag sequence added to the C-terminus and having the Not I restriction enzyme site located downstream of the His6-tag sequence. This amplification fragment was digested with EcoR I and Not I, and then ligated to a pcDNA3.1Zeo vector (Invitrogen, U.S.A.), which was an animal cell expression vector that had been digested in a similar manner as EcoR I and Not I. The thus prepared expression vector was cloned, and the nucleotide sequence was determined, thereby confirming that it encoded the target FGF-23 protein having the His6-tag sequence added thereto. This vector is referred to as pcDNAFGF-23H.

```
F1EcoRI
CCGGAATTCAGCCACTCAGAGCAGGGCACG        (SEQ ID NO: 2)

LHisNot:
ATAAGAATGCGGCCGCTCAATGGTGATGGTGATGAT  (SEQ ID NO: 3)
GGATGAACTTGGCGAA
```

(2) Construction of FGF-23 Protein Expression Vector

Amplification was performed after keeping the temperature at 94° C. for 1 minute, and then performing 25 cycles of PCR process, each cycle consisting of 94° C. for 30 seconds, 55° C. for 30 seconds, and 72° C. for 1 minute using pcDNA/FGF-23H as a template, and a F1EcoRI primer, LNot primer (SEQ IP NO: 4), and LA-Taq DNA polymerase. After reaction, a cDNA fragment encoding the FGF-23 protein was prepared by blunt-ending the termini of the PCR products with T4 DNA polymerase (Roche, Switzerland), and phosphorylating the DNA termini using polynucleotide kinase (Roche, Switzerland). A pCAGGS expression vector (Niwa H, et al., Gene. 1991, 108: 193-199) was digested with EcoR I, blunt-ended with a Klenow fragment (Roche, Switzerland), and then dephosphorylated using bovine small intestine alkaline phosphatase (TAKARA SHUZO, CO., LTD., Japan). The thus prepared cDNA fragment encoding FGF-23 was ligated to a pCAGGS vector. The thus prepared expression vector was cloned and the nucleotide sequence was determined, thereby confirming that a target sequence encoding the FGF-23 protein was precisely inserted therein. This vector is referred to as pCAGGS/FGF-23.

The above fragment encoding FGF-23 amplified using the F1EcoRI primer and the LNot primer was digested with EcoR I and Not I, and then purified. The purified product was cloned by insertion thereof into EcoR I and Not I restriction enzyme sites of a pEAK8/IRES/EGFP vector that had been prepared by ligating an intramolecular ribosome entry sequence (IRES) and an enhanced-type green fluorescence protein (EGFP) to a pEAK8 expression vector (Edge Biosystem, U.S.A.). The nucleotide sequence of the obtained plasmid was determined, confirming that it encoded the FGF-23 protein. This vector is referred to as pEAK8/IRES/EGFP/FGF-23.

```
LNot:
ATAAGAATGCGGCCGCTCAGATGAACTTGGCGAA   (SEQ ID NO: 4)
``` pCAGGS/FGF-23 was linearized by digestion with EcoR I, and then blunt-ended using a Kenow fragment (Roche, Switerland). This was further digested with BamH I. A DNA fragment containing the cDNA of FGF-23 was sperated and purified by agarose electrophoresis. Furthermore, an INPEP4 expression vector was digested with BgI II, blunt-ended using a Klenow fragment (Roche, Switzerland), digested with BamH I, and then subjected to agarose electrophoresis, thereby purifying the vector. The fragment containing FGF-23 cDNA and the vector were ligated. The thus prepared expression vector was cloned, and then the nucleotide sequence was determined, thereby confirming that the target sequence encoding the FGF-23 protein was precisely inserted therein. This vector is referred to as INPEP4/FGF-23.

(3) Construction of Expression Vector of FGF-23RQH

It has been found that the FGF-23 protein can be easily cleaved between the $179^{th}$ Arg residue and the $180^{th}$ Ser residue. The N-terminal side amino acid sequence of the cleavage site is Arg176-His177-Thr178-Arg179 (SEQ ID NO: 31), agreeing with the Arg-X-X-Arg sequence, which is the recognition sequence of a protein-converting enzyme. Moreover, it is known that a missense mutation in ADHR is a substitution mutation of the $176^{th}$ or the $178^{th}$ Arg residue. Hence, we constructed a vector for experimentally preparing a mutant FGF-23 protein (hereinafter referred to as FGF-23RQH) as a model of the mutant FGF-23 recognized in ADHR, showing resistance against cleavage by a protein-converting enzyme, having His6-tag on the C-terminus, and having Gln residues as a result of substitution of $176^{th}$ and $179^{th}$ Arg residues. In this preparation method, an RQF forward primer (SEQ ID NO: 5) and an RQR reverse primer (SEQ ID NO: 6) containing nucleotide substitution sequences to be used for substituting Arg with Gln were synthesized. Furthermore, in combination with these nucleotide substitution primers, ME1 (SEQ ID NO: 7) and HNt (SEQ ID NO: 8) primers for amplifying the FGF-23 sequences on the 5' side and on the 3' side of the mutation introduction site were prepared. ME1 is a forward primer of a portion containing the initiation codon encoded by FGF-23 cDNA, and has an EcoR I restriction enzyme sequence. HNt is a reverse primer capable of inserting a codon sequence encoding an His6-tag sequence before the termination codon encoded by FGF-23 cDNA, and of adding a Not I restriction enzyme sequence.

```
RQF:
ATACCACGGCAGCACACCCAGAGCGCCGAG       (SEQ ID NO: 5)

RQR:
CTCGGCGCTCTGGGTGTGCTGCCGTGGTAT       (SEQ ID NO: 6)

ME1:
ATGAATTCCACCATGTTGGGGGCCCGCCTCAGG    (SEQ ID NO: 7)

HNt:
ATGCGGCCGCCTAATGATGATGATGATGATGGATGA (SEQ ID NO: 8)
ACTTGGCGAAGGG
```

PCR reaction was performed using 10 ng of pGAGGS/FGF-23 as a template, a combination of RQF and HNt primers, and a combination of ME1 and RQR primers (200 nM each). pfu DNA polymerase (Promega, U.S.A.) was used for reaction. After keeping the temperature at 94° C. for 1 minute, 25 cycles of a reaction process, each consisting of 94° C. for 30 seconds, 55° C. at for 30 seconds, and 72° C. for 1 minute, were conducted. The thus obtained 2 types of reaction solution were diluted 10 times. The reaction solutions (1 μl each) were admixed, so as to prepare a template. ME1 and HNt were added to a final concentration of 200 nM to the template, thereby preparing 50 μl of a PCR reaction solution. After the solution was kept at 94° C. for 1 minute, 25 cycles of a PCR reaction process, each cycle consisting of 94° C. for 30 seconds, 55° C. for 30 seconds, and 72° C. for 1 minute, were conducted. Here, LA Taq DNA polymerase (TAKARA SHUZO, CO., LTD., Japan) was used. The thus obtained amplification product of approximately 800 bp was digested with EcoR I and Not I, and then purified, thereby obtaining an insert DNA. This was cloned by insertion thereof into the EcoR I and Not I restriction enzyme sites of the pEAK8/IRES/EGFP vector that had been prepared by ligating an intramolecular ribosomal entry sequence (IRES) and an enhanced-type green fluorescence protein (EGFP) to a pEAK8 expression vector (Edge Biosystem, U.S.A.). The nucleotide sequence of the obtained plasmid was determined, confirming that the $176^{th}$ and $179^{th}$ Arg had been converted to Gln as expected, and that they encoded the mutant FGF-23 protein having the His6-tag sequence added to the C-terminus. This vector is referred to as pEAK8/IRES/EGFP/FGF-23RQH.

Example 2

Expression of Recombinant FGF-23 Protein and Recombinant Mutant FGF-23 Protein (1) Obtainment of FGF-23H-Expressing Cells Approximately 20 µg of pcDNAFGF-23H was linearized by cleaving at an Fsp I restriction enzyme site within the ampicillin-resistance gene in the vector, and then purified. The purified product was dissolved in 10 µl of pure water, admixed with $1 \times 10^7$ CHO Ras clone-1 cells (Shirahata S., et al., Biosci Biotech Biochem, 59: 345-347, 1995), and then the gene was introduced into a cell by an electroporation method using Gene Pulser II (Bio Rad, U.S.A.). After these cells were cultured in a MEMα culture solution (Gibco BRL, U.S.A.) containing 10% FCS for 24 hours, Zeocin (Invitrogen, U.S.A.) was added to a final concentration of 0.5 mg/ml to the solution, and the resultant was cultured for 1 week. Cells that had adhered and grown were freed using trypsin, and then cloned by a limiting dilution method in the presence of Zeocin at a final concentration of 0.3 mg/ml, thereby obtaining 35 types of cloned cells. Cells expressing the FGF-23H protein at the highest levels among the cells were identified by Western blotting shown below. The culture supernatants of each type of cloned cell were collected, and then subjected to SDS-polyacrylamide electrophoresis. Then the protein was transferred to a PVDF membrane (Millipore, U.S.A.), and the signals derived from the FGF-23H protein at around approximately 32 kDa was detected using anti-His-tag (C-terminus) antibodies (Invitrogen, U.S.A.) and an ECL luminescence system (Amersham Pharmacia Biotech, U.S.A.). As a result, clones referred to as #20 for which the highest expression level had been observed were named CHO-OST311, and then deposited at the International Patent Organism Depositary of the National Institute of Advanced Industrial Science and Technology (Tsukuba Central 6, 1-1-1 Higashi, Tsukuba, Ibaraki, Japan) as of Aug. 11, 2000, under the accession number of FERM BP-7273. In this specification, CHO-OST311 is referred to as CHO-FGF23H.

(2) Obtainment of Cells Expressing FGF-23 and Cells Expressing FGF-23RQH pEAK8/IRES/EGFP/FGF-23 and pEAK8/IRES/EGFP/FGF-23RQH vectors were introduced into CHO Ras clone-1 cells by a gene transfer method using membrane fusion lipids. CHO Ras clone-1 cells were cultured to such an extent that the cells covered approximately 60% of the bottom surfaces of a 6-well plate. Then, the culture solution was removed, and then 1 ml of a serum-free MEMα culture solution was added. 2.5 µg of vectors to be introduced and 10 µl of Transfectam (trademark) (Promega, U.S.A.) were separately admixed with 50 µl of serum-free MEMα culture solutions. The two were then mixed, incubated for 10 minutes, mixed, and then added to a previously prepared 6-well plate. After 2 hours of culture, the culture solutions containing DNA were removed by substitution with culture solutions containing 10% FCS, and then culture was performed overnight. On the next day, puromycin (Sigma, U.S.A.) was added to a final concentration of 5 µg/ml, thereby selecting drug-resistant cells. The drug-resistant cells obtained in this manner were cloned by a limiting dilution method similarly to the above obtainment of the FGF-23H-expressing cells. Furthermore, cell lines expressing target proteins at the highest levels were selected by Western blotting. These cells are referred to as CHO-FGF23 and CHO-FGF23RQ, respectively.

(3) Purification of Recombinant Protein

When recombinants in the culture supernatants of CHO-FGF23H were detected by Western blotting using antibodies against the C-terminal His6-tag sequence, a band at around 32 kDa and a band at around 10 kDa were recognized, as shown in FIG. 1A. When the two bands were excised from gel and the amino acid sequences on the N terminal side were determined, an amino acid sequence beginning from the $25^{th}$ amino acid residue of SEQ ID NO: 1 was detected in the band of a larger molecular weight, suggesting that the signal sequence had been removed during the secretion process from the FGF-23 protein. On the other hand, an amino acid sequence beginning from the $180^{th}$ amino acid residue in SEQ ID NO: 1 was confirmed in the band of a smaller molecular weight, revealing that the fragments had been generated by the cleavage between positions 179 and 180. By detection using polyclonal antibodies recognizing the N-terminal side of FGF-23, the presence of a peptide thought to have a sequence to position 179 was also recognized.

1000 ml of the culture supernatant of the CHO-FGF23H cells was subjected to centrifugation at 16,200 g for 15 minutes at 4° C., so as to remove suspended cells. The supernatant was then passed through a column (internal diameter of 30 mm×length of 200 mm) filled with SP-sepharose FF (trademark) (Amersham Pharmacia Biotech, U.S.A.), so that peptides corresponding to the $180^{th}$ to the $251^{st}$ amino acid residues in SEQ ID NO: 1 and having His6-tag sequence added thereto passed through the column without being adsorbed, while peptides corresponding to the $25^{th}$ to the $251^{st}$ amino acid residues in SEQ ID NO: 1 (hereinafter, may also be referred to as the full-length FGF-23 protein) having an His6-tag added thereto were adsorbed to the column. When the adsorbed substances in the column were eluted with an NaCl concentration gradient ranging from 0 to 0.7 M in a 50 mM sodium phosphate buffer (pH 6.7), the full-length FGF-23 protein having an His6-tag added thereto was observed in fractions eluted with approximately 0.3 M NaCl, peptides thought to have sequences ranging from the $179^{th}$ amino acid residue to the N-terminal side of SEQ ID NO: 1 were confirmed in fractions eluted with approximately 0.4 M NaCl. The fractions separated with the SP-Sepharose column in this manner could then be further separated by applying them to a Talon Superflow (trademark) (Clontech, U.S.A.) metal affinity column. The sequence ranging from the $179^{th}$ amino acid residue to the N-terminal side also had affinity for the metal column, so that it was effective for purification. Further purification was performed using an SP-Sepharose column, so that the full-length FGF-23H could be obtained as a single band by CBB staining. The results are shown in FIG. 1B.

The FGF-23 protein can also be purified by a similar method. The culture supernatant of CHO-FGF23 was filtered through a SuperCap (trademark) (Pall Gelman Laboratory, U.S.A.) membrane with a pore size of 0.2 µm, and then the filtered solution was applied to an SP-Sepharose FF (Amersham Pharmacia Biotech, U.S.A.). Substances having weak affinity for the column were washed with a 50 mM sodium phosphate buffer (pH 6.7) for elution. When protein retained by the column was eluted with an NaCl concentration gradient ranging from 0 to 0.7 M, the full-length FGF-23 protein was observed in fractions eluted with approximately 0.3 M NaCl. The protein was adsorbed to a Talon Superflow (trademark) (Clontech, U.S.A.) metal affinity column, washed with a 50 mM sodium phosphate buffer (pH 6.7), and then varied concentrations of imidazole were added to the column, thus eluting and purifying the protein. Furthermore, fractions containing target protein were adsorbed to an SP Sepharose FF column, eluted, and then purified. By a similar method, the full-length FGF-23RQ protein was purified from the CHO-FGF23RQ supernatant.

Example 3

Obtainment of Hybridomas Producing Mouse Monoclonal Antibodies Against Human FGF-23

Monoclonal antibodies were prepared in this example according to a general method as described in Introduction to Monoclonal Antibody Experimental Protocols (Tamie Ando, et al., "*Tan-kurohn Koutai Jikken Sosa Nyumon*," KODANSHA, 1991) and the like. Balb/c mice were used as animals to be immunized. Immunization with human FGF-23 was performed by the following 2 types of methods depending on differences in immunogens.

(1) Immunization with a Combination of Administration of Vectors and Administration of Recombinant Protein Initial immunization was carried out for Balb/c mice by introducing the INPEP4/FGF-23 vectors prepared in Example 1 (10 or 50 µg/mouse) intravenously using Trans IT (trademark) In Vivo Gene Delivery System reagent (TAKARA SHUZO, Japan). Booster immunization was performed by introducing the same vectors once in week 1 after the initial immunization. Furthermore, the FGF-23 RQH protein (20 to 30 µg/mouse) prepared in Example 2 was suspended in RIBI adjuvants (Corixa, U.S.A.) containing squalene, Tween80, Monophosphoryl lipid A, and Trehalose dimycolate, so as to prepare emulsions. Booster immunization was performed 4 or 5 times by intraperitoneal injection of the emulsions. Subsequently, on day 4 before the obtainment of splenocytes described below, mice were immunized by tail intravenous injection of the FGF-23H protein (18 µg/mouse) prepared in Example 2.

(2) Immunization Using Human FGF-23

Initial immunization was performed for Balb/c mice by intraperitoneal injection of a suspension prepared by suspending FGF-23 (22 µg/mouse) prepared in Example 2 in the above RIBI adjuvants. Furthermore, booster immunization was performed once every week by intraperitoneal injection of the same protein over a period of 4 weeks. On day 3 before the obtainment of splenocytes as described below, immunization was performed by tail intravenous injection of FGF-23 (10 µg/mouse).

(3) Preparation and Selection of Hybridoma

Spleens were excised from the mice immunized as described above. Splenocytes collected from the spleens were mixed at a 5:1 proportion to mouse myeloma SP2/0 (ATCC: CRL 1581), and then the cells were fused using polyethylene glycol 1500 (Roche Diagnostics, Japan) as a fusion agent, thereby preparing hybridomas. The hybridomas were selected by culturing the cells in HAT-containing DMEM media (Gibco BRL, U.S.A.) containing 10% Fetal Calf Serum (FCS), hypoxanthine (H), aminopterin (A), and thymidine (T). Furthermore, cloning was performed by a limiting dilution method using HT-containing DMEM media. Thus, cloned hybridomas derived from a single cell were obtained.

(4) Selection of Cloned Hybridoma Producing Anti-FGF-23 Antibodies

Hybridomas producing antibodies specifically recognizing the FGF-23 protein was selected by examining the binding between antibodies produced by the hybridomas and the FGF-23 protein. Selection of hybridomas obtained by immunization conducted according to the 1st method above was conducted as follows. 50 µl of a solution of the FGF-23H protein diluted to a concentration of 1 µg/ml in a 50 mM NaHCO3 solution was added to each well of a 96-well microplate for ELISA (Maxisorp (trademark), Nunc, U.S.A.). Incubation was performed at 37° C. for 30 minutes or 4° C. for 12 hours, so that the FGF-23H protein was adsorbed to the microplate. Next, the solution was removed, a blocking reagent (SuperBlock (trademark) Blocking Buffer, PIERCE, U.S.A.) was added to each well, and then incubation was performed at room temperature for 30 minutes. Each well was then washed twice with Tris-buffered saline containing 0.1% Tween20 (500 mM NaCl-containing TRIZMA pre-set crystals (trademark), Sigma, U.S.A.) (T-TBS). 50 µl of the culture supernatant of each type of hybridoma was added to each well of the microplate that had been coated with the FGF-23H protein as described above. After 30 minutes of reaction, each well was washed twice with T-TBS. Subsequently, 50 µl of peroxidase-labeled goat anti-mouse IgG antibodies (Zymed laboratories, U.S.A.) diluted 3,000-fold was added to each well, followed by incubation at room temperature for 30 minutes. The wells were washed 3 times with T-TBS and 50 µl of a substrate buffer containing tetramethylbenzidine (Denmark, DAKO) was added to each well, followed by incubation at room temperature for 15 minutes. Next, 50 µl of 0.5 M sulfuric acid was added to each well, so as to stop reaction. Absorbance at a wavelength of 450 nm was measured using a microplate reader (MTP-300, CORONA ELECTRIC CO., LTD., Japan) with a reference wavelength of 570 nm. Here, the hybridomas showing clear increases in absorbance were selected, and a similar experiment was conducted using the FGF-23 protein, so that clones for which binding with FGF-23 had been re-confirmed were selected. Thus, 9 types of clone were obtained as hybridomas producing antibodies recognizing the FGF-23 protein.

Among these clones, 1C3H, 1D6A, 2A2B, 2C3B, and 2C5L described below were included.

Hybridomas obtained by immunization conducted according to the 2nd method above were selected as follows. 50 µl of a solution of the FGF-23 protein diluted to a concentration of 1 µg/ml in a 50 mM NaHCO3 solution was added to each well of a 96-well microplate for ELISA (Maxisorp (trademark), Nunc, U.S.A.). Incubation was performed at 4° C. for 10 hours, so that the FGF-23 protein was adsorbed to the microplate. Next, the solution was removed, a blocking reagent (SuperBlock (trademark) Blocking Buffer, PIERCE, U.S.A.) was added to each well, and then incubation was performed at room temperature for 30 minutes. Each well was then washed twice with Tris-buffered saline (T-TBS) containing 0.1% Tween20. 50 µl of the culture supernatant of each type of hybridoma was added to each well of the microplate that had been coated with the FGF-23H protein. After 30 minutes of reaction, each well was washed twice with Tris-buffered saline (T-TBS) containing 0.1% Tween20. Subsequently, 50 µl of peroxidase-labeled goat anti-mouse IgG antibodies (Zymed laboratories, U.S.A.) diluted 3,000-fold was added to each well, followed by incubation at room temperature for 30 minutes. The wells were washed 3 times with T-TBS and 50 μl of a substrate buffer containing tetramethylbenzidine (Denmark, DAKO) was added to each well, followed by incubation at room temperature for 15 minutes. Next, 50 μl of 0.5 M sulfuric acid was added to each well, so as to stop reaction. Absorbance at a wavelength of 450 nm was measured using a microplate reader (MTP-300, CORONA ELECTRIC CO., LTD., Japan) with a reference wavelength of 570 nm. Here, hybridomas showing clear increases in absorbance were selected. Thus, 4 types of new clones were obtained as hybridomas producing antibodies recognizing the FGF-23 protein. Among these clones, 3C1E was included.

The subclasses of the thus obtained antibodies that specifically recognize the FGF-23 protein was identified using an Iso Strip mouse monoclonal antibody isotyping kit (Roche, U.S.A.). The results are shown in Table 1.

TABLE 1

| Anti-human FGF-23 antibodies | | |
|---|---|---|
| Hybridoma clone | Subclass | ELISA 450 nm–570 nm |
| 1C3H | IgG1(κ) | 3.39 |
| 1D6A | IgG1(κ) | 3.21 |
| 2A2B | IgG1(κ) | 2.67 |
| 2C3B | IgG1(κ) | 1.21 |
| 3C1E | IgG1(κ) | 3.5 or more |
| 2C5L | IgG1(κ) | 1.38 |

Among the above hybridoma clones, 3 hybridoma clones (2C3B, 3C1E, and 1D6A) were internationally deposited under the Budapest Treaty at the International Patent Organism Depositary of the National Institute of Advanced Industrial Science and Technology (Tsukuba Central 6, 1-1-1 Higashi, Tsukuba, Ibaraki, Japan) as of Dec. 26, 2001. Furthermore, the 2C5L hybridoma clone was deposited internationally under the Budapest Treaty at the International Patent Organism Depositary of the National Institute of Advanced Industrial Science and Technology (Tsukuba Central 6, 1-1-1 Higashi, Tsukuba, Ibaraki, Japan) as of Jan. 6, 2003. The accession numbers of these clones are as follows.
2C3B: FERM BP-7838
3C1E: FERM BP-7839
1D6A: FERM BP-7840
2C5L: FERM BP-8268

Example 4

Preparation of Monoclonal Antibodies (1) Preparation of Culture Supernatants Containing Anti-FGF-23 Antibodies Hybridomas producing anti-FGF-23 antibodies were acclimatized in eRDF media (KYOKUTO PHARMACEUTICAL INDUSTRIAL CO., LTD. Japan) containing 10 μg/ml bovine insulin (Sigma, U.S.A.), 5.5 μg/ml human transferrin (Sigma, U.S.A.), 0.01 mM ethanolamine (Sigma, U.S.A.), and 5 ng/ml sodium selenite (Sigma, U.S.A.). Hybridomas for the preparation of antibodies were cultured in spinner flasks. The culture solution was passed through a filter with a pore size of 0.2 μm (Pall Gelman Laboratory, U.S.A.) so as to remove waste matters such as hybridomas, thereby collecting culture supernatants containing antibodies.

(2) Purification of Monoclonal Antibodies using Protein G

The culture supernatant containing anti-FGF-23 antibodies was passed through a protein G Sepharose 4FF column (Amersham Pharmacia Biotech, U.S.A.), so that the antibodies were adsorbed to the column. The antibodies were then eluted using a 0.1 M glycine buffer (pH 2.8). 1 M Tris-HCl was added to the elution fractions to adjust the pH to 7.2. The thus prepared antibody solution was dialyzed and substituted with PBS(−) using a dialysis membrane with a molecular weight cutoff of 10000 (Spectrum Laboratories, U.S.A.) and filter sterilized using a MILLEX-GV membrane filter with a pore size of 0.22 μm (Millipore, U.S.A.), thereby obtaining purified anti-FGF-23 antibodies. The concentrations of purified antibodies were calculated by measuring absorbance at 280 nm, followed by calculation with 1 mg/ml as 1.35 OD.

(3) Purification of Monoclonal Antibodies Using Protein A

Antibodies were affinity-purified from the culture supernatant containing anti-FGF-23 antibodies using a protein A carrier column (IBL Co., Ltd., Japan), a glycine buffer (pH 8.9) as adsorption buffer, and a citric acid buffer (pH 4.0) as an elution buffer. 1 M Tris-HCl was added to the elution fraction containing the antibodies, so as to adjust pH to around 7.2. Then, the solution containing the antibodies was substituted with PBS(−) using a dialysis membrane and filter-sterilized with a membrane filter with a pore size of 0.22 μm, thereby obtaining purified anti-FGF-23 antibodies. The concentrations of the purified antibodies were calculated by measuring absorbance at 280 nm, followed by calculation with 1 mg/ml as 1.35 OD.

Each of the thus obtained purified monoclonal antibodies is expressed using the name of the hybridoma producing the given antibody. For example, antibodies produced by 1D6A hybridomas are described as 1D6A antibodies.

Example 5

Preparation of Anti-FGF-23 Partial Peptide Polyclonal Antibodies (1) Synthesis of Peptides Corresponding to FGF-23 Partial Sequence The degree of hydrophobicity of the polypeptide of SEQ ID NO: 1 was predicted using the calculator function of MacVector version 6.5.1, and then sites appropriate for the preparation of peptide antibodies were predicted. With the condition that sites that have high degree of hydrophilicity and can be subjected to sugar chain modification or phosphorylation are excluded, partial sequences inferred to be appropriate for the preparation of antibodies were extracted. As a result, an hFGF23-25 peptide (SEQ ID NO: 9) comprising 15 amino acid residues beginning from the 25$^{th}$ tyrosine (residue number: 25) of SEQ ID NO: 1 and having a cysteine residue added to the C-terminus of the peptide, an hFGF23-48 peptide (SEQ ID NO: 10) comprising 20 amino acid residues beginning from the 48$^{th}$ arginine and having a cysteine residue added to the C-terminus of the peptide, an hFGF23-114 peptide (SEQ ID NO: 11) comprising 15 amino acid residues beginning from the 114$^{th}$ arginine and having a cysteine residue added to the C-terminus of the peptide, an hFGF23-148 peptide (SEQ ID NO: 12) comprising 16 amino acid residues beginning from the 148$^{th}$ glycin and having a cysteine residue added to the C-terminus of the peptide, an hFGF23-170 peptide (SEQ ID NO: 13) comprising 10 amino acid residues beginning from the 170$^{th}$ asparagines and having a cysteine residue added to the N-terminus of the peptide, an hFGF23-174 peptide (SEQ ID NO: 14) comprising 14 amino acid residues beginning from the 174$^{th}$ proline and having a cysteine residue added to the C-terminus of the peptide, an hFGF23-180 peptide (SEQ ID NO: 15) comprising 15 amino acid residues beginning from the 180$^{th}$ serine and having a cysteine residue added to the C-terminus of the peptide, an hFGF23-210 peptide (SEQ ID NO: 16) comprising 13 amino acid residues beginning from the 210$^{th}$ Leu and having a cysteine residue added to the C-terminus of the peptide, and an hFGF23-237 peptide (SEQ ID NO: 17) comprising 15 amino acid residues beginning from the 237$^{th}$ glycine were selected as antigens, and chemically synthesized.

```
hFGF23-25:
YPNASPLLGSSWGGLC         (SEQ ID NO: 9)

hFGF23-48:
RNSYHLQIHKNGHVDGAPHQC    (SEQ ID NO: 10)

hFGF23-114:
RFQHQTLENGYDVYHSPQYHC    (SEQ ID NO: 11)

hFGF23-148:
GMNPPPYSQFLSRRNEC        (SEQ ID NO: 12)

hFGF23-170:
CNTPIPRRHTR              (SEQ ID NO: 13)

hFGF23-174:
PRRHTRSAEDDSERC          (SEQ ID NO: 14)

hFGF23-180:
SAEDDSERDPLNVLKC         (SEQ ID NO: 15)

hFGF23-210:
LPSAEDNSPMASDC           (SEQ ID NO: 16)

hFGF23-237:
GGTGPEGCRPFAKFI          (SEQ ID NO: 17)
```

(2) Preparation of Polyclonal Antibodies Against Anti-FGF-23 Partial Peptide

All the above peptides were bound to bovine thyroglobulin, the carrier protein, via their own cysteine residues, and then used for immunization. For immunization, 3 rabbits were used per antigen peptide. Initial immunization was conducted by preparing emulsions (100 µg/rabbit) using peptides bound to the carrier protein using Freund's complete adjuvants, and intradermally or subcutaneously administering the emulsions to rabbits. 1 week after the initial immunization, emulsions prepared using 100 µg of peptides bound to the carrier protein using Freund's incomplete adjuvants were similarly administered. The same administration was conducted 6 times at intervals of 2 weeks, and then exsanguination was performed 1 week after the final administration, thereby preparing antiserum.

To prepare an affinity column for the purification of anti-FGF-23 partial peptide antibodies from rabbit serum, each peptide used for immunization was immobilized on gel using a SulfoLink Kit (PIERCE, U.S.A.). Anti-serum was added to the column using PBS(−) as an adsorption buffer, so as to retain antibodies binding to the peptides used for immunization in the column. Next, the antibodies bound to the column were eluted using a 0.1 M glycine buffer (pH 2.5 to 3.3) as an elution buffer, and were then collected. 1 M Tris-HCl was added to the eluted fractions to adjust pH to around 7.2. The thus prepared antibody solution was subjected to a NAP25 gel filtration column (Amersham Pharmacia Biotech, U.S.A.), so that the buffer was substituted with PBS(−). Filter sterilization was performed using a MILLEX-GV membrane filter (Millipore, U.S.A.) with a pore size of 0.22 µm, thereby obtaining antibodies against each peptide. The concentrations of purified antibodies were calculated by measuring absorbance at 280 nm, followed by calculation with 1 mg/ml as 1.35 OD. Each of the thus obtained purified antibodies is expressed using the name of a peptide used for immunization. For example, an antibody obtained by the immunization with the hFGF23-25 peptide of SEQ ID NO: 9 is described as an hFGF23-25 antibody.

(3) Recognition of FGF-23 Protein and Metabolites thereof by anti-FGF-23 Partial Peptide Antibodies The FGF-23H protein and metabolites thereof in the supernatant of CHO-FGF23H-expressing cells were analyzed by Western blotting using the hFGF23-48 and hFGF23-148 antibodies obtained by the above method. As shown in FIG. 1A, full-length FGF-23H protein of around 32 kDa was detected with both of these antibodies. Furthermore, metabolites with a size of around 18 kDa or less were observed, and they were considered to be derived from fragments on the N-terminal side resulting from the cleavage of the FGF-23 protein between the 179$^{th}$ and the 180$^{th}$ amino acid residues of the amino acid sequence of SEQ ID NO: 1. The hFGF23-48 antibody recognized smaller fragmented metabolites. FGF-23RQ protein and metabolites thereof in the culture supernatant of CHO-FGF23RQ producing mutant protein avoiding cleavage between the 179$^{th}$ and 180$^{th}$ amino acid residues were examined using hFGF23-148 antibodies. As shown in FIG. 1C, fragmented peptides that had been recognized in the case of FGF-23H became undetected. Based on the above result, it is considered that in the metabolism by the cleavage of the FGF-23 protein, the N-terminal fragments generated by cleavage between the 179$^{th}$ and 180$^{th}$ amino acid residues are further fragmented into smaller sizes, but such small fragments are generated after cleavage has occurred between the 179$^{th}$ and the 180$^{th}$ amino acid residues. Hence, it was revealed that determining the presence or the absence of cleavage between the 179$^{th}$ and the 180$^{th}$ amino acid residues is very important when considering the metabolism of the FGF-23 protein.

Example 6

Preparation of Biotinylated Antibodies

Biotinylation was performed using the 9 above-purified types of polyclonal antibodies against the FGF-23 partial peptides and some of 13 types of anti-FGF-23 monoclonal antibodies. 10 µl of a solution that had been prepared by dissolving Biotin-AC5-Osu (DOJINDO LABORATORIES. Japan) to dimethylformamide at a concentration of 1.82 mg/ml was added to 1 ml of an antibody solution that had been diluted to a concentration of 1 mg/ml with a 50 mM sodium hydrogen carbonate solution, and then the resultants were admixed by being turned upside down at 4° C. for 2 hours. Subsequently, the reaction solution was applied to a NAP10 column (Amersham Pharmacia Biotech, U.S.A.), unreacted Biotin-AC5-Osu was removed, and the solvent was substituted with PBS(−). Thus, 9 types of biotin-labeled anti-FGF-23 partial peptide polyclonal antibodies and 5 types of biotin-labeled anti-FGF-23 monoclonal antibodies (1C3H antibody, 1D6A antibody, 2A2B antibody, 2C3B antibody, and 3C1E antibody) were obtained.

Example 7

Sandwich ELISA Method Using Polyclonal Antibodies Recognizing Specific Site of FGF-23

(1) Construction of Sandwich ELISA System

The construction of a sandwich ELISA system was examined by combining 8 types of antibodies (hFGF23-25 antibody, hFGF23-48 antibody, hFGF23-114 antibody, hFGF23-148 antibody, hFGF23-170 antibody, hFGF23-180 antibody, hFGF23-210 antibody, and hFGF23-237 antibody) as antibodies for immobilization and antibodies for detection, among the above 9 types of polyclonal antibodies against the FGF-23 partial peptide sequences.

To immobilize antibodies, 8 types of anti-FGF-23 partial peptide polyclonal antibodies (hFGF23-25 antibody, hFGF23-48 antibody, hFGF23-114 antibody, hFGF23-148 antibody, hFGF23-170 antibody, hFGF23-180 antibody, hFGF23-210 antibody, and hFGF23-237 antibody) were diluted to 30 μg/ml with a 50 mM sodium hydrogen carbonate solution. 50 μl of the solution was added per well of a 96-well plate for ELISA (Maxisorp (trademark), Nunc, U.S.A.), and then incubated at 37° C. for 1.5 hours. Subsequently, the reaction solution was removed, 50 μl of SuperBlock (trademark) (PIERCE, U.S.A.) was added per well, 60 minutes of incubation was performed at room temperature, so that blocking was conducted. After the solution was removed, 50 μl of 1 μg/ml FGF-23H protein was added per well and incubated at room temperature for 1 hour, so as to bind the protein with the immobilized antibodies. After antibody reaction, the wells were washed 3 times with T-TBS. The above 8 types of biotin-labeled anti-FGF-23 partial peptide antibodies (hFGF23-25 antibody, hFGF23-48 antibody, hFGF23-114 antibody, hFGF23-148 antibody, hFGF23-170 antibody, hFGF23-180 antibody, hFGF23-210 antibody, and hFGF23-237 antibody) were diluted with T-TBS containing 10% Blockace (DAINIPPON PHARMACEUTICAL CO., LTD. Japan) to 10 μg/ml. These antibodies and a T-TBS solution containing 10% Blockace (DAINIPPON PHARMACEUTICAL CO., LTD. Japan) as a control were separately added at 50 μl per well. Each solution was incubated at room temperature for 30 minutes, so as to conduct secondary antibody reaction. After each well was washed 3 times with T-TBS, 50 μl of HRP-labeled streptavidin (DAKO, Denmark) diluted 5000-fold with T-TBS containing 10% Blockace was added per well. The solutions were incubated at room temperature for 30 minutes, so as to bind the streptavidin with biotin-labeled antibodies. Each well was washed 4 times with T-TBS and 50 μl of tetramethylbenzidine (DAKO, Denmark), which is a peroxidase chromogenic substrate, was added per well so as to cause color development at room temperature for 15 minutes. 50 μl of 0.5 M sulfuric acid solution was added per well, so as to stop reaction. Measurement was conducted using MTP-300 (system for measuring absorbance) for a 96-well plate (CORONA ELECTRIC CO., LTD., Japan), and values were obtained by subtracting absorbance at 570 nm from absorbance at 450 nm (Table 2). In the case of the control to which biotin-labeled antibodies had not been added, all the values obtained for 450 nm-570 nm were 0.06 or less. However, as shown in Table 2, in the case of multiple combinations of immobilized antibodies and antibodies for detection, values obtained for 450 nm-570 nm were significantly elevated. As shown in FIG. 1, since polypeptides generated by the cleavage of the FGF-23 protein are known to be present, polypeptides of different molecular types derived from FGF-23 may be present in the same sample. Based on the fact that the antibodies used herein recognize specific sites of FGF-23, molecular types to be measured can be narrowed according to combinations of the antibodies. For example, when a combination is employed, where hFGF23-170 antibody are immobilized and detection is performed using hFGF23-25 antibody, since the antigen sites of both antibodies are contained in the N-terminal side partial polypeptide fragments between the $25^{th}$ and the $179^{th}$ residues of the amino acid sequence of the FGF-23 protein represented by SEQ ID NO: 1, it is predicted that not only the full-length polypeptide between the $25^{th}$ and the $251^{st}$ residues of SEQ ID NO: 1, but also the N-terminal partial polypeptide fragments, can be detected by the sandwich ELISA using this combination. On the other hand, when hFGF23-180 antibody is immobilized, and detection is performed using hFGF23-237 antibody, it is predicted that not only full-length polypeptides, but also a C-terminal partial polypeptide fragment corresponding to the $180^{th}$ to the $251^{st}$ residues of the FGF-23 protein represented by SEQ ID NO: 1, can be detected. Moreover, for example, when hFGF23-237 antibody is immobilized and detection is performed using hFGF23-25 antibody, it is predicted that only the full-length FGF-23 protein can be detected without detecting N- and C-terminal side partial polypeptides generated after cleavage. Therefore, the composite use of these combinations enables measurement of the absolute quantities of FGF-23 full-length polypeptides and partial polypeptides in analytes such as biological samples, and also enables the ability to distinguish existence ratios of these polypeptides.

TABLE 2

Detection of FGF-23 protein by sandwich ELISA using combinations of anti-FGF-23 polyclonal antibodies (A450 nm–A570 nm)

| Biotinylated antibodies | Immobilized antibodies | | | | | | | | |
|---|---|---|---|---|---|---|---|---|---|
| | hFGF23-25 | hFGF23-48 | hFGF23-114 | hFGF23-148 | hFGF23-170 | hFGF23-180 | hFGF23-210 | hFGF23-237 | None |
| hFGF23-25 | 0.517 | 0.046 | 0.040 | 0.050 | 1.543 | 1.938 | 0.686 | 1.808 | 0.048 |
| hFGF23-48 | 0.037 | 0.050 | 0.028 | 0.028 | 0.030 | 0.033 | 0.031 | 0.034 | 0.037 |
| hFGF23-114 | 0.033 | 0.026 | 0.029 | 0.026 | 0.027 | 0.029 | 0.026 | 0.029 | 0.036 |
| hFGF23-148 | 0.091 | 0.070 | 0.046 | 0.140 | 0.157 | 0.102 | 0.083 | 0.104 | 0.047 |
| hFGF23-170 | 0.444 | 0.035 | 0.033 | 0.068 | 0.112 | 0.054 | 0.041 | 0.057 | 0.042 |
| hFGF23-180 | 0.370 | 0.036 | 0.034 | 0.042 | 0.045 | 0.193 | 0.286 | 0.652 | 0.038 |
| hFGF23-210 | 0.309 | 0.034 | 0.033 | 0.036 | 0.043 | 0.563 | 0.065 | 0.383 | 0.035 |
| hFGF23-237 | 1.096 | 0.061 | 0.047 | 0.081 | 0.113 | 2.143 | 0.407 | 0.442 | 0.057 |

Types of immobilized antibodies are shown in the top horizontal line, and types of antibodies used for detection are shown in the leftmost column. Figures in this table are measured values obtained by the use of each combination.

(2) Quantitative Detection of FGF-23 Protein by Sandwich ELISA

Figure 2:
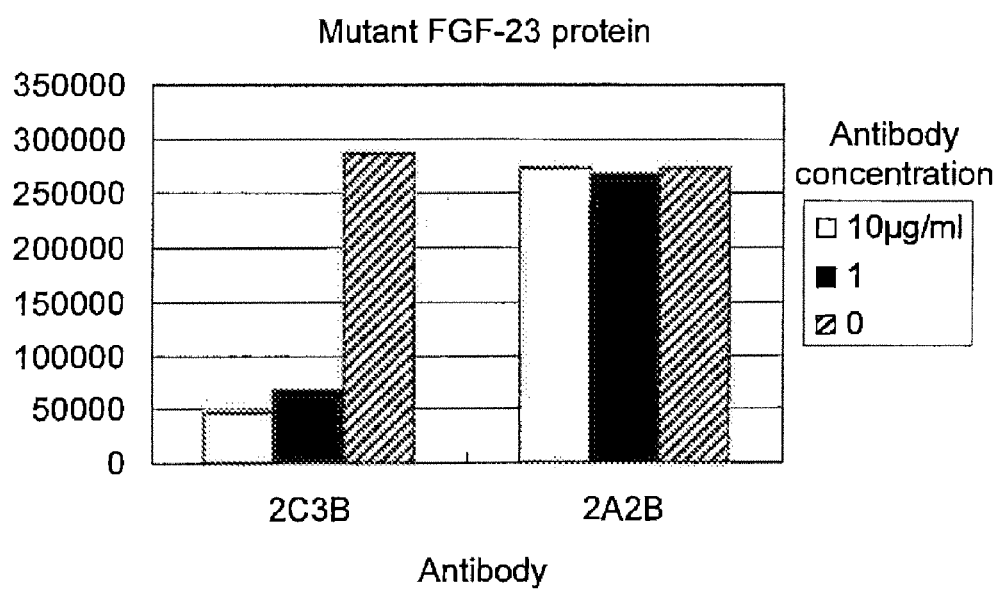
FIG. 2 shows the FGF-23H protein as measured by sandwich ELISA using an immobilized hFGF23-25 antibody, and an hFGF23-237 antibody as antibodies for detection, which are anti-FGF-23 polyclonal antibodies. (Example 7)

According to the above method for preparing the sandwich ELISA system, FGF-23H protein solutions having concentrations of 1, 0.33, 0.1, 0.033, 0.01, 0.0033, and 0.001 μg/ml, respectively, were measured as test substances by immobilizing hFGF23-25 antibody and using hFGF23-237 antibody for detection. The results are shown in FIG. 2. Within the range of 0.1 to 1 μg/ml, concentration-dependent increases were observed in values obtained by 450 nm-570 nm, revealing

Example 8

Preparation of FGF-23 Partial Peptide

In addition to the peptides corresponding to the FGF-23 partial sequences prepared in Example 5, peptides having the following partial sequences of FGF-23 were chemically synthesized:

An hFGF23-38 peptide (SEQ ID NO: 18) comprising 13 amino acid residues beginning from residue number 38 (glycine) of SEQ ID NO: 1 and having a cysteine residue added to the C-terminus of the peptide; an hFGF23-68 peptide (SEQ ID NO: 19) comprising 28 amino acid residues beginning from residue number 68 (threonine) of SEQ ID NO: 1; an hFGF23-96 peptide (SEQ ID NO: 20) comprising 18 amino acid residues beginning from residue number 96 (methionine) of SEQ ID NO: 1; an hFGF23-129 peptide (SEQ ID NO: 21) comprising 22 amino acid residues beginning from residue number 129 (serine) of SEQ ID NO: 1 and having a cysteine residue added to the C-terminus of the peptide; an hFGF23-161 peptide (SEQ ID NO: 22) comprising 13 amino acid residues beginning from residue number 161 (arginine) of SEQ ID NO: 1 and having a cysteine residue added to the C-terminus of the peptide; an hFGF23-197 peptide (SEQ ID NO: 23) comprising 16 amino acid residues beginning from residue number 197 (alanine) of SEQ ID NO: 1; and an hFGF23-220 peptide (SEQ ID NO: 24) comprising 24 amino acid residues beginning from residue number 220 (serine) of SEQ ID NO: 1.

```
hFGF23-38:
GLIHLYTATARNSC                  (SEQ ID NO: 18)

hFGF23-68:
TIYSALMIRSEDAGFVVITGVMSRRYLC    (SEQ ID NO: 19)

hFGF23-96:
MDFRGNIFGSHYFDPENC              (SEQ ID NO: 20)

hFGF23-129:
SPQYHFLVSLGRAKRAFLPGMNC         (SEQ ID NO: 21)

hFGF23-161:
RNEIPLIHFNTPIC                  (SEQ ID NO: 22)

hFGF23-197:
ARMTPAPASCSQELPS                (SEQ ID NO: 23)

hFGF23-220:
SDPLGVVRGGRVNTHAGGTGPEGC        (SEQ ID NO: 24)
```

Example 9

Determination of FGF-23 Recognition Region of Monoclonal Antibodies

The regions containing amino acid sequences recognized by anti-FGF-23 monoclonal antibodies were determined by examining reactivity with peptides containing the partial sequences of human FGF-23.

(1) Experiment 1: Binding with Immobilized Peptides

Peptides (SEQ ID NOS: 7 to 17) synthesized in Example 5 were diluted to a concentration of 1 µg/ml with a 50 mM sodium hydrogencarbonate solution. 50 µl of the solution was added per well of a 96-well plate for ELISA (Maxisorp (trademark), Nunc, U.S.A.), and then the solutions were incubated at 37° C. for 1 hour, so as to immobilize the FGF-23 partial peptides. Next, the solutions were removed, 50 µl of a blocking solution (Superblock (trademark), PIERCE, U.S.A.) was added per well, and then incubation was performed at room temperature for 60 minutes, thereby performing blocking. After the solutions were removed, 50 µl of the culture supernatant of the hybridomas obtained in Example 3 or an HT-containing DMEM medium as a control was added per well, and then the solutions were incubated at room temperature for 1 hour for binding with the FGF-23 partial peptides. After the end of antibody-binding reaction, the wells were washed three times with T-TBS. Subsequently, 50 µl of HRP-labeled goat anti-mouse IgG(H+L)-F(ab')2 diluted 3000-fold with T-TBS containing a 10% blocking solution (Blockace (trademark), (DAINIPPON PHARMACEUTICAL CO., LTD. Japan) was added per well, and then the solutions were incubated at room temperature for 30 minutes so as to result in binding with the secondary antibody. Each well was washed 3 times with T-TBS, 50 µl of tetramethylbenzidine (Denmark, DAKO), which was a peroxidase chromogenic substrate, was added per well, and this was followed by color development at room temperature for 3 minutes. Next, 50 µl of a 0.5 M sulfuric acid solution was added per well, so as to stop reaction. Measurement was conducted using a system for measuring absorbance for a 96-well plate (MTP-300, CORONA ELECTRIC CO., LTD., Japan), and values were obtained by subtracting absorbance at 570 nm from absorbance at 450 nm. In the case of the control where only the HT-containing DMEM medium had been added, all the values obtained by 450 nm-570 nm were 0.06 or less. However, clearly increased absorbances were observed in the cases where the culture supernatants of the hybridoams had been added and specific peptides had been immobilized. The results are shown in Table 3. The 2A2B antibody was bound to hFGF23-148 peptide of SEQ ID NO: 12. 1D6A showed binding with an hFGF23-237 peptide of SEQ ID NO: 17. Hence, it is concluded that an antibody produced by the 2A2B hybridoma binds to a region between the $148^{th}$ and the $163^{rd}$ amino acid residues of FGF-23 represented by SEQ ID NO: 1 or a part thereof. Moreover, 1C3H binds to a region between the $180^{th}$ and the $194^{th}$ amino acid residues of FGF-23 represented by SEQ ID NO: 1 or a part thereof, and 1D6A binds to a region between the $237^{th}$ and the $251^{st}$ amino acid residues of FGF-23 represented by SEQ ID NO: 1 or a part thereof.

TABLE 3

Reactivity of immobilized peptides having partial sequence of FGF-23 with antibody in the culture supernatant of monoclonal-antibody-producing hybridoma

| Culture supernatant | Immobilized peptides | | | | | | | |
|---|---|---|---|---|---|---|---|---|
| | hFGF23-25 | hFGF23-48 | hFGF23-114 | hFGF23-148 | hFGF23-170 | hFGF23-180 | hFGF23-210 | hFGF23-237 |
| 1C3H | 0.053 | 0.043 | 0.043 | 0.041 | 0.037 | 0.240 | 0.039 | 0.036 |
| 1D6A | 0.056 | 0.051 | 0.049 | 0.045 | 0.044 | 0.040 | 0.038 | 2.058 |

TABLE 3-continued

Reactivity of immobilized peptides having partial sequence of FGF-23 with antibody in the culture supernatant of monoclonal-antibody-producing hybridoma

| Culture supernatant | Immobilized peptides | | | | | | | |
|---|---|---|---|---|---|---|---|---|
| | hFGF23-25 | hFGF23-48 | hFGF23-114 | hFGF23-148 | hFGF23-170 | hFGF23-180 | hFGF23-210 | hFGF23-237 |
| 2A2B | 0.052 | 0.048 | 0.043 | 2.321 | 0.040 | 0.037 | 0.036 | 0.040 |
| 2C3B | 0.056 | 0.046 | 0.043 | 0.038 | 0.039 | 0.038 | 0.041 | 0.041 |
| Control | 0.059 | 0.047 | 0.048 | 0.051 | 0.043 | 0.044 | 0.045 | 0.043 |

(2) Experiment 2: Binding with Immobilized Peptides

For FGF-23, cleavage is observed between the $179^{th}$ and the $180^{th}$ amino acid residues of the sequence represented by SEQ ID NO: 1. For the purpose of examining in detail antibodies recognizing a region from the cleavage site to the C-terminal side, a binding experiment was conducted using synthetic peptides having sequences corresponding to parts of the region. Peptides (SEQ ID NOS: 14, 15, 16 and 17) synthesized in Example 5 and peptides (SEQ ID NOS: 23 and 24) synthesized in Example 8 were diluted to a concentration of 1 µg/ml with a 50 mM sodium hydrogencarbonate solution. 50 µl of the solution was added per well to a 96-well plate for ELISA (Maxisorp (trademark), Nunc, U.S.A.), and then the solutions were incubated at 4° C. for 12 hours for immobilization onto the plate. Next, the solutions were removed, 50 µl of a blocking solution (Superblock (trademark), PIERCE, U.S.A.) was added per well, and then incubation was performed at room temperature for 60 minutes, thereby performing blocking. After the solution was removed, 50 µl of a solution that had been prepared by diluting the 1D6A and 3C1E antibodies purified and obtained in Examples 3 and 4 with T-TBS containing 10% blocking solution (Blockace (trademark), (DAINIPPON PHARMACEUTICAL CO., LTD. Japan) to a concentration of 10 µg/ml was added per well. As a control, a well to which 50 µl of T-TBS containing a 10% blocking solution (Blockace (trademark), (DAINIPPON PHARMACEUTICAL CO., LTD. Japan) had been added was provided. The solutions were incubated at room temperature for 1 hour, thereby conducting a reaction of immobilized peptides with antibodies. After the end of the antibody reaction, the wells were washed 4 times with T-TBS, 50 µl of HRP-labeled goat anti-mouse IgG(H+L)-F(ab')2 diluted 3000-fold with T-TBS containing a 10% blocking solution (Blockace (trademark), (DAINIPPON PHARMACEUTICAL CO., LTD. Japan) was added per well. The solutions were incubated at room temperature for 60 minutes for reaction with the secondary antibody. After each well was washed 4 times with T-TBS, 50 µl of tetramethylbenzidine (Denmark, DAKO), which is a peroxidase chromogenic substrate, was added per well, followed by color development at room temperature for 20 minutes. 50 µl of a 0.5 M sulfuric acid solution was then added per well, so as to stop reaction.

Measurement was conducted using a system for measuring absorbance for a 96-well plate (MTP-300, CORONA ELECTRIC CO., LTD., Japan), and values were obtained by subtracting absorbance at 570 nm from absorbance at 450 nm. The results are shown in Table 4. In the case of the wells used as controls where only the solution for dilution had been added, all the values obtained by 450 nm-570 nm were 0.05 or less. In contrast, the 3C1E antibody was bound with hFGF23-180 peptide (SEQ ID NO: 15) and the 1D6A antibody was bound with hFGF23-237 peptides (SEQ ID NO: 17).

TABLE 4

Reactivity of immobilized peptides having partial sequence of FGF-23 with purified monoclonal antibodies

| Purified antibodies | Immobilized peptides | | | | | | | |
|---|---|---|---|---|---|---|---|---|
| | hFGF23-170 | hFGF23-174 | hFGF23-180 | hFGF23-197 | hFGF23-210 | hFGF23-220 | hFGF23-237 | Control |
| 1D6A | 0.041 | 0.051 | 0.047 | 0.050 | 0.055 | 0.054 | 3.412 | 0.060 |
| 3C1E | 0.037 | 0.043 | 0.203 | 0.041 | 0.040 | 0.051 | 0.042 | 0.045 |
| Control | 0.038 | 0.041 | 0.035 | 0.036 | 0.042 | 0.048 | 0.043 | 0.048 |

Example 10

Detection of FGF-23 Protein and Polypeptide Derived therefrom by Immunoprecipitation Immunoprecipitation was performed so that precipitated protein was detected by Western blotting in order to reveal the reactivity of the obtained monoclonal antibodies with the FGF-23 protein and polypeptides derived therefrom in a liquid phase that was closer to physiological conditions compared with immobilized peptides.

Figure 3:
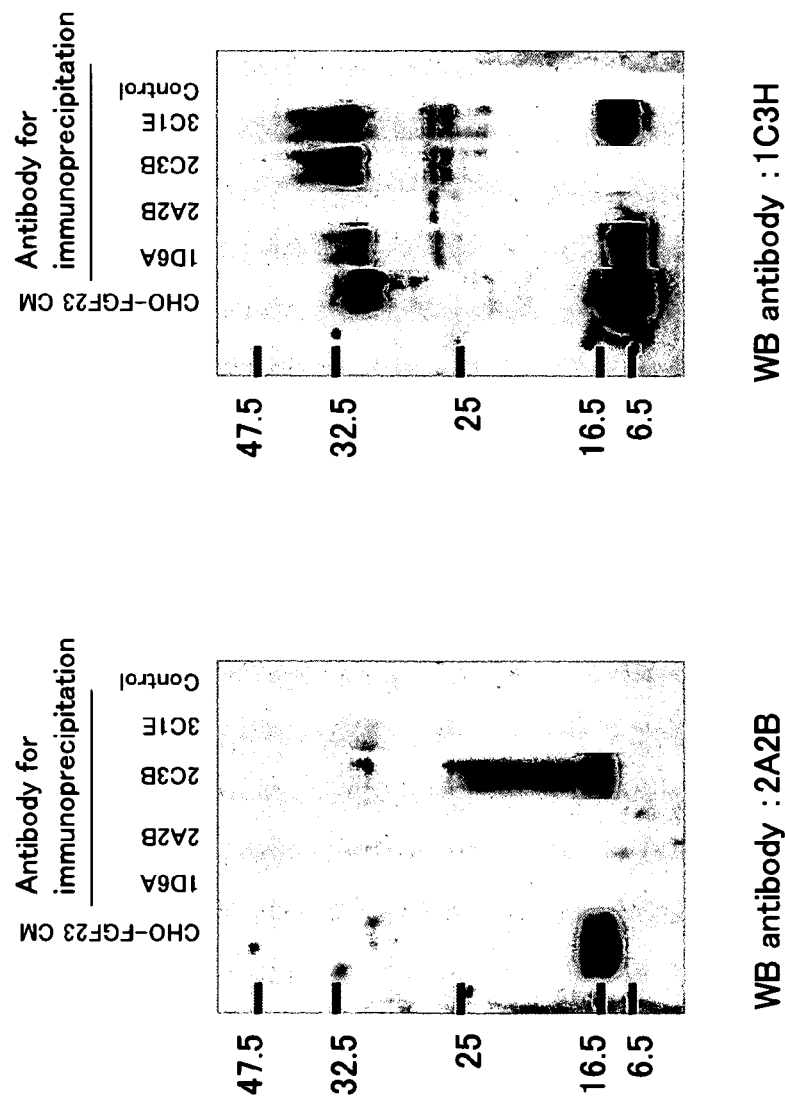
FIG. 3 shows the results as detected using 2A2B and 1C3H antibodies after immunoprecipitating the FGF-23H protein using anti-FGF-23 monoclonal antibodies, and separating the protein by SDS-polyacrylamide gel electrophoresis. (Example 10)

The CHO-FGF23 cells expressing FGF-23H prepared in Example 2 were cultured in CHO-S-SFM II media (Gibco BRL, U.S.A.) for 4 days, thereby obtaining the culture supernatant containing the FGF-23 protein, N-terminal side polypeptide fragments, and C-terminal side polypeptide fragments. 0.5 µg each of the 5 types of anti-FGF-23 monoclonal antibodies prepared in Examples 3 and 4 was added per 400 µl of the supernatant, so as to prepare solutions. A control solution was prepared by adding only a buffer. These solutions were admixed by being turned upside down at 4° C. for 1.5 hours so as to cause the antibodies to react with the protein in the culture supernatant. Subsequently, 30 µl of protein G Sepharose 4FF resins (Amersham Pharmacia Biotech, U.S.A.) was added, the solutions were admixed by being turned upside down at 4° C. for 3 hours, and then substances not bound to resins were washed off 3 times with PBS. To a half quantity of the resins, 30 µl of 20 mM DTT-containing buffer and 20 mM DTT-free sample buffer (50 mM Tris-Cl pH6.8, 1% SDS, 10% glycerol, 0.001% bromophenol blue, 2 mM EDTA) were added. The solutions were heated at 95° C. for 5 minutes and then centrifuged, thereby collecting supernatants. The thus collected immunoprecipitates were separated by 10% to 20% concentration-gradient polyacrylamide gel electrophoresis. Protein in the gel were transferred to an Immobilon PVDF membrane (Millipore, U.S.A.) using a Semi Dry Blotting System (Owl Separation Systems, U.S.A.). After blocking the PVDF membrane with a blocking solution (Blockace (trademark), (DAINIPPON PHARMACEUTICAL CO., LTD. Japan), incubation was performed at 4° C. for 12 hours in a solution of biotin-labeled 2A2B antibody or 1C3H antibodies that had been diluted to 1 μg/ml in T-TBS. Furthermore, HRP-labeled streptavidin (DAKO, Denmark) was allowed to react with the resultants. After washing, the resultant was exposed to a film using an ECL Plus luminescence system (Amersham Pharmacia Biotech, U.S.A.) for 1 hour, and then the film was developed using an automatic processor (FUJI PHOTO FILM CO., LTD., Japan). The results are shown in FIG. 3. The 2A2B antibody used in Western blotting recognizes a site corresponding to amino acid residue numbers 148 to 163 of SEQ ID NO: 1. Moreover, the 1C3H antibody used herein was shown to recognize a site corresponding to amino acid residue numbers 180 to 194 of SEQ ID NO: 1. By the use of both antibodies, fragmented polypeptides generated by cleavage between the $179^{th}$ and the $180^{th}$ amino acid residues can be distinguished from other polypeptides and recognized. As a result of this experiment, monoclonal antibodies were classified into the following 3 types. Specifically, these are: (1) 2 types of antibody (2C3B antibody and 2C5L antibody) having a recognition sequence within the N-terminal side fragment polypeptide corresponding to amino acid residue numbers 25 to 179 of SEQ ID NO: 1, or forming an immunocomplex with the N-terminal side fragment polypeptide and the FGF-23 full-length protein; (2) 2 types of antibody (1D6A antibody and 3C1E antibody) having a recognition sequence in the C-terminal side fragment polypeptide corresponding to amino acid residue numbers 180 to 251 of SEQ ID NO: 1, and forming an immunocomplex with the C-terminal side fragment polypeptide fragment and the FGF-23 full-length protein; and (3) an antibody (2A2B antibody) for which no immunoprecipitates were detected.

Example 11

Detection of FGF-23 Protein by ELISA Using Anti-FGF-23 Monoclonal Antibody and Anti-FGF-23 Polyclonal Antibody 2 types of monoclonal antibodies (1D6A antibody and 2C3B antibody) were separately immobilized, and then the purified FGF-23 protein was detected by a sandwich ELISA system using each of the 5 types of polyclonal antibodies (hFGF23-25 antibody, hFGF23-170 antibody, hFGF23-180 antibody, hFGF23-210 antibody, and hFGF23-237 antibody) whose usefulness as antibody for detection was shown in Example 7.

Figure 4:
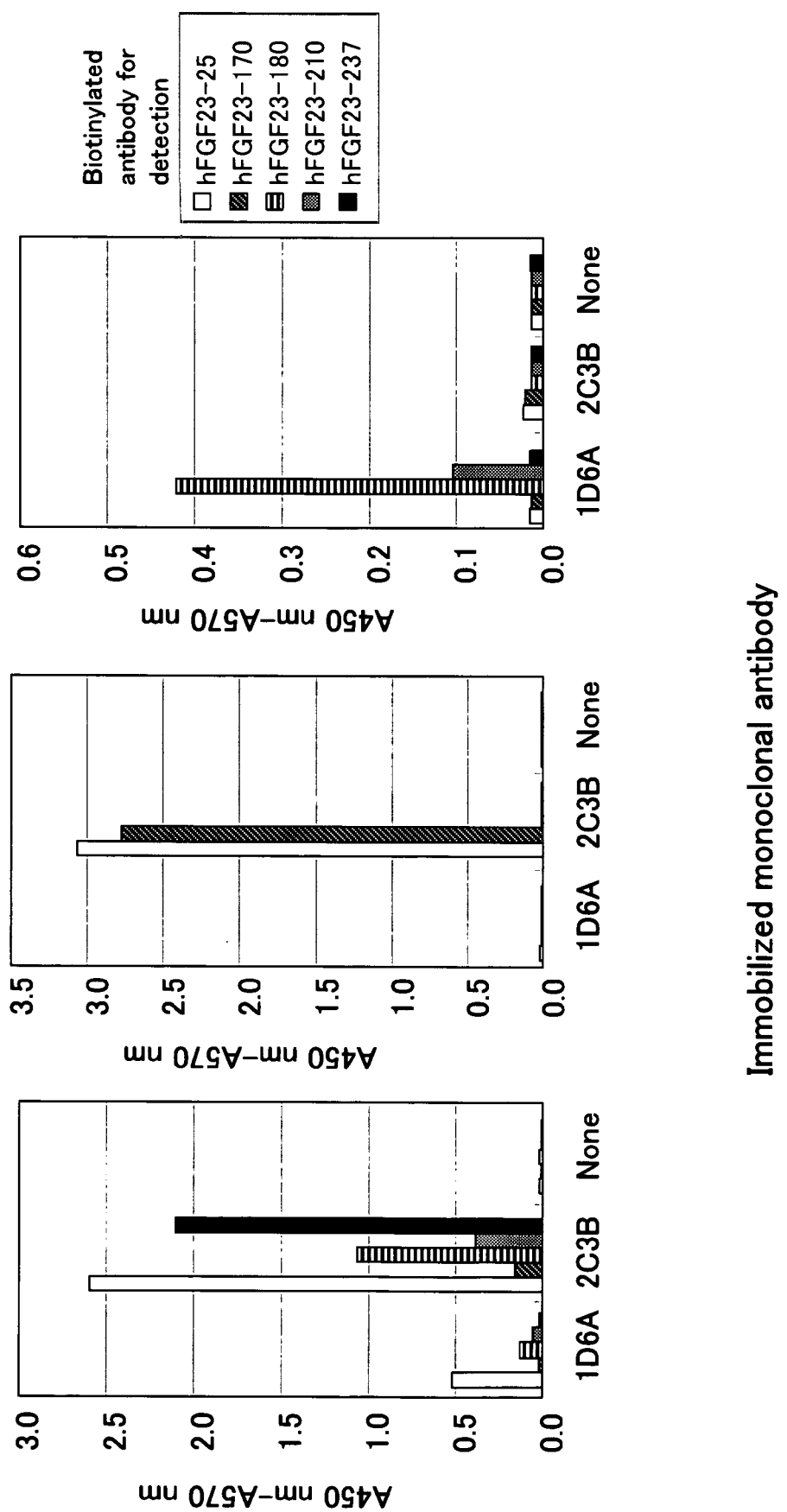
FIG. 4 shows the purified FGF-23H full-length protein, the N-terminal fragment polypeptide, and the C-terminal fragment polypeptide as detected by sandwich ELISA using immobilized anti-FGF-23 monoclonal antibodies and anti-FGF-23 polyclonal antibodies as antibodies for detection. (Example 11)
Figure 5:
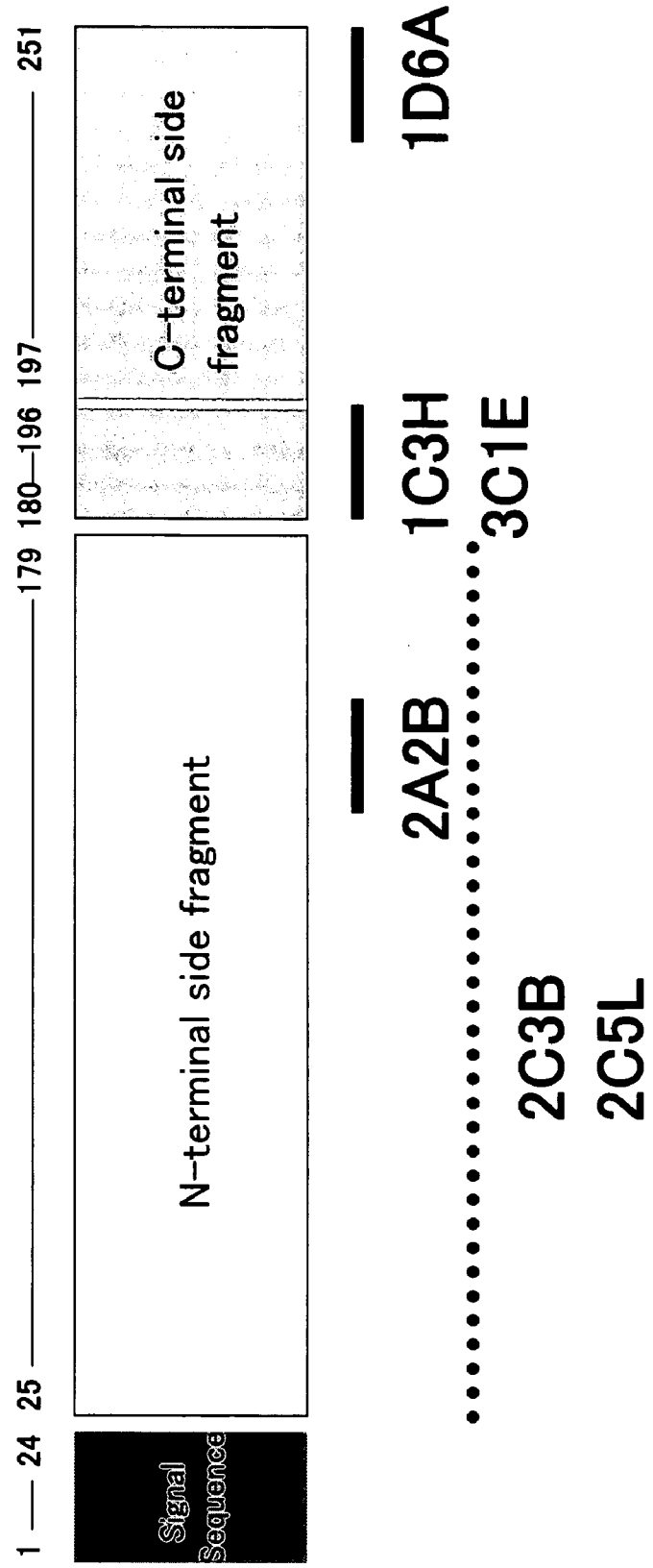
FIG. 5 schematically shows the full-length FGF-23 protein and the cleavage sites thereof, and the recognition sites of the anti-FGF-23 monoclonal antibodies. (Example 12)

The above 2 types of monoclonal antibodies purified with a protein G affinity column were diluted to 10 μg/ml with a 50 mM sodium hydrogen carbonate solution. 50 μl of the resultant solution was added per well of a 96-well plate for ELISA (Maxisorp (trademark), Nunc, U.S.A.), and then incubated at 37° C. for 1 hour for immobilization. Subsequently, the reaction solutions were removed, 50 μl of a blocking solution (SuperBlock (trademark), PIERCE, U.S.A.) was added per well, and the resultant was incubated at room temperature for 30 minutes, thereby performing blocking. After the solutions were removed, the wells were washed 3 times with PBS (T-PBS) containing 0.05% Tween 20. 50 μl of each solution of the purified FGF-23H protein, purified N-terminal side fragment polypeptide, or purified C-terminal side fragment polypeptide having an His6 tag added thereto, each having a concentration of 0.1 μg/ml, was added per well. The solutions were incubated at room temperature for 2 hours so as to react with the immobilized antibodies. After antibody reaction, the wells were washed 3 times with T-TBS. 5 types of biotin-labeled anti-FGF-23 partial peptide polyclonal antibodies (hFGF23-25 antibody, hFGF23-170 antibody, hFGF23-180 antibody, hFGF23-210 antibody, and hFGF23-237 antibody) diluted to 2.5 μg/ml with T-TBS containing a 10% blocking solution (Blockace (trademark), DAINIPPON PHARMACEUTICAL CO., LTD. Japan) were incubated at room temperature for 30 minutes, thereby conducting reaction with secondary antibodies. After each well was washed 3 times with T-TBS, 50 μl of HRP-labeled streptavidin (DAKO, Denmark) diluted 5000-fold with T-TBS containing a 10% blocking solution (Blockace (trademark), DAINIPPON PHARMACEUTICAL CO., LTD. Japan) was added per well. The solutions were incubated at room temperature for 30 minutes, so as to bind the streptavidin with biotin-labeled antibodies. Each well was washed 4 times with T-TBS, 50 μl of tetramethylbenzidine (DAKO, Denmark), which is a peroxidase chromogenic substrate, was added per well, followed by incubation at room temperature. 7 minutes later, 50 μl of 0.5 M sulfuric acid solution was added per well, so as to stop reaction. Measurement was conducted using a system for measuring absorbance for a 96-well plate (MTP-300, CORONA ELECTRIC CO., LTD., Japan), and values were obtained by subtracting absorbance at 570 nm from absorbance at 450 nm. The results are shown in FIG. 4. In the case of the control to which no antibodies had been added, all the values obtained by 450 nm-570 nm were 0.015 or less. However, depending on the combinations of the immobilized antibodies and the antibodies for detection, reactions specific to the FGF-23 full-length protein (FIG. 4A), N-terminal side fragment polypeptide (FIG. 4B), or the C-terminal side fragment polypeptide (FIG. 4C) were observed. Based on differences in reactivity, the recognition sites of the anti-FGF-23 monoclonal antibodies could be confirmed. Specifically, the full-length FGF-23 protein was detected in the case of using a combination of the 2C3B antibody as an immobilized antibody, and one of 3 types of biotinylated polyclonal antibodies (hFGF23-180 antibody, hFGF23-210 antibody, and hFGF23-237 antibody) as antibodies for detection. However, neither the N-terminal fragment polypeptide nor the C-terminal fragment polypeptide was detected. On the other hand, the full-length FGF-23 protein and the N-terminal side fragment polypeptide were detected strongly by the use of biotin-labeled polyclonal antibodies (hFGF23-25 antibody and hFGF23-170 antibody) recognizing the N-terminal fragment polypeptide, but no C-terminal fragment polypeptide was detected.

Thus, it was confirmed that the 2C3B antibody recognizes the N-terminal fragment polypeptide. When the 1D6A antibody was immobilized, the full-length protein was detected by the use of polyclonal antibodies as antibodies for detection recognizing the N-terminal fragment polypeptides. However, no N-terminal fragments and no C-terminal fragment polypeptides were detected. On the other hand, when the full-length protein and the C-terminal fragment polypeptides were detected using polyclonal antibodies recognizing the C-terminal fragment polypeptides as antibodies for detection, detection was possible with a combination of the 1D6A antibody with hFGF23-180. These results showed that the 1D6A antibody competes with the hFGF23-237 polyclonal antibody, so that it was confirmed that the 1D6A antibody recognizes a region between the 237$^{th}$ and the 251$^{st}$ amino acid residues of SEQ ID NO: 1.

Example 12

Detection of FGF-23 Protein by Sandwich ELISA Using Anti-FGF-23 Monoclonal Antibodies in Combination Purified FGF-23 protein was detected by performing sandwich ELISA using 4 immobilized types of anti-FGF-23 monoclonal antibodies obtained in Examples 3 and 4, and the 4 types of biotin-labeled anti-FGF-23 monoclonal antibodies prepared in Example 6 as antibodies for detection.

4 types of FGF-23 monoclonal antibodies 1D6A antibody, 2A2B antibody, 2C3B antibody, and 3C1E antibody) were diluted to 10 μg/ml with a 50 mM sodium hydrogen carbonate solution. 50 μl of the resultant solution was added per well of a 96-well plate for ELISA (Maxisorp (trademark), Nunc, U.S.A.), and then incubated at 4° C. for 12 hours for immobilization. Subsequently, the reaction solutions were removed and 50 μl of a blocking solution (SuperBlock (trademark), PIERCE, U.S.A.) was added per well. The resultant was incubated at room temperature for 20 minutes, thereby performing blocking. After the solutions were removed, the wells were washed 3 times with TBS containing 0.1% Tween 20(T-TBS). 50 μl of the purified FGF-23 protein at a concentration of 0.1 μg/ml was added per well. The solutions were incubated at room temperature for 1 hour so as to conduct reaction with the immobilized antibodies. After antibody reaction, the wells were washed 4 times with T-TBS. 3 types of biotin-labeled anti-FGF-23 monoclonal antibodies (1D6A antibody, 2C3B antibody, and 3C1E antibody) diluted at 10 μg/ml with T-TBS containing a 10% blocking solution (Blockace (trademark), DAINIPPON PHARMACEUTICAL CO., LTD. Japan) were added. The solutions were incubated at room temperature for 1 hour, so as to conduct secondary antibody reaction. After each well was washed 4 times with T-TBS, 50 μl of HRP-labeled streptavidin (DAKO, Denmark) diluted 5000-fold with T-TBS containing a 10% blocking solution (Blockace (trademark), DAINIPPON PHARMACEUTICAL CO., LTD. Japan) was added per well. The solutions were incubated at room temperature for 20 minutes, so as to bind the streptavidin with biotin-labeled antibodies. Each well was washed 4 times with T-TBS and 50 μl of tetramethylbenzidine (DAKO, Denmark), which is a peroxidase chromogenic substrate, was added per well, followed by incubation at room temperature. 30 minutes later, 50 μl of 0.5 M sulfuric acid solution was added per well, so as to stop reaction. Measurement was conducted using a system for measuring absorbance for a 96-well plate (MTP-300, CORONA ELECTRIC CO., LTD., Japan), and values were obtained by subtracting absorbance at 570 nm from absorbance at 450 nm. The results are shown in Table 6. In the case of the control to which immobilized antibodies or antibodies for detection had not been added, all the values obtained by 450 nm-570 nm were 0.033 or less. However, depending on the combinations of the immobilized antibodies and the antibodies for detection, increases were observed in absorbance. For example, when sandwich ELISA was performed using as an immobilized antibody the 2C3B antibody having a recognition site within the range between the 25$^{th}$ and the 179$^{th}$ amino acid residues in the amino acid sequence of the FGF-23 protein represented by SEQ ID NO: 1, and using as antibodies for detection the biotin-labeled 1D6A and 3C1E antibodies having recognition sites in the range between the 180$^{th}$ and the 251$^{st}$ amino acid residues in the amino acid sequence of the FGF-23 protein represented by SEQ ID NO: 1, all the values obtained by 450 nm-570 nm were as high as 2.9 or more. Fragmented polypeptides resulting from cleavage between the 179$^{th}$ arginine and the 180$^{th}$ serine of the amino acid sequence of the FGF-23 protein represented by SEQ ID NO: 1 are excluded from the subjects to be measured by sandwich ELISA in such a manner. Hence, by the use of such a combination of antibodies, uncleaved FGF-23 protein can be detected with high sensitivity without recognizing the N-terminal side polypeptide fragments or the C-terminal side polypeptide fragments. When the full-length FGF-23H protein, the N-terminal side polypeptide fragments, and the C-terminal side polypeptide fragments purified in Example 2 were administered to mice in a manner similar to those of previous reports, induction of decreases in serum phosphorus was observed only in the case of full-length FGF-23H protein. Thus, it was revealed that cleavage between the 179$^{th}$ arginine and the 180$^{th}$ serine of the amino acid sequence of the FGF-23 protein represented by SEQ ID NO: 1 greatly alters the activity of the FGF-23 protein. The method shown herein, which involves selectively detecting uncleaved FGF-23 protein while excluding cleaved polypeptides, enables more precise detection and measurement of FGF-23 contained within samples and having activity. On the other hand, when the 1D6A antibody and the 3C1E antibody having recognition sites in the region between the 180$^{th}$ and the 251$^{st}$ amino acid residues in the amino acid sequence of the FGF-23 protein represented by SEQ ID NO: 1 were used as immobilized antibodies, and the biotin-labeled 1D6A antibody and the 3C1E antibody were also used as antibodies for detection, it was similarly revealed by competition among the antibodies that the group of the 3C1E antibodies recognizing the region between the 180$^{th}$ and the 194$^{th}$ amino acid residues of the amino acid sequence represented by SEQ ID NO: 1 has a recognition site differing from that of the 1D6A antibody recognizing the region between the 237$^{th}$ and the 251$^{st}$ amino acid residues of the amino acid sequence represented by SEQ ID NO: 1. Furthermore, it was revealed that the use of these antibodies in combination enables establishment of a measurement method with which polypeptide fragments located within the region between the 25$^{th}$ and the 179$^{th}$ amino acid residues of the amino acid sequence represented by SEQ ID NO: 1 can be excluded, and C-terminal fragment polypeptides of the 180$^{th}$ to the 251$^{st}$ residues can be detected with good sensitivity.

TABLE 5

Absorbance obtained when FGF-23 protein was detected by sandwich ELISA using in combination anti-FGF-23 monoclonal antibodies and biotinylated antibodies thereof as immobilized antibodies and antibodies for detection, respectively

| Antibodies for detection | Immobilized antibodies | | | |
| --- | --- | --- | --- | --- |
| | 1D6A | 2C3B | 3C1E | None |
| 1D6A | 0.038 | 3.469 | 3.131 | 0.015 |
| 2C3B | 1.287 | 0.466 | >3.5 | 0.015 |
| 3C1E | 1.549 | >3.5 | 0.058 | 0.033 |
| None | 0.020 | 0.024 | 0.023 | 0.022 |

Example 13

Figure 6:
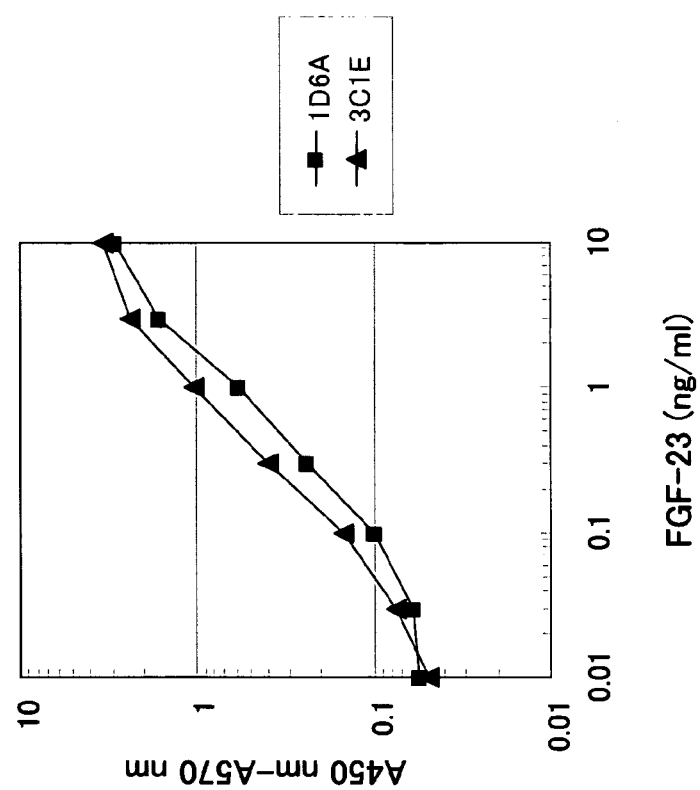
FIG. 6 shows the purified FGF-23 protein as quantitatively measured by the ELISA system using the 2C3B antibody as an immobilized antibody and the 1C3H, 1D6A, and 3C1E antibodies as antibodies for detection. (Example 13)

Quantitative Measurement of FGF-23 Protein by Sandwich ELISA Method Using Anti-FGF-23 Monoclonal Antibodies The 2C3B antibodies were diluted to 10 µg/ml with a 50 mM sodium hydrogen carbonate solution. 50 µl of the resultant solution was added per well of a 96-well plate for ELISA (Maxisorp (trademark), Nunc, U.S.A.), and then incubated at 4° C. for 12 hours for immobilization. Subsequently, the reaction solutions were removed, 250 µl of a blocking solution (SuperBlock (trademark), PIERCE, U.S.A.) was added per well and then the resultant was incubated at room temperature for 30 minutes, thereby performing blocking. After the solutions were removed, the wells were washed 2 times with TBS (T-PBS) containing 0.1% Tween 20. A solution was prepared by diluting the FGF-23 protein purified in Example 2 at 10, 3, 1, 0.3, 0.1, 0.03, 0.01, or 0.003 ng/ml with T-TBS containing a 10% blocking solution (Blockace (trademark), DAINIPPON PHARMACEUTICAL CO., LTD. Japan). 50 µl of each solution was added per well. The solutions were incubated at room temperature for 1 hour, so that reaction with immobilized antibodies was conducted. After antibody reaction, the wells were washed 4 times with T-TBS, and then 2 types of biotin-labeled anti-FGF-23 monoclonal antibodies (1D6A antibody and 3C1E antibody) diluted at 10 µg/ml with T-TBS containing a 10% blocking solution (Blockace (trademark), DAINIPPON PHARMACEUTICAL CO., LTD. Japan) were added. The solutions were incubated at room temperature for 30 minutes, thereby performing secondary antibody reaction. After each well was washed 4 times with T-TBS, 50 µl of HRP-labeled streptavidin (DAKO, Denmark) diluted 5000-fold with T-TBS containing a 10% blocking solution (Blockace (trademark), DAINIPPON PHARMACEUTICAL CO., LTD. Japan) was added per well. The solutions were incubated at room temperature for 30 minutes, so as to bind the streptavidin with biotin-labeled antibodies. Each well was washed 4 times with T-TBS, and then 50 µl of tetramethylbenzidine (DAKO, Denmark), which is a peroxidase chromogenic substrate, was added per well, followed by incubation at room temperature. 25 minutes later, 50 µl of 0.5 M sulfuric acid solution was added per well, so as to stop reaction. Measurement was conducted using a system for measuring absorbance for a 96-well plate (MTP-300, CORONA ELECTRIC CO., LTD., Japan), and values were obtained by subtracting absorbance at 570 nm from absorbance at 450 nm. The results are shown in FIG. 6. Because of the presence of the FGF-23 protein at a concentration of at least 0.03 ng/ml, significant increases in measured values were observed, and within the concentration ranging from 0.03 to approximately 3 ng/ml, concentration-dependent increases in values obtained by 450 nm-570 nm were obtained, revealing that the FGF-23 protein within this concentration range can be detected.

Example 14

Preparation of Anti-FGF-23 Monoclonal Antibody-Immobilized Column

A column immobilized anti-FGF-23 antibodies thereto was prepared using a commercial immobilization reagent (SulfoLink (trademark), PIERCE, U.S.A.), which is useful as an antibody column for collecting the FGF-23 protein by immunoprecipitation or purifying the FGF-23 protein. 1C3H antibody, 1D6A antibody, and 2C3B antibody were diluted in a 0.1 M phosphate buffer (pH 6.0) containing 5 mM EDTA, thereby preparing solutions at concentrations of 1 mg/ml, 1 mg/ml, and 0.4 mg/ml, respectively. To 1 ml of the antibody solution, 6 mg of 2-mercaptoethanol amine was added, the solution was admixed by being turned upside down at 37° C. for 1 hour, and then disulfide bonds within the antibodies were cleaved by reduction reaction. While the buffer was exchanged with 1.5 ml of a binding buffer (50 mM Tris/HCl, pH 8.5, 5 mM EDTA) solution using an NAP 10 column (Amersham Pharmacia Biotech, U.S.A.), 2-mercaptoethanol amine was removed to stop reduction reaction. These antibody solutions were added to 1 ml of SulfoLink (trademark) coupling gel (PIERCE, U.S.A.) that had been previously washed with a binding buffer. The solutions were admixed by being turned upside down at room temperature for 30 minutes, thereby conducting binding reaction. After centrifugation, resins were washed with a binding buffer. To perform blocking of unreacted thiol groups, 1 mL of a 0.05 mM L-cysteine-HCl solution was added, and then the solutions were admixed by being turned upside down at room temperature for 30 minutes. Subsequently, resins were washed with 1 M NaCl, so as to remove unreacted antibodies and L-cysteine.

Example 15

Detection of FGF-23 Protein Existing in the Serum of CHO-FGF23H Cell-Transplanted Mouse by Immunoprecipitation Method To examine the state of presence of the FGF-23 protein in blood, cells expressing FGF-23H were transplanted into nude mice, and then the FGF-23H protein secreted from these cells into blood were detected by an immunoprecipitation method. $2 \times 10^7$ CHO-FGF-23H cells, or CHO ras clone-1 cells as a control were transplanted subcutaneously into each Balb/c nude mouse. On day 32 after transplantation, sera were collected from mice wherein the cells had adhered successfully so as to form tumors. The serum collected from 5 CHO-ras clone-1-transplanted mice, and the serum collected from 6 CHO-FGF23H-transplantated mice were separately mixed in an equivalent volume. To 150 µl of each mixed serum, 10 µl each of resins prepared in Example 14 to which the 1D6A antibody had been immobilized, resins prepared in Example 14 to which the 2C3B antibody had been immobilized, and resins to which no antibodies had been immobilized were added. The resultants were admixed by being turned upside down at 4° C. for 1 hour, thereby performing reaction of the antibodies with FGF-23. The resins were washed 3 times with PBS, so that unreacted products were removed. 50 µl of a sample buffer (50 mM Tris-Cl pH6.8, 1% SDS, 10% glycerol, 0.001% bromophenol blue, 2 mM EDTA, and 20 mM DTT) was added to each of the resins. The resultants were heated at 95° C. for 5 minutes, and then subjected to centrifugation. The thus obtained supernatants were collected. The supernatants were separated by 10%-20% gradient polyacrylamide gel electrophoresis, and then protein in gel was transferred to PVDF membranes (Millipore, U.S.A.) using a Semi Dry Blotting System (Owl Separation Systems, U.S.A.). The PVDF membrane was incubated at 4° C. for 12 hours in a solution of biotin-labeled 2A2B antibodies or 1C3H antibodies that had been diluted at 0.5 µg/ml in Blockace (trademark) (DAINIPPON PHARMACEUTICAL CO., LTD. Japan). Furthermore, HRP-labeled streptavidin (DAKO, Denmark) was allowed to react with the resultants. The resultants were exposed to film using an ECL Plus luminescence system (Amersham Pharmacia Biotech, U.S.A.) for 1 hour, and then the film was developed using an automatic processor (FUJI PHOTO FILM CO., LTD., Japan). The results are shown in FIG. 7. For the resins to which no antibodies had been immobilized, no signals were observed at all. However, when immunoprecipitation using the 1C3H antibody and detection using the 2A2B antibody had been conducted, a signal of 22 kDa was detected. When detection had been conducted using the 1C3H antibody, signals of 22 kDa and 10 kDa were detected. In addition, when immunoprecipitation using the 1D6A antibody and detection using the 2A2B antibody had been conducted, a signal of 22 kDa was not detected, and when detection had been conducted using the 1C3H antibody, a signal of only 10 kDa was detected. Furthermore, when immunoprecipitation using the 2C3B antibody and detection using the 2A2B antibody had been conducted, signals of 22 kDa and 16 kDa were detected, and when detection had been conducted using the 1C3H antibody, a signal of only 22 kDa was detected. It has been shown that the 2A2B antibody recognizes the region between the $148^{th}$ and the $163^{rd}$ amino acid residues of SEQ ID NO: 1, and that the 1C3H antibody recognizes the region between the $180^{th}$ and the $194^{th}$ amino acid residues of SEQ ID NO: 1. Moreover, it has been shown that the 2A2B antibody recognizes the N-terminal side fragment polypeptide corresponding to the $25^{th}$ and the $179^{th}$ amino acid residues of SEQ ID NO: 1 as measured by the Western blotting method, and that the signal size is 16 kDa as detected by electrophoresis. It has also been shown that the 1C3H antibody recognizes the C-terminal side fragment polypeptide between the $180^{th}$ and the $251^{st}$ amino acid residues of SEQ ID NO: 1, and that the signal size detected is 10 kDa. Thus, it is clear that the signal of 16 kDa detected in this experiment indicates the N-terminal side fragment polypeptide, and the signal of 10 kDa detected in the same indicates the C-terminal side fragment polypeptide. In addition, the polypeptide of 22 kDa collected from the mouse serum can be recognized by the 2C3B antibody recognizing the N-terminal side region represented by the $25^{th}$ to the $179^{th}$ amino acid residues, the 2A2B antibody recognizing the region between the $148^{th}$ and the $163^{rd}$ amino acid residues, and the antibody produced by 1C3H recognizing the region between the $180^{th}$ and the $194^{th}$ amino acid residues, but cannot be recognized by the 1D6A antibody recognizing the region between $237^{th}$ and the $251^{st}$ amino acid residues of SEQ ID NO: 1. The signals of around 22 kDa observed in this experiment may be generated by the cleavage of the FGF-23 protein, and the cleavage site is present at the C-terminal side from the region that the 1C3H antibody recognizes. It was revealed that cleavages and fragments generated therefrom differing from cleavage between amino acid numbers 179th arginine and 180th serine represented by SEQ ID NO: 1, which we had paid attention to, were observed in serum.

Example 16

Figure 8:
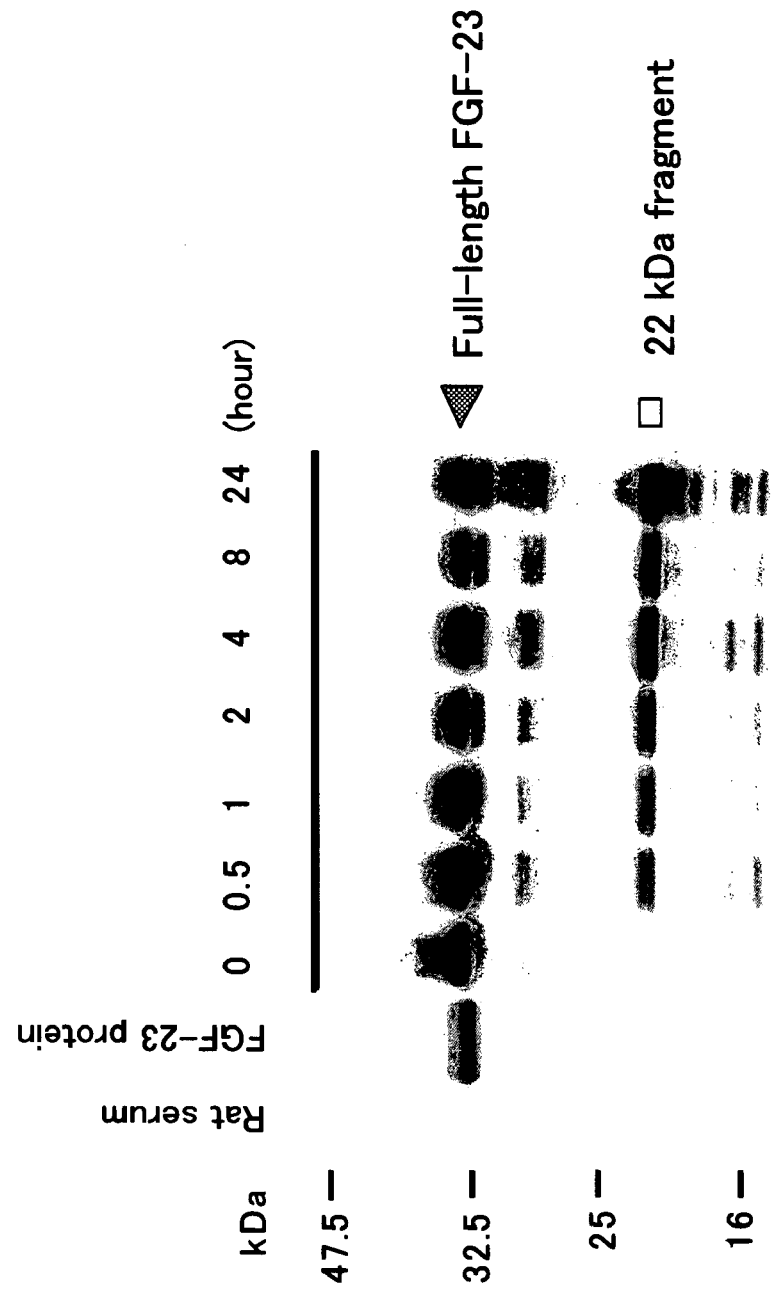
FIG. 8 shows the results as detected by Western blotting using the 2A2B antibody after adding rat serum to 20 ng of purified FGF-23 protein to result in a final concentration of 50%, admixing the resultant, and then separating metabolites generated by 0, 0.5, 1, 2, 4, 8, or 24 hours of incubation by SDS-polyacrylamide gel electrophoresis. (Example 16)

Cleavage of FGF-23 Protein in Serum (1) Admixture Experiment of Rat Serum and Purified FGF-23 Protein Cleavage of the FGF-23 protein by serum was examined by admixturing purified FGF-23 protein with rat serum. Rat serum was added at a final concentration of 50% to 20 ng of purified FGF-23 protein. The solutions were admixed and incubated for 0, 0.5, 1, 2, 4, 8, and 24 hours. The solutions were separated by polyacrylamide electrophoresis, and then protein in gel was transferred to PVDF membranes (Millipore, U.S.A.) using a Semi Dry Blotting System (Owl Separation Systems, U.S.A.). Western blotting was performed using the 2A2B antibody, so as to detect metabolites derived from purified FGF-23 protein. The results are shown in FIG. 8. After admixturing with serum, the quantity of the full-length FGF-23 protein existing in the solution decreased as the incubation time increased, and the appearance and increase of new fragments of 22 kDa were observed.

(2) Admixture Experiment of Human Serum or Plasma with Purified FGF-23 Protein

Figure 9:
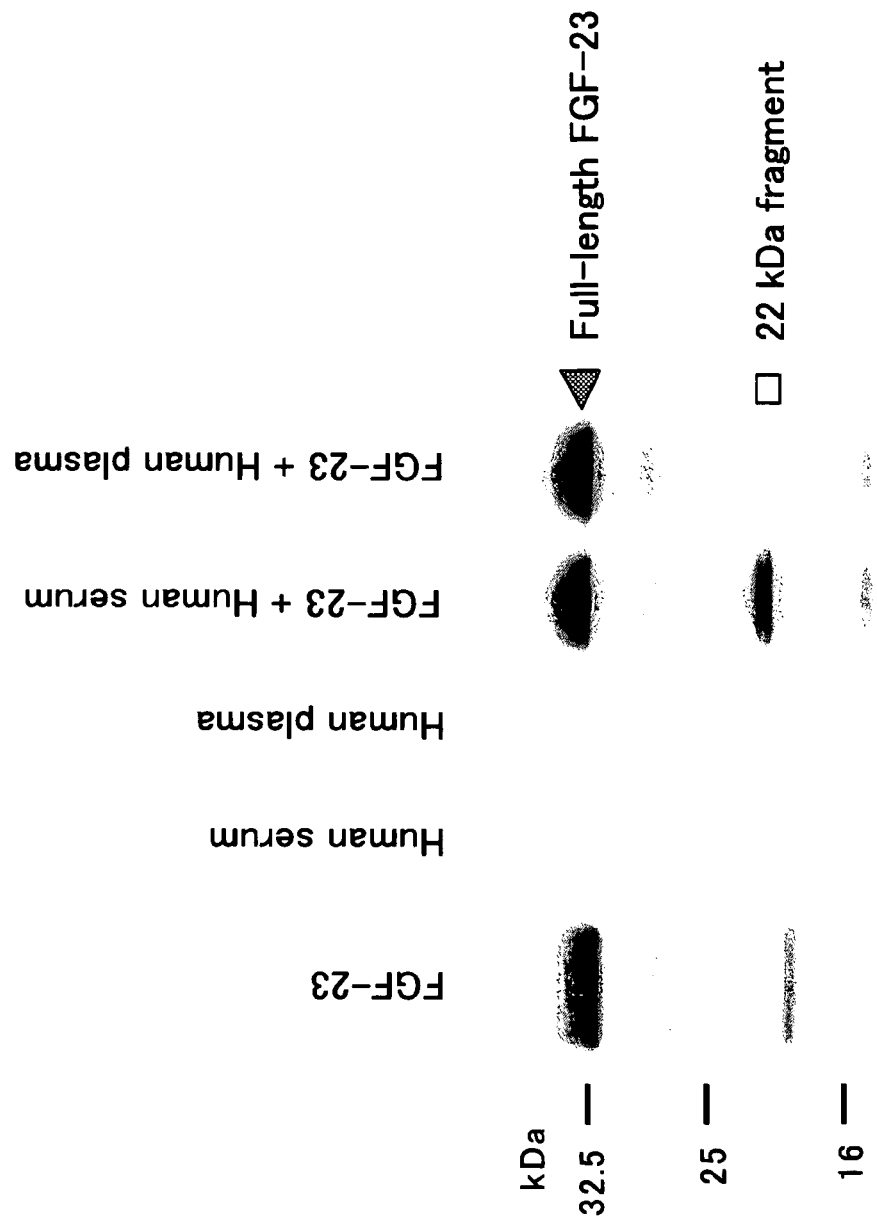
FIG. 9 shows metabolites derived from the purified FGF-23 protein as detected by Western blotting using the 2A2B antibody after adding human serum or human plasma to 20 ng of the purified FGF-23 protein to result in a final concentration of 50%, performing incubation at 37° C. for 3 hours, and performing separation by SDS-polyacrylamide gel electrophoresis. (Example 16)

Human serum or human plasma was added at a final concentration of 50% to 20 ng of purified FGF-23 protein, followed by incubation at 37° C. for 3 hours. The solutions were separated by polyacrylamide electrophoresis, and then protein in gel was transferred to PVDF membranes (Millipore, U.S.A.) using a Semi Dry Blotting System (Owl Separation Systems, U.S.A.). Western blotting was performed using the 2A2B antibody, so as to detect metabolites derived from purified FGF-23 protein. The results are shown in FIG. 9. When human serum and the FGF-23 protein were mixed, a band of 22 kDa appeared. However, when human plasma and the FGF-23 protein were mixed, a band of 22 kDa was not observed. Therefore, the band of 22 kDa was assumed to result from protein cleavage enzymes existing in the serum.

Example 17

Figure 10:
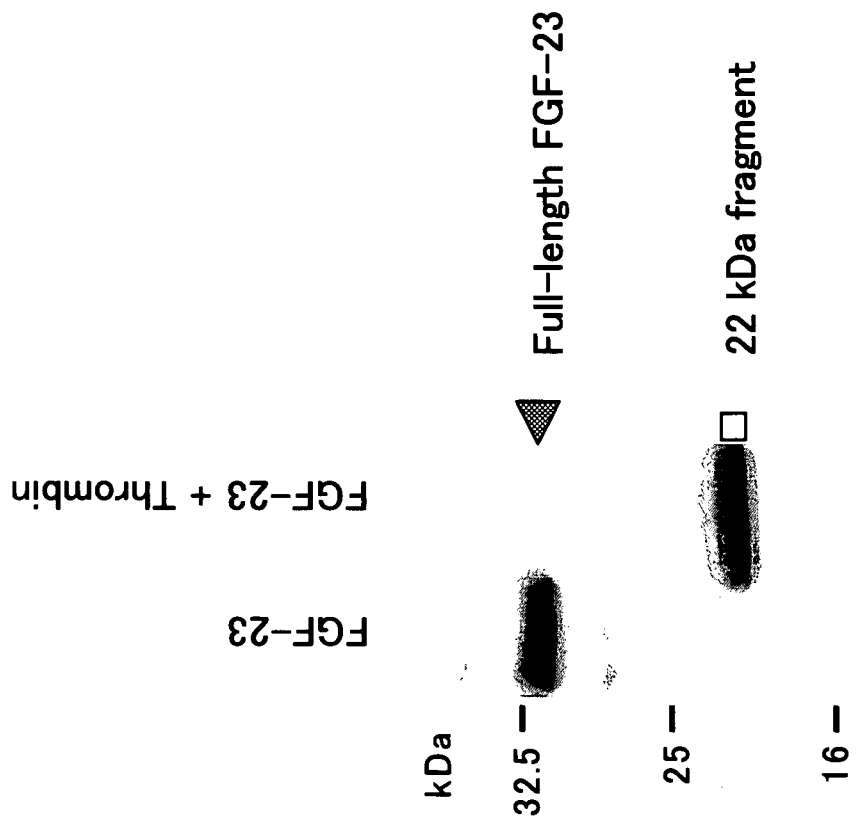
FIG. 10 shows metabolites derived from the purified FGF-23 protein as detected by Western blotting using the 2A2B antibody after adding thrombin to 20 ng of purified FGF-23 protein at a final concentration of 1 unit/ml, performing incubation for 3 hours, and then subjecting the solution to SDS-polyacrylamide gel electrophoresis for separation. (Example 17)

Identification of Enzyme Cleaving FGF-23 Protein (1) Cleavage of FGF-23 by Thrombin Thrombin (Sigma, U.S.A.) was added at a final concentration of 1 unit/ml to 20 ng of purified FGF-23 protein, followed by 3 hours of incubation. The solution was separated by polyacrylamide electrophoresis, and then protein in gel was transferred to a PVDF membrane (Millipore, U.S.A.) using a Semi Dry Blotting System (Owl Separation Systems, U.S.A.). Western blotting was performed using the 2A2B antibody, so as to detect metabolites derived from purified FGF-23 protein. The results are shown in FIG. 10. The full-length FGF-23 protein disappeared, and the band thereof was converted to a band of 22 kDa.

(2) Action of Hirudine to Inhibit Cleavage of FGF-23 Protein by Serum

Figure 11:
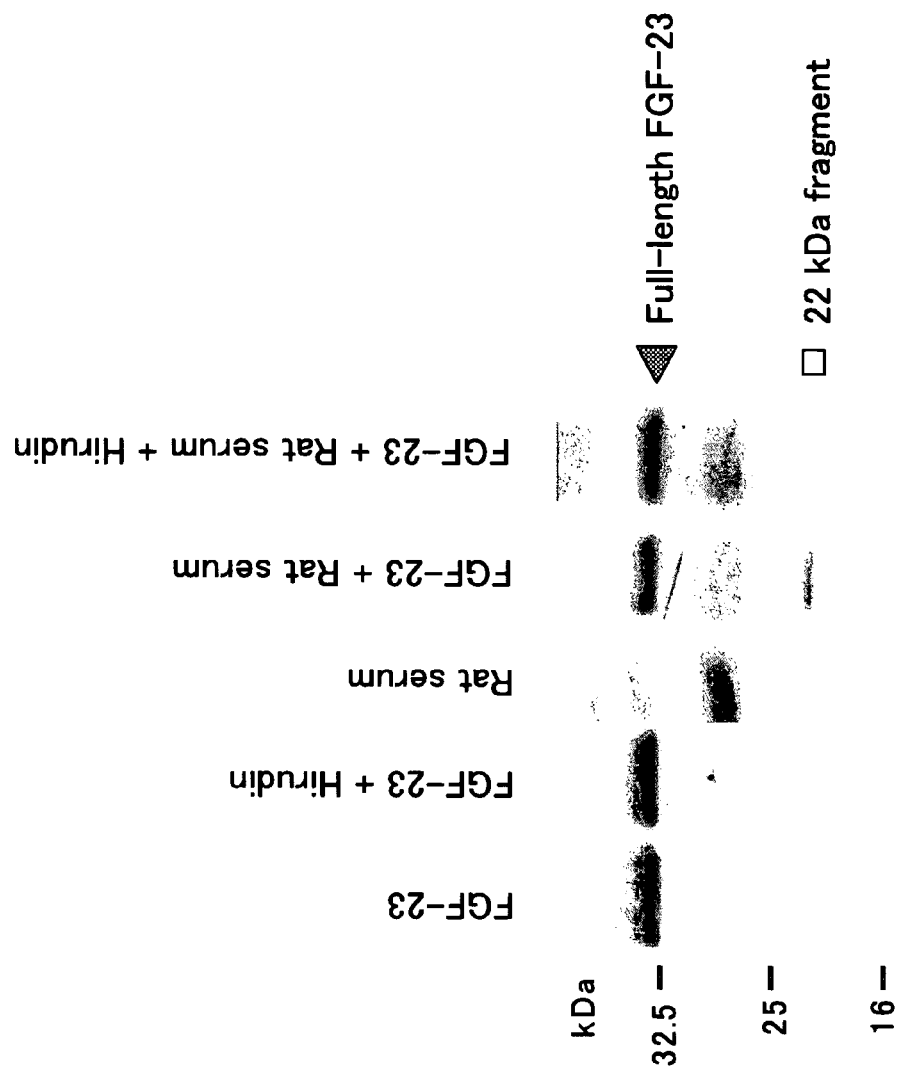
FIG. 11 shows metabolites derived from the purified FGF-23 protein as detected by Western blotting using the 2A2B antibody after adding rat serum to 20 ng of purified FGF-23 protein in the presence or the absence of hirudine, a thrombin selective inhibitor, at a final concentration of 50%, performing incubation for 4 hours, and then performing separation by SDS-polyacrylamide gel electrophoresis. (Example 17)

For the purpose of examining the involvement of thrombin in serum in cleavage of FGF-23 by serum, the effect of hirudine, which is known as a thrombin selective inhibitor, was examined. Rat serum was added at a final concentration of 50% to 20 ng of purified FGF-23 protein, followed by 4 hours of incubation. Furthermore, at the time of addition of rat serum, hirudine was added at 1.0 unit/ml, followed by incubation similarly. The solution was separated by polyacrylamide electrophoresis, and then protein in gel was transferred to a PVDF membrane (Millipore, U.S.A.) using a Semi Dry Blotting System (Owl Separation Systems, U.S.A.). Western blotting was performed using the 2A2B antibody, so as to detect metabolites derived from purified FGF-23 protein. The results are shown in FIG. 11. By the addition of rat serum, some of the FGF-23 proteins were converted into polypeptides of 22 kDa, and co-existence with hirudine suppressed the appearance of a band of 22 kDa. Thus, it was shown that the cleavage of the FGF-23 protein generated by serum is due to thrombin or enzymes analogous thereto.

Example 18

Identification of Cleavage Site of FGF-23 Protein by Serum

Figure 12:
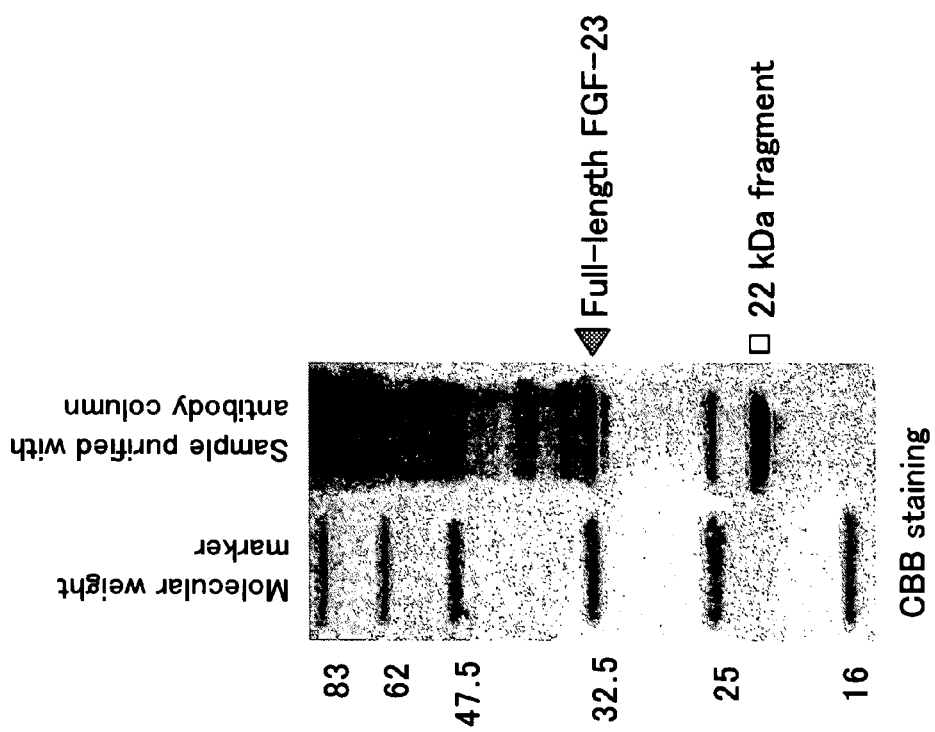
FIG. 12 shows a polypeptide of 22 kDa as identified by CBB staining after admixing 10 μg of purified FGF-23 protein and rat serum for 24 hours to generate the polypeptide of 22 kDa, purifying the polypeptide of 22 kDa using an anti-2A2B antibody column, and then performing separation by SDS-polyacrylamide gel electrophoresis. (Example 18)

To identify the cleavage site of FGF-23 generated by serum, 10 μg of purified FGF-23 protein and rat serum were admixed for 24 hours, thereby generating polypeptides of 22 kDa. The polypeptides of 22 kDa in this solution were adsorbed to the anti-1C3H antibody column prepared in Example 14, eluted, and purified. The antibody column used herein had been prepared by adsorbing 200 μg of biotinylated 1C3H antibodies on 500 μl of streptavidin-immobilized resins (Amersham Pharmacia Biotech, U.S.A.). The FGF-23-derived protein was eluted from the antibody column using a 0.1 M glycine solution (pH 2.7). The thus purified polypeptides were separated by SDS-polyacrylamide gel electrophoresis and stained by CBB staining, so that the purified polypeptide of 22 kDa was identified as shown in FIG. 12. This band was excised and subjected to MALDI-TOF MS analysis. Based on the molecular weight obtained from this analysis, the polypeptide of 22 kDa was shown to have a sequence ranging from the $25^{th}$ tyrosine to the $196^{th}$ arginine of the amino acid sequence represented by SEQ ID NO: 1.

These results revealed that in serum, the FGF-23 protein is cleaved at a position following the $196^{th}$ arginine of the amino acid sequence represented by SEQ ID NO: 1 by thrombin contained in serum, and then converted to a polypeptide represented by a sequence between the $25^{th}$ and the $196^{th}$ amino acid residues of SEQ ID NO: 1. As described above, measurement of FGF-23 protein having activity in blood requires detection of polypeptides uncleaved between the $179^{th}$ and the $180^{th}$ amino acid residues of the amino acid sequence of SEQ ID NO: 1. It was shown that the full-length FGF-23 protein having activity is partially cleaved between the $196^{th}$ and the $197^{th}$ amino acid residues during the process of the preparation of a serum sample, and the anti-FGF-23 monoclonal antibody that recognizes the C-terminus cannot recognize the metabolite thereof. Specifically, when sandwich ELISA was conducted using a combination of an antibody recognizing the region between the $25^{th}$ and the $179^{th}$ amino acid residues of the amino acid sequence of SEQ ID NO: 1, and an antibody recognizing the region between the $180^{th}$ and the $196^{th}$ amino acid residues of the amino acid sequence of SEQ ID NO: 1, the effect of cleavage resulting from serum preparation can be ignored. However, when an antibody recognizing the region between the $25^{th}$ and the $179^{th}$ amino acid residues of the amino acid sequence of SEQ ID NO: 1, and an antibody recognizing the region between the $197^{th}$ and the $251^{st}$ amino acid residues of the amino acid sequence of SEQ ID NO: 1 were used, measured values in serum may decrease compared with those in plasma. Among the anti-FGF-23 monoclonal antibodies obtained herein, the 1C3H antibody and the 3C1E antibody recognize the region between the $180^{th}$ and the $194^{th}$ amino acid residues of the amino acid sequence represented by SEQ ID NO: 1. Thus, a 22 kDa protein (corresponding to the $25^{th}$ and the $196^{th}$ amino acid residues of the amino acid sequence of SEQ ID NO: 1) produced by the cleavage of FGF-23 in serum can be recognized, as distinct from polypeptide fragments generated by the cleavage between the $179^{th}$ and the $180^{th}$ amino acid residues of the amino acid sequence of SEQ ID NO: 1. Thus, it was revealed that these antibodies are very useful in producing a method for measuring serum samples.

Example 19

Quantitative Analysis of FGF-23 Protein Concentrations in Serum and Plasma of Patients with Tumor-Induced Osteomalacia It has been reported that in tumor-induced osteomalacia, FGF-23 is excessively produced in tumors, and it is known that the disease is cured by removing the causative tumors. However, the causative tumor of tumor-induced osteomalacia is generally small because of its low growth ability and is often difficult to discern. Thus, diagnosis differentiating between tumor-induced osteomalacia and other hypophosphatemic diseases is difficult. Thus, if it can be demonstrated that blood FGF-23 concentrations can be an indicator for diagnosing tumor-induced osteomalacia, and a method by which the blood FGF-23 concentrations can be quantitatively measured is developed, such a method is clinically useful.

Figure 13:
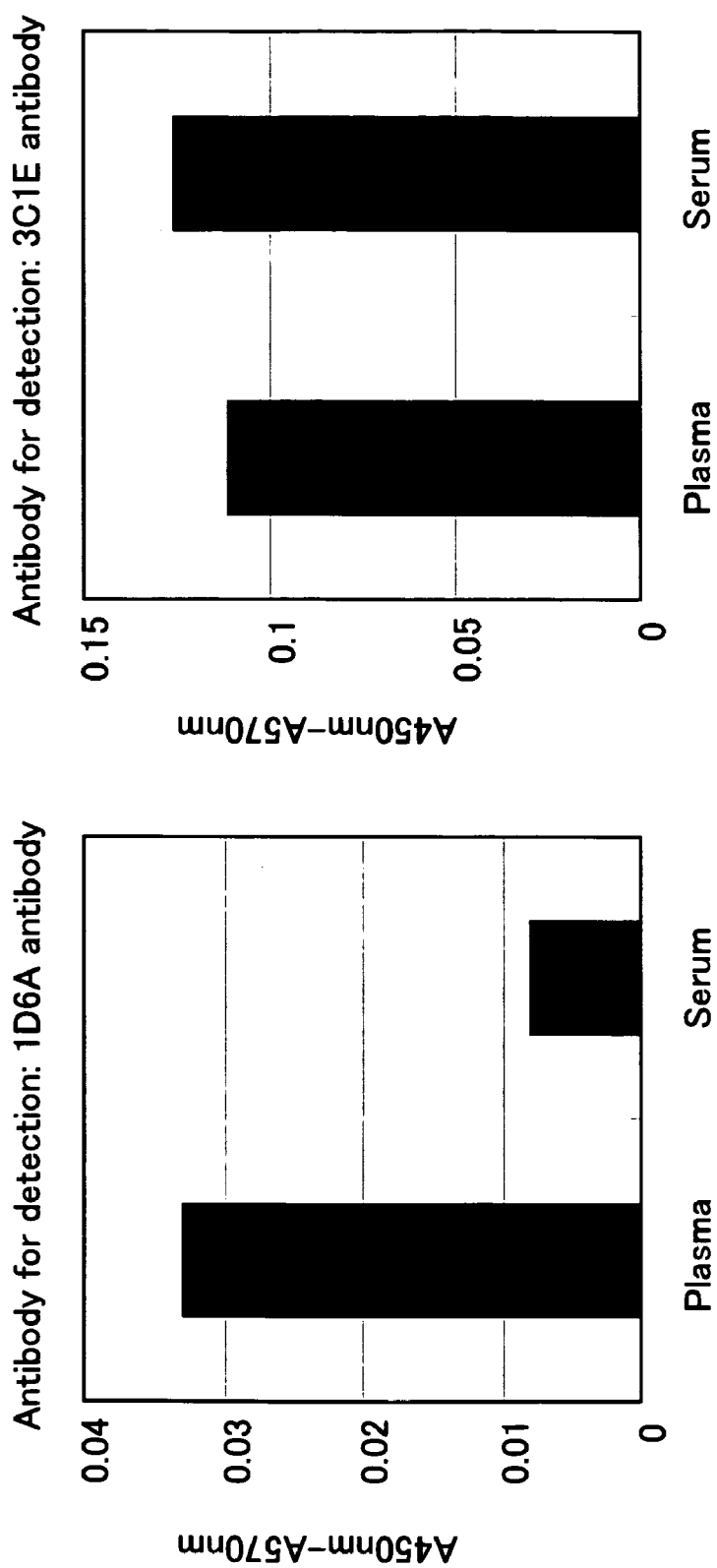
FIG. 13 shows the FGF-23 protein in blood samples collected before and after extraction of causative tumors of patients with neoplastic osteomalacia, as measured by the ELISA system whereby detection was performed using the 2C3B antibody as an immobilized antibody, and the 3C1E or the 1D6A antibody as an antibody for detection. (Example 19)
Figure 14:
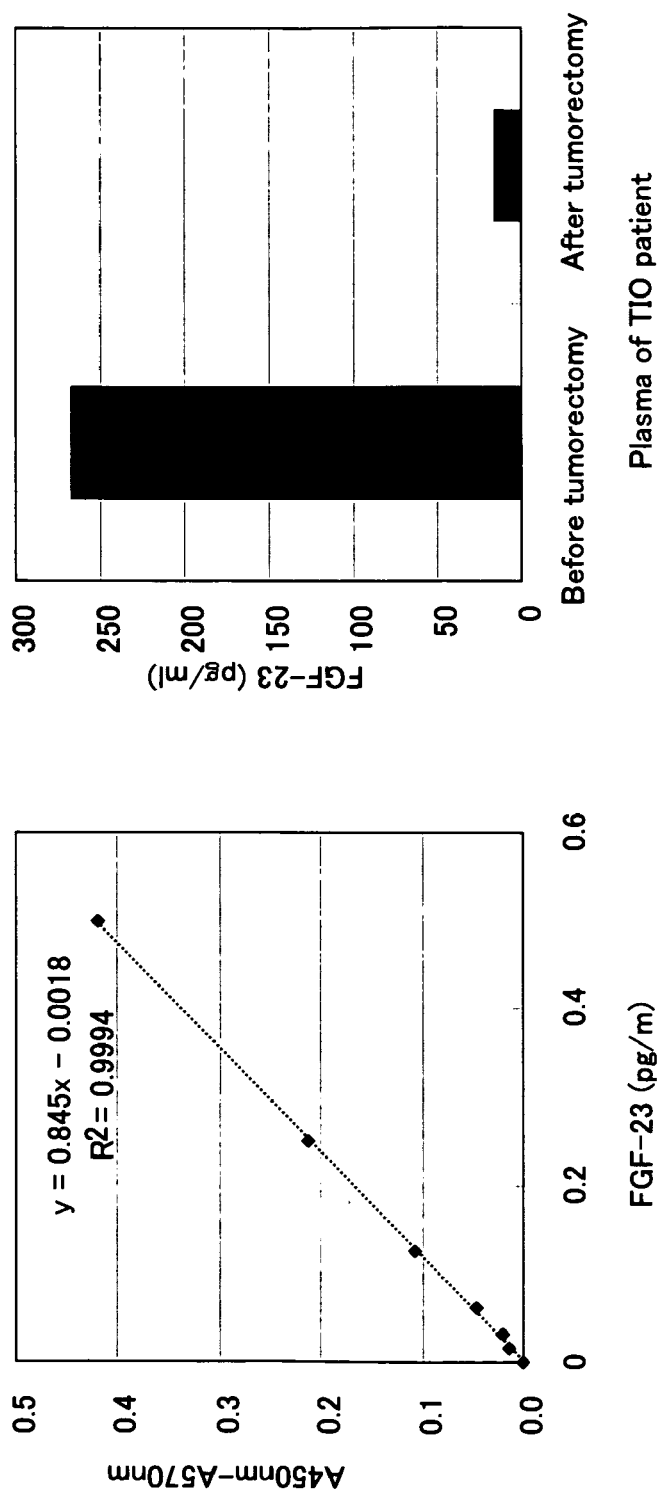
FIG. 14 shows the results of quantifying FGF-23 protein in the blood samples collected before and after extraction of causative tumors of patients with neoplastic osteomalacia. (Examples 19)

Serum and plasma samples were obtained from tumor-induced osteomalacia patients, and quantitative analysis of FGF-23 in the analytes was attempted using a sandwich ELISA system using anti-FGF-23 monoclonal antibodies. The ELISA system using anti-FGF-23 monoclonal antibodies was performed using the above method. The 2C3B antibody was used as an immobilized antibody, and the biotin-labeled 3C1E or 1D6A antibody was used as an antibody for detection. The purified 2C3B antibodies were diluted to 10 μg/ml with a 50 mM sodium hydrogen carbonate solution. 50 μl of the resultant solution was added per well of a 96-well plate for ELISA (Maxisorp (trademark), Nunc, U.S.A.), and then incubated at 4° C. for 12 hours for immobilization. Subsequently, the reaction solutions were removed, 250 μl of a blocking solution (SuperBlock (trademark), PIERCE, U.S.A.) was added per well, and the resultant was incubated at room temperature for 30 minutes, thereby performing blocking. After the solutions were removed, the wells were washed 2 times with TBS (T-TBS) containing 0.1% Tween 20. To avoid non-specific reaction to mouse antibodies, the serum and plasma samples of the tumor-induced osteomalacia patients were diluted 2-fold with T-TBS solutions containing mouse IgG1 at a concentration of 80 μg/ml as isotype controls. Furthermore, to confirm specific reaction to the FGF-23 protein, the samples were diluted 2-fold with T-TBS containing an excessive volume (80 μg/ml) of the 2C3B antibody that had been used for immobilization. Standard solutions to produce a calibration curve were prepared by adding purified FGF-23 protein to serum or plasma of normal subjects diluted with a solution similarly containing the isotype control antibodies to result in concentrations of 0.5, 0.25, 0.125, 0.061, 0.031, and 0.015 ng/ml, respectively. 50 μl of each sample was added per well of a microtiter plate, and then the solutions were incubated at room temperature for 1 hour, thereby performing reaction of the FGF-23 protein in the analytes with immobilized antibodies. After antibody reaction, the wells were washed 4 times with T-TBS, and then 2 types of biotin-labeled anti-FGF-23 monoclonal antibodies (1D6A antibody and 3C1E antibody) diluted at 10 μg/ml with T-TBS containing a 10% blocking solution (Blockace (trademark), DAINIPPON PHARMACEUTICAL CO., LTD. Japan) were added. The solutions were incubated at room temperature for 30 minutes, thereby performing secondary antibody reaction. After each well was washed 4 times with T-TBS, 50 μl of HRP-labeled streptavidin (DAKO, Denmark) diluted 5000-fold with T-TBS containing a 10% blocking solution (Blockace (trademark), DAINIPPON PHARMACEUTICAL CO., LTD. Japan) was added per well. The solutions were incubated at room temperature for 30 minutes, so as to bind the streptavidin with biotin-labeled antibodies. Each well was washed 4 times with T-TBS, and then 50 μl of tetramethylbenzidine (DAKO, Denmark), which is a peroxidase chromogenic substrate, was added per well, followed by incubation at room temperature. 30 minutes later, 50 μl of 0.5 M sulfuric acid solution was added per well, so as to stop reaction. Measurement was conducted using a system for measuring absorbance for a 96-well plate (MTP-300, CORONA ELECTRIC CO., LTD., Japan), and values were obtained by subtracting absorbance at 570 nm from absorbance at 450 nm. A value representing an FGF-23-specific reaction was obtained by subtracting an A450-A570 value measured in the presence of an excessive quantity of the 2C3B antibody from an A450-A570 value measured in the presence of an excessive quantity of the isotype control antibody. The results are shown in FIG. 13. When 1D6A was used as an antibody for detection, measured values of the plasma sample and the serum sample were 0.033 and 0.008, respectively. The measured value was clearly lower for the serum sample than for the plasma sample. On the other hand, when 3C1E was used as an antibody for detection, the measured value of the serum sample and that of the plasma sample were almost the same. These results suggested that the FGF-23 protein might be partially cleaved in this sample, as cleaved in serum described in Example 18. Thus, it was revealed that measured values of clinical samples differ depending on differences in antibodies for detection as described above. Hence, sandwich ELISA was conducted using as an antibody for detection the 3C1E antibody with which cleaved products generated upon serum preparation can also be measured, and then FGF-23 concentrations in plasma samples collected before and after tumorectomy of the patients were measured. Using standard solutions prepared by adding purified FGF-23 protein at various concentrations to plasma samples of normal subjects, a calibration curve was produced based on increases in absorbance corresponding to added quantities of purified protein. The thus produced calibration curve is shown in FIG. 14A. The thus obtained calibration curve can also be used to quantify FGF-23 protein in a human plasma or serum sample diluted 2-fold by detecting the concentration thereof corresponding to that within a range between 30 pg/ml and at least approximately 500 pg/ml of the FGF-23 protein in the standard solutions as a significantly increased concentration. Under such conditions, the FGF-23 concentrations in plasma samples collected the day before tumorectomy and collected 1 month or more after tumorectomy from tumor-induced osteomalacia patients were quantitatively measured. The results are shown in FIG. 14B. FGF-23 protein was present at a concentration of approximately 270 pg/ml in the plasma samples collected before tumorectomy. However, in the samples collected after tumorectomy, the FGF-23 protein concentrations decreased to detection sensitivity (30 pg/ml) or less. Thus, it was clearly shown that in tumor-induced osteomalacia, FGF-23 is present at a measurable concentration in blood because of the presence of causative tumors, and the blood FGF-23 concentrations significantly decrease due to the removal of the tumors. Accordingly, it was shown that ELISA using anti-FGF-23 monoclonal antibodies is useful in diagnosis of tumor-induced osteomalacia, and by the use of antibodies whose recognitions sites are specified, quantitative measurement is possible while taking into consideration the effect of cleavage of FGF-23 by serum.

Example 20

Immunohistological Staining Using Anti-FGF-23 Monoclonal Antibody

Figure 15:
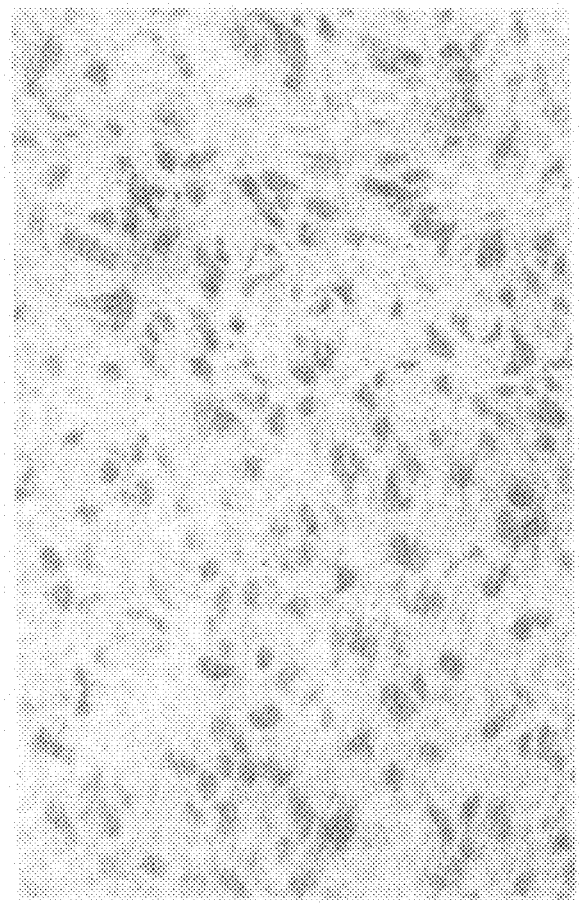
FIG. 15 shows the results of detecting the presence of FGF-23 protein in tumor tissues extracted from patients with neoplastic osteomalacia by immunohistological staining. (Example 20)

The causative tumors of tumor-induced osteomalacia were immunohistologically stained using an anti-FGF-23 monoclonal antibody. An excised tumor was immersed in an embedding solution for the preparation of frozen sections, and then frozen using acetone cooled with liquid nitrogen, thereby preparing blocks of the frozen tumor. In addition, as a control, a frozen block was also similarly prepared from tissue thought to be normal that had been excised upon tumorectomy from the periphery of the tumor tissue. The frozen blocks were thinly sliced at a thickness of 4 μm using a cryostat (CM1900, LEICA, Germany). The section was made to adhere to a MAS coat slide glass (MATSUNAMI GLASS IND., LTD., Japan) while being cooled and dried. The thus prepared frozen sections were stored at −20° C. The slide glasses to which the frozen sections had adhered were incubated in acetone at room temperature for 5 minutes, so that the tissues were immobilized on the slide glasses. After washing with PBS, incubation was performed in PBS containing 1% hydrogen peroxide and 0.1% sodium azide at room temperature for 30 minutes, thereby inactivating endogenous peroxidase. Subsequently, the resultants were washed with PBS containing 0.1% Tween20, and then incubation was performed in PBS containing 4% skim milk at room temperature for 30 minutes, thereby performing blocking. Next, incubation was performed with PBS containing 10 μg/ml biotin-labeled 1C3H and 2C3B antibodies at room temperature for 1 hour, thereby causing FGF-23 in the tissue to react with added monoclonal antibodies. After washing with PBS containing 0.1% Tween20, horseradish peroxidase was bound to the biotin-labeled monoclonal antibodies specifically bound to the tissue sections using a peroxidase kit (Vectastain Elite ABC (trademark), VECTOR Laboratories, U.S.A.). After washing with PBS containing 0.1% Tween20, reaction of peroxidase with substrates (DAKO liquid DAB substrate-chromogen system (trademark), DAKO, Denmark) was conducted, and then reaction was stopped using PBS. After washing with ion exchanged water, incubation was performed in a solution prepared by diluting 5-fold Hematoxylin Mayer (Merck & Co., U.S.A.) with ion exchanged water at room temperature for 30 seconds, followed by washing in running water. Subsequently, dehydration was performed using ethanol, penetration was performed using xylene, and then the resultants were sealed using an encapsulation solution. The results are shown in FIG. 15. The sites thought to have reacted with FGF-23 in tumor tissues were stained brown. However, no such staining images were observed in tissues at the periphery of the tumor. Accordingly, the presence of FGF-23 at high concentrations was confirmed in the causative tumors of tumor-induced osteomalacia.

Example 21

Expression and Purification of Mouse FGF-23 Protein

A mouse FGF-23 sequence has already been reported (Yamashita, T., et al. Biochem. Biophys. Res. Commun. 277: 494-498, 2000). The sequence information of the mouse FGF-23 can be obtained by searching the NCBI gene sequence database based on this sequence. Based on the thus obtained sequence information, nested PCR was performed to obtain cDNA encoding the mouse FGF-23 protein. As primers to be used for the first stage of amplification reaction, an mF5 primer (SEQ ID NO: 25) and an mF3 primer (SEQ ID NO: 26) having sequences complementary to the 5' and the 3' untranslated regions, respectively, of the cDNA sequence of mouse FGF-23 were synthesized. After keeping the temperature at 94° C. for 1 minute, 30 cycles of PCR was performed using cDNA (Clontech, U.S.A.) derived from mouse lungs as a template and LA-Taq DNA polymerase (TAKARA SHUZO, Japan), each cycle consisting of 94° C. for 30 seconds, 55° C. for 30 seconds, and 72° C. for 45 seconds. Next, the second stage of reaction was performed using an mF23F primer represented by SEQ ID NO: 27 containing a region from the initiation codon to the translated region, and an mF23R primer represented by SEQ ID NO: 28 containing a region from the translated region to the termination codon. In the mF23F primer, an EcoR I restriction enzyme recognition sequence for cloning and a Kozak sequence had been introduced. In the meantime, in the mF23R primer, a Not I restriction enzyme recognition sequence had been introduced following the termination codon. After the temperature was kept at 98° C. for 1 minute, 35 cycles of PCR were performed using the reaction solution in the 1$^{st}$ stage as a template and PyroBest DNA polymerase (TAKARA SHUZO, Japan), each cycle consisting of 98° C. for 10 seconds, 58° C. for 10 seconds, and 72° C. for 60 seconds. Thus, the cDNA sequence encoding the mouse FGF-23 protein was amplified. The cDNA was cloned into the EcoR I site and the Not I site of a pEAK8 vector (Edge Biosystem, U.S.A.). This vector is referred to as pEAK8mFGF-23. Furthermore, according to the method for preparing FGF-23RQH shown in Example 1, mouse FGF-23RQ was constructed wherein a mutation had been introduced so as to substitute an arginine residue at a cleavage enzyme recognition site of mouse FGF-23 with a glutamine residue. The mutation was introduced according to the method described in Example 1(3). For the introduction of the mutation, a forward mRQF primer (SEQ ID NO: 29) and a reverse mRQR primer (SEQ ID NO: 30) were synthesized. First, PCR was performed using the pEAK8mFGF-23 as a template, a combination of the mF23F primer and the mRQR primer, and a combination of the mF23R primer and the mRQF primer, thereby obtaining PCR fragments from each case. Next, PCR was performed using a mixture of both products as a template, and the mF23F primer and the mF23R primer which were located on both ends of mouse FGF-23 cDNA, thereby amplifying the mouse FGF-23 cDNA wherein the mutation had been introduced. The product was cloned into the EcoR I restriction enzyme site and the Not I restriction enzyme site of a pEAK8/IRES/EGFP plasmid. The resultant was purified and then the nucleotide sequence was determined, confirming that the mouse FGF-23 cDNA having the target mutation introduced therein had been successfully cloned. This is referred to as pEAK8/IRES/EGFP/mFGF-23RQ. Furthermore, this plasmid was introduced into CHO ras clone-1, 5 μg/ml puromycin (Sigma, U.S.A.) was added, and then drug-resistant cells were selected. After cloning, mouse FGF-23-expressing cells were obtained. Such cells are referred to as CHO-mFGF23RQ. The CHO-mFGF23RQ cells were cultured in a roller bottle, thereby obtaining approximately 12 liters of culture supernatant. The resultant was subjected to purification according to the method for purifying the FGF-23 protein described in Example 2(3), thereby obtaining purified mouse FGF-23RQ.

```
mF5:
ATTAGCCACTCAGTGCTGTGCAATG                 (SEQ ID NO: 25)

mF3:
GCAGCCTGGCCTGGGGACCTA                     (SEQ ID NO: 26)

mF23F:
GGAATTCCACCATGCTAGGGACCTGCCTTAGA          (SEQ ID NO: 27)
CTC mF23R:
ATAGTTTAGCGGCCGCCTAGACGAACCTGGGAAA        (SEQ ID NO: 28)
GGGGCGACA mRQF:
TTCGCCCACGGCAACACACGCAAAGCGCCGAG          (SEQ ID NO: 29)
GAC mRQR:
GTCCTCGGCGCTTTGCGTGTGTTGCCGTGGGC          (SEQ ID NO: 30)
GAA
```

Example 22

Cross Reactivity of Anti-Human FGF-23 Monoclonal Antibodies and FGF-23

Figure 16B:
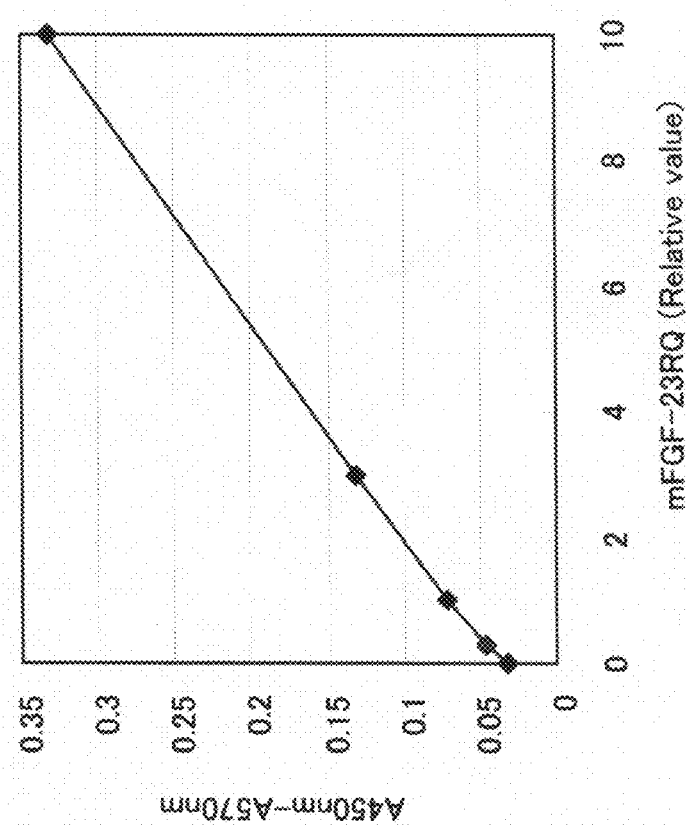
FIG. 16B shows a mouse FGF-23 protein solution as measured using the 2C3B antibody as an immobilized antibody and the 3C1E antibody as an antibody for detection after serial dilution of purified mouse FGF-23 protein. (Example 22)
Figure 16A:
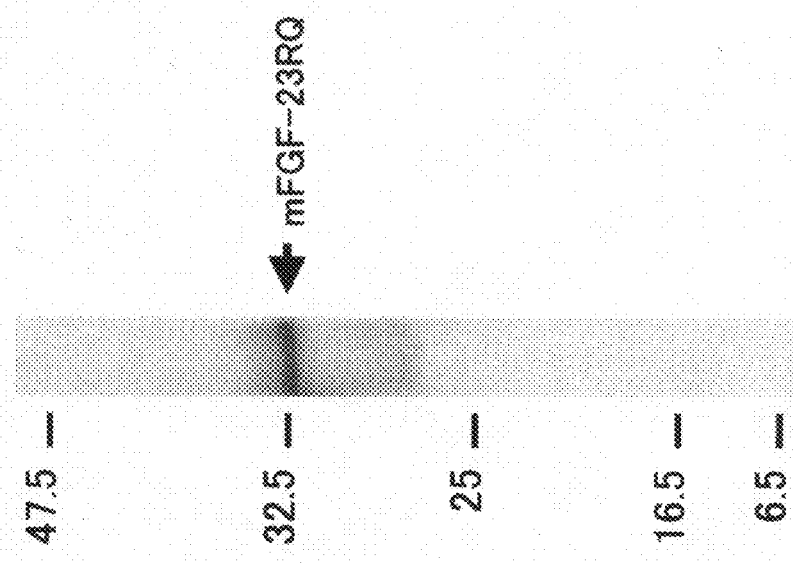
FIG. 16A shows mouse FGF-23RQ protein as detected by Western blotting using the 3C1E antibody, which was an anti-human FGF-23 monoclonal antibody, after separating purified mouse FGF-23RQ protein by SDS-polyacrylamide gel electrophoresis. (Example 22)

The purified mouse FGF-23RQ protein was separated by SDS-polyacrylamide gel electrophoresis, transferred to PVDF membranes (Millipore, U.S.A.), and then subjected to Western blotting using the 3C1E antibody. Thus, a band was detected at approximately 32.5 kDa as shown in FIG. 16A. The purified mouse FGF-23RQ protein solution was serially diluted, and then detection was attempted by sandwich ELISA using anti-human FGF-23 monoclonal antibodies. The concentrations of the mouse FGF-23RQ protein solution used herein were not precisely obtained. As determined from the depth of bands detected when the solutions were subjected to separation by SDS-polyacrylamide gel electrophoresis while being aligned with the purified human FGF-23 protein having a known concentration, and CBB staining, it was considered that the concentrations of the mouse FGF-23RQ protein solutions were within the range between 1 and 5 μg/ml, when expressed using a relative value of 10 as in FIG. 16B. Using the immobilized 2C3B antibody and the 3C1E antibody as an antibody for detection, the diluted mouse FGF-23RQ protein solutions as test substances were measured. The results are shown in FIG. 16B. Since 450 nm-570 nm values were observed to increase in a manner depending on the concentrations of the purified mouse FGF-23RQ protein, it became clear that the mouse FGF-23 protein can be detected in a concentration-dependent manner by ELISA using the anti-human FGF-23 monoclonal antibodies used herein. Furthermore, it could be confirmed that anti-human FGF-23 monoclonal antibodies can recognize the mouse FGF-23 protein, suggesting that the anti-human FGF-23 monoclonal antibodies observed in Examples 27 and 28 act to neutralize or modify the activity by binding with mouse endogenous FGF-23.

Example 23

Detection of Blood FGF-23 Protein of Hereditary Hypophosphatemia Model Mouse

FGF-23 is known to be a factor inducing tumor-induced osteomalacia, and is also known to be involved in inducing ADHR because of missense mutations found in the FGF-23 gene in ADHR. However, in another form of hereditary hypophosphatemia, XLH, although the responsible gene has been elucidated, the mechanism inducing the disease has not yet been understood well. In addition, the relationship with FGF-23 is not known. For the purpose of examining the involvement of FGF-23 in this disease, measurement of blood FGF-23 concentrations in Hyp mice (the XLH model mice) was attempted.

Figure 17:
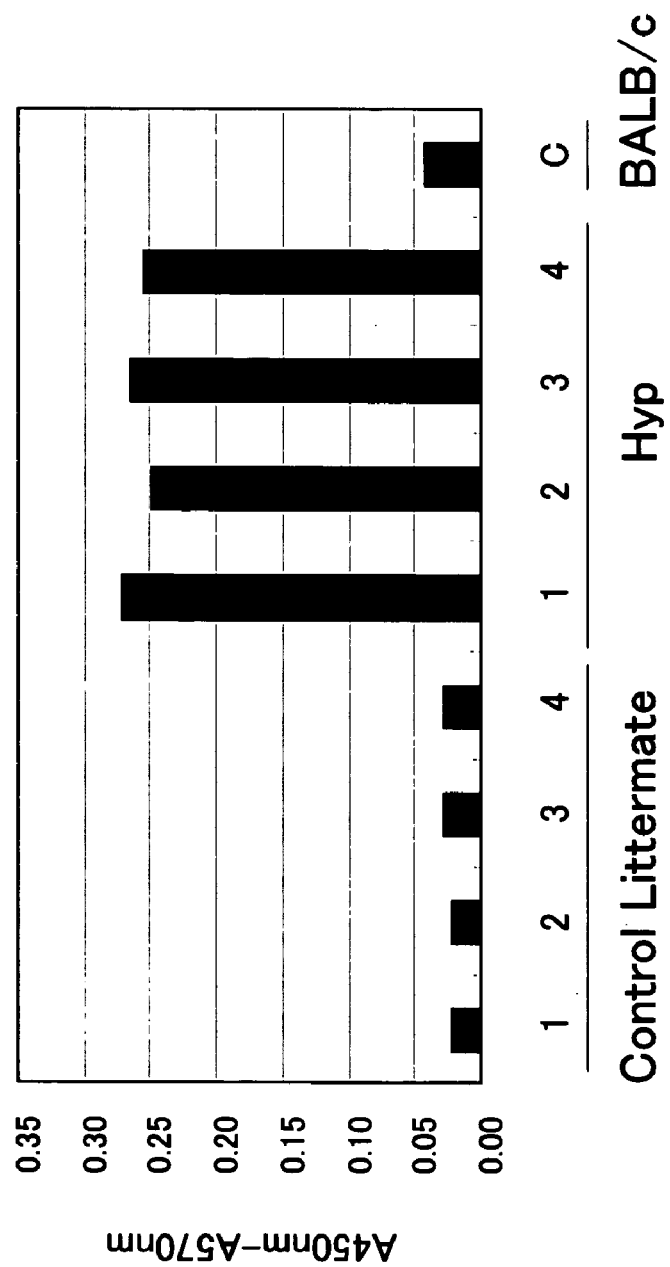
FIG. 17 shows the results of measuring endogenous FGF-23 protein in serum collected from 27- to 30-week-old Hyp mice and control mice using the ELISA system using the 2C3B antibody as an immobilized antibody, and the 3C1E antibody as an antibody for detection. (Example 23)

ELISA was performed using the 2C3B antibody as an immobilized antibody and the biotin-labeled 3C1E antibody as an antibody for detection. The purified 2C3B antibody was diluted to 10 μg/ml with a 50 mM sodium hydrogen carbonate solution. 50 µl of the resultant solution was added per well of a 96-well plate for ELISA (Maxisorp (trademark), Nunc, U.S.A.), and then incubated at 4° C. for 12 hours for immobilization. Subsequently, the reaction solutions were removed, 250 µl of a blocking solution (SuperBlock (trademark), PIERCE, U.S.A.) was added per well, and then the resultant was incubated at room temperature for 30 minutes, thereby performing blocking. After the solutions were removed, the wells were washed 2 times with TBS (T-PBS) containing 0.1% Tween 20. Blood was collected from the eye sockets of 27- to 30-week-old Hyp mice and normal control mice obtained from the same brood, and then serum samples were prepared therefrom. The serum samples were diluted 2-fold with T-TBS containing the 2C3B antibody or a mouse IgG1 antibody as an isotype control, at a concentration of 40 µg/ml. 50 µl of each sample was added per well of a microtiter plate, and then the samples were incubated at room temperature for 1 hour, thereby causing the FGF-23 protein in the analytes to react with the immobilized antibodies. After antibody reaction, the wells were washed 4 times with T-TBS, and then the 3C1E antibody diluted to 2 µg/ml with T-TBS containing a 10% blocking solution (Blockace (trademark), DAINIPPON PHARMACEUTICAL CO., LTD. Japan) was added. The solutions were incubated at room temperature for 30 minutes, thereby performing secondary antibody reaction. After each well was washed 4 times with T-TBS, 50 µl of HRP-labeled streptavidin (DAKO, Denmark) diluted 5000-fold with T-TBS containing a 10% blocking solution (Blockace (trademark), DAINIPPON PHARMACEUTICAL CO., LTD. Japan) was added per well. The solutions were incubated at room temperature for 30 minutes, so as to bind the streptavidin with biotin-labeled antibodies. Each well was washed 4 times with T-TBS, and then 50 µl of tetramethylbenzidine (DAKO, Denmark), which is a peroxidase chromogenic substrate, was added per well, followed by incubation at room temperature. 30 minutes later, 50 µl of 0.5 M sulfuric acid solution was added per well, so as to stop reaction. Measurement was conducted using a system for measuring absorbance for a 96-well plate (MTP-300, CORONA ELECTRIC CO., LTD., Japan), and values (A450-A570) were obtained by subtracting absorbance at 570 nm from absorbance at 450 nm. A value showing a FGF-23-specific reaction was obtained by subtracting an A450-A570 value obtained by the addition of the 2C3B antibody used as an absorption antibody from an A450-A570 value obtained by the addition of the isotype control antibody upon reaction. The results are shown in FIG. 17. The results shown in FIG. 17 clearly show significantly elevated blood FGF-23 concentrations of Hyp mice. Since Hyp mice develop hypophosphatemia due to a PHEX gene deficiency, and XLH, the human hypophosphatemia, is caused by mutation or deficiency in the PHEX gene, Hyp mice are thought to be XLH model mice. This results from the strong suggestion that an elevated blood FGF-23 concentration is present as a factor inducing hyphosphatemia in XLH.

Example 24

Figure 18A:
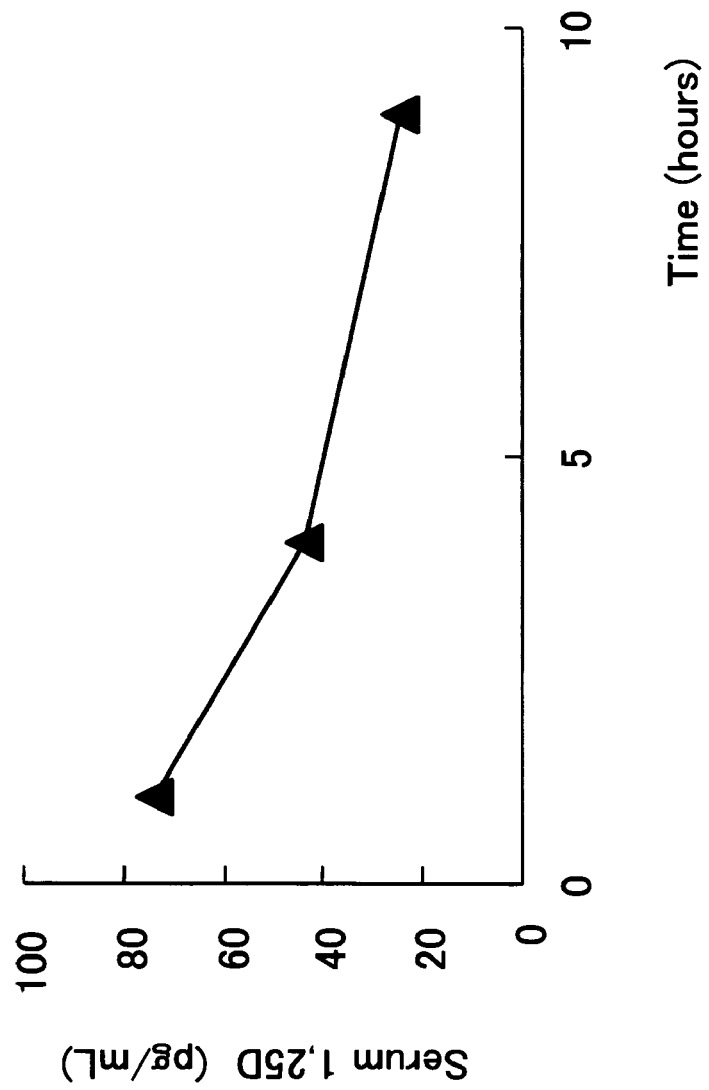
FIG. 18A shows serum 1,25D concentrations as measured after administering 5 μg of purified FGF-23H protein per mouse to six 6-week-old BALB/c male mice, and then collecting blood at 1, 4, and 9 hours after administration. (Example 24)

Mutual Control Action of FGF-23 and 1,25D (1) Decrease in 1,25D by Administration of FGF-23H
5 µg per mouse of the purified FGF-23H protein was administered via the caudal vein to six 6-week-old BALB/c male mice. At 1, 4, and 9 hours after administration, blood was collected, and then blood 1,25D concentrations were measured. The results are shown in FIG. 18A. At 3 hours after administration of FGF-23H, a significant decrease was observed in 1,25D, and the concentration was observed to further decrease at 9 hours after the administration.

Figure 18B:
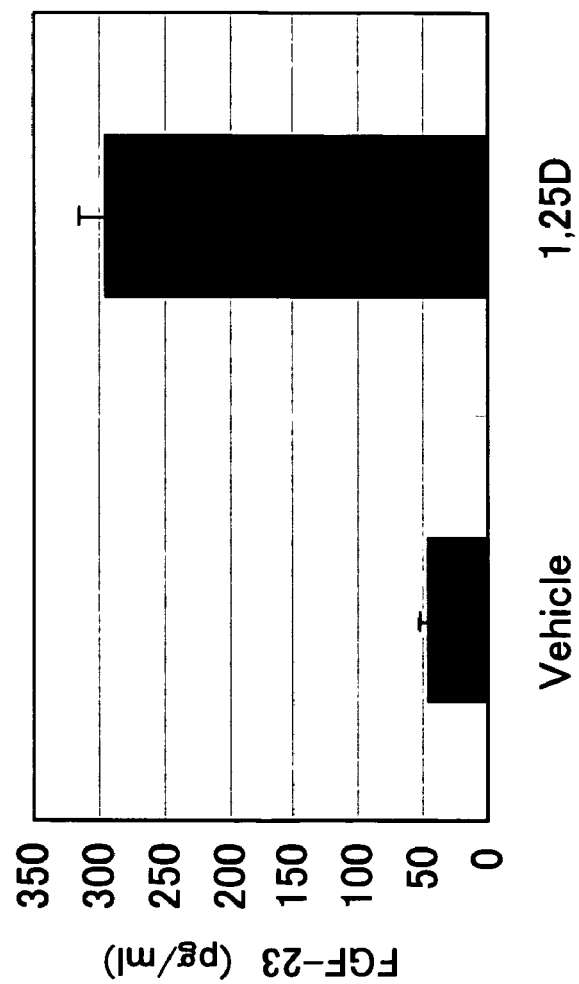
FIG. 18B shows serum FGF-23 quantities as measured after administering 0.025 μg of 1,25D intraperitoneally to six 7-week-old BALB/c male mice, and then collecting blood at 8 hours after administration. (Example 24)

(2) Induction of FGF-23 by Administration of 1,25D
1,25D was administered to mice, and changes in blood FGF-23 were examined. Six 7-week-old BALB/c male mice composed each group. A group to which 0.025 µg of 1,25D dissolved in PBS containing 0.05% tween was administered, and a control group to which PBS containing 0.05% tween, the vehicle, was administered were established. Administration was performed intraperitoneally. 8 hours after the administration, blood was collected from the heart under anesthesia, and then serum samples were prepared. These samples were subjected to ELISA by the same method as that of Example 23, and then the quantities of FGF-23 in blood were measured using the calibration curve prepared using the standard solutions of the human FGF-23 protein. The results are shown in FIG. 18B. At 8 hours after the administration of 1,25D, a significant increase was observed in blood FGF-23.

Accordingly, it was shown that FGF-23 has a close mutual control relationship with 1,25D.

Example 25

Blood FGF-23 Concentration in Renal Failure Hyperphosphatemia Model

Figure 19B:
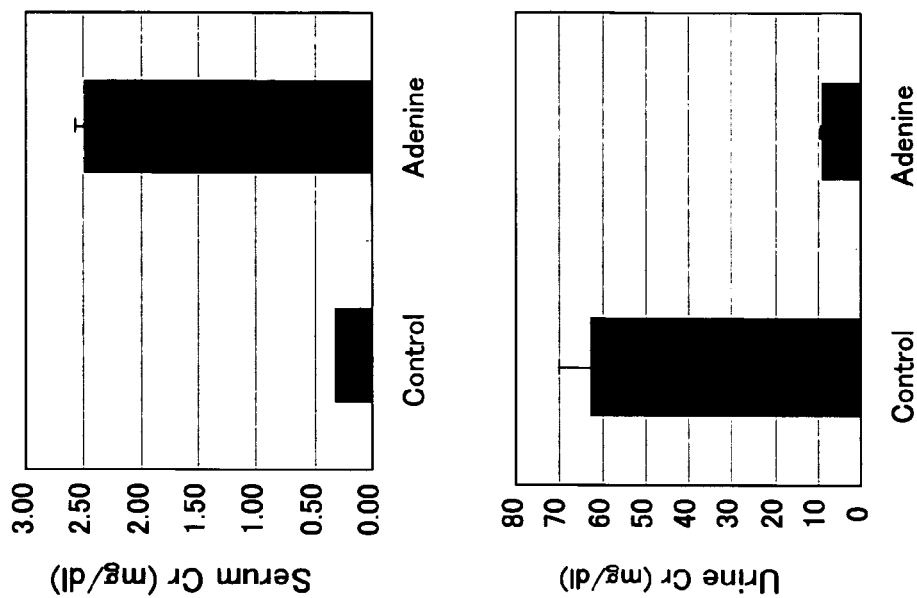
FIG. 19B shows serum and urine creatinine concentrations measured after feeding CE-2 (CLEA JAPAN, INC.), with which adenine had been mixed at a rate of 0.75%, to 7-week-old Wistar rats to produce a renal failure hyperphosphatemia model, feeding CE-2 to a control group, and collecting blood 3 weeks after administration of feed mixed with adenine and urine for 24 hours from the rats housed in metabolism cages. (Example 25)
Figure 19A:
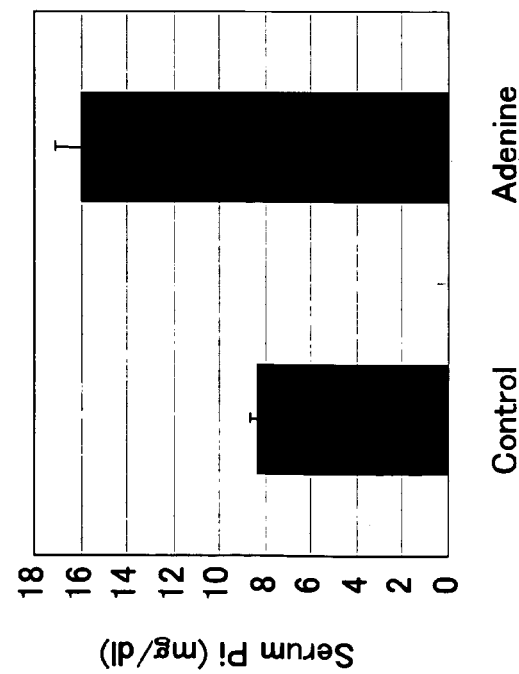
FIG. 19A shows serum phosphate concentrations measured after feeding CE-2 (CLEA JAPAN, INC.), with which adenine had been mixed at a rate of 0.75%, to 7-week-old Wistar rats to produce a renal failure hyperphosphatemia model, feeding CE-2 to a control group, and then collecting blood 3 weeks after administration of feed mixed with adenine. (Example 25)
Figure 19C:
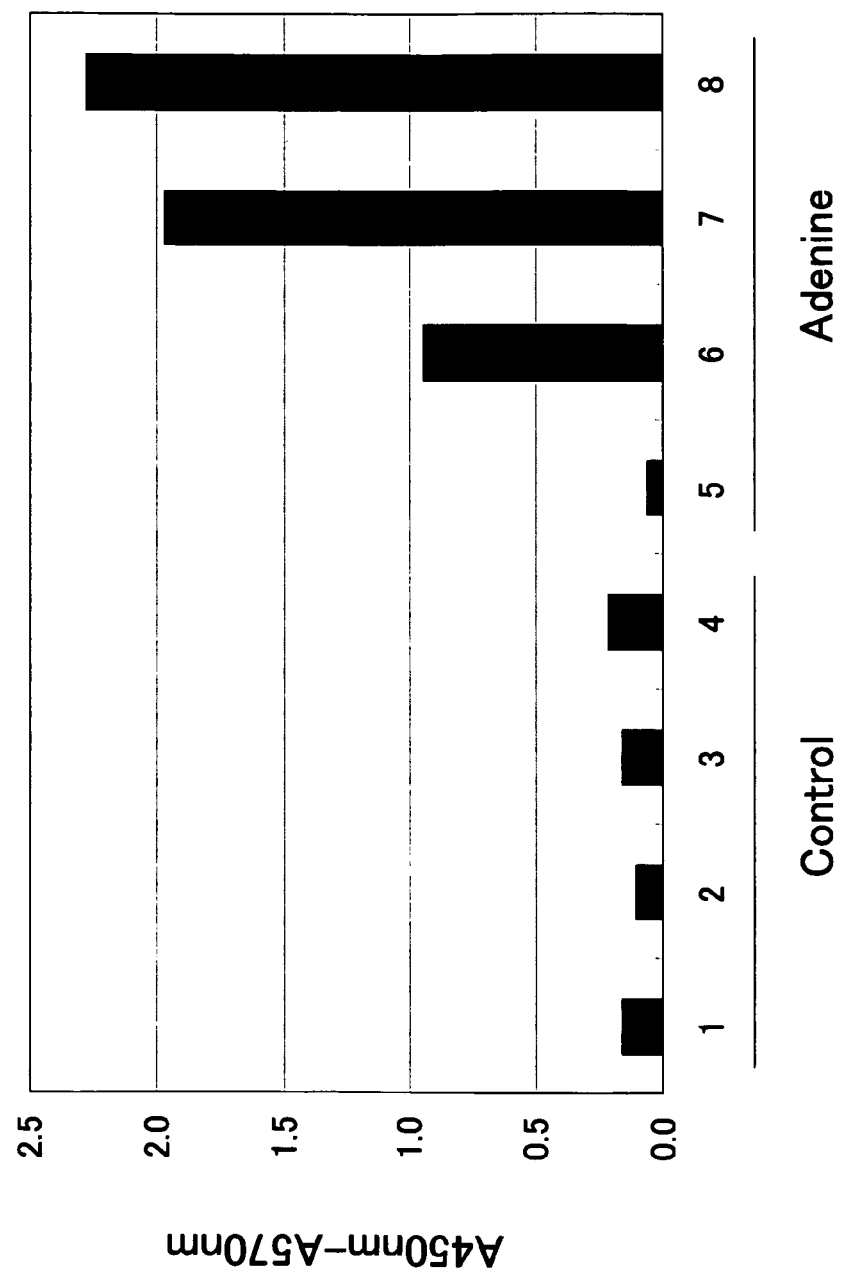
FIG. 19C shows serum FGF-23 concentrations as measured using the ELISA system using the 2C3B antibody as an immobilized antibody, and the 3C1E antibody as an antibody for detection after feeding CE-2 (CLEA JAPAN, INC.), with which adenine had been mixed at a rate of 0.75%, to 7-week-old Wistar rats to produce a renal failure hyperphosphatemia model, feeding CE-2 to a control group, and then collecting blood 3 weeks after administration of feed mixed with adenine. (Example 25)

CE-2 (CLEA Japan, Inc., Japan) mixed with adenine at the rate of 0.75% was fed to 7-week-old Wistar rats, preparing a renal failure hyperphosphatemia model. To a control group, CE-2 was fed. 3 weeks after the start of feeding the mixed feed, blood was collected via the caudal artery, so as to collect serum. After blood collection, rats were housed in metabolic cages and urine was collected for 24 hours. Serum phosphate concentrations were measured. The results are shown in FIG. 19A. Creatinine in serum and that in urine were measured by an enzyme method using a commercial kit (CRE-EN Kainos (trademark), KAINOS LABORATORIES, INC., Japan). The results are shown in FIG. 19B. Moreover, serum FGF-23 concentrations were measured using an ELISA system using the 2C3B antibody as an immobilized antibody and the 3C1E antibody as an antibody for detection. The results are shown in FIG. 19C.

That a disorder of renal functions had progressed in this model was clearly shown by decreased urine creatinine concentrations and increased blood creatinine concentrations. With this progress, the model developed hyperphosphatemia. In this model, blood FGF-23 protein was at a significantly high level. This model was thought to reflect a mode of renal failure, suggesting the possibility that FGF-23 acts as a factor inducing some complications in decreased renal functions and in hemodialysis patients.

Example 26

Figure 20:
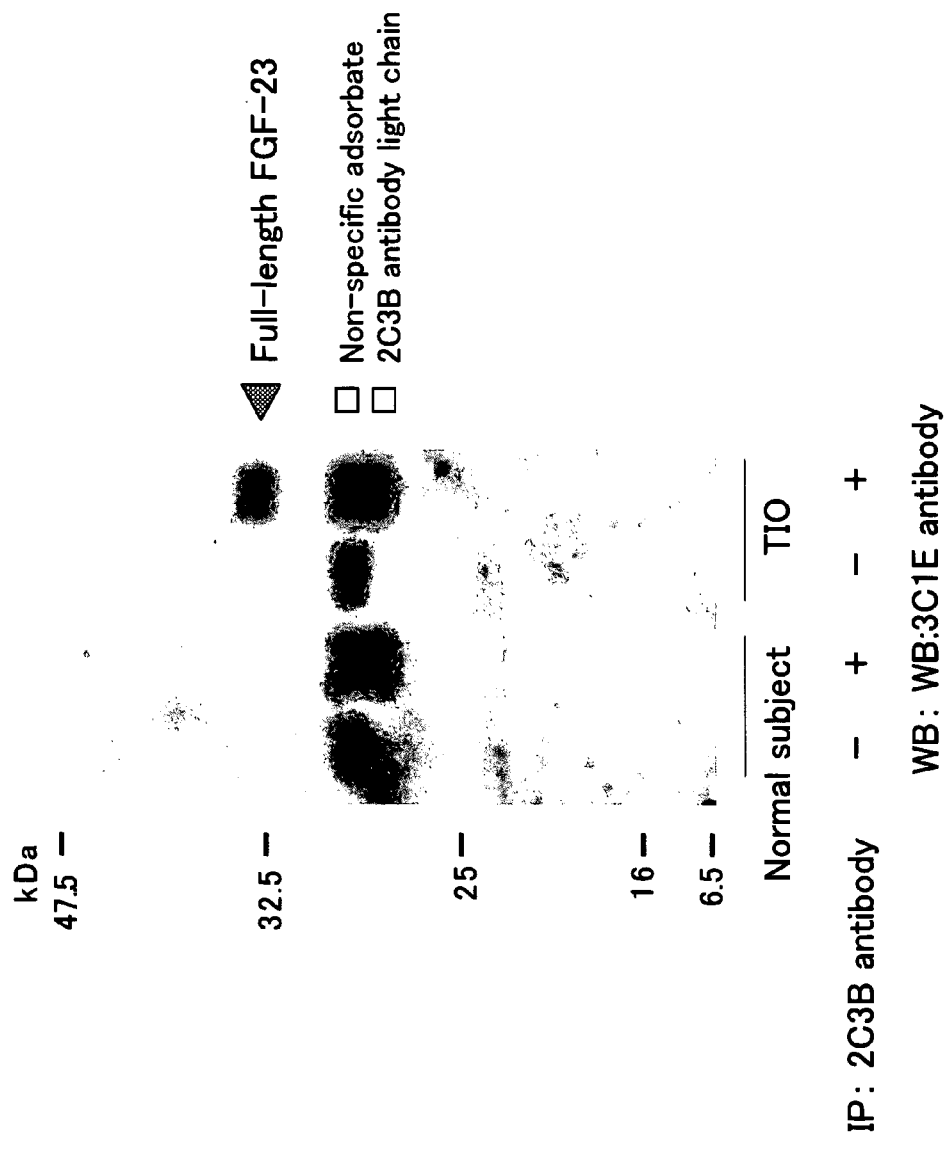
FIG. 20 shows the results of detecting FGF-23 protein existing in the plasma of patients with neoplastic osteomalacia by an immunoprecipitation method. (Example 26)

Detection by Immunoprecipitation Method of FGF-23 Protein Existing in the Plasma of Tumor-Induced Osteomalacia Patients To examine a state of the presence of FGF-23 protein in blood, detection was performed by the immunoprecipitation method using plasma of normal subjects or plasma of tumor-induced osteomalacia patients. To 400 µl of a mixed plasma sample, 20 µl of resins (prepared in Example 14) to which the 2C3B antibody had been immobilized, or resins to which no antibodies had been immobilized, was added. The resultants were admixed by being turned upside down at 4° C. for 1 hour, so as to cause the antibodies to react with FGF-23. Subsequently, the resins were washed 4 times with PBS, thereby removing unreacted products. 50 µl of a sample buffer (50 mM Tris-Cl pH6.8, 1% SDS, 10% glycerol, 0.001% bromophenol blue, 2 mM EDTA, and 20 mM DTT) was added to each type of resin. After heating at 95° C. for 5 minutes, centrifugation was performed, and then the obtained supernatants were collected. The supernatants were separated by 10-20% gradient polyacrylamide gel electrophoresis, and then protein in gel was transferred to PVDF membranes (Millipore, U.S.A.) using a Semi Dry Blotting System (Owl Separation Systems, U.S.A.). Then, the PVDF membrane was incubated at room temperature for 2 hours in a solution of biotin-labeled 3C1E antibody that had been diluted at 0.5 µg/ml in T-TBS (Sigma, U.S.A.). Furthermore, HRP-labeled streptavidin (DAKO, Denmark) was allowed to react with the solutions. The resultants were exposed to film using an ECL Plus luminescence system (Amersham Pharmacia Biotech, U.S.A.) for 1 hour, and then the film was developed using an automatic processor (FUJI PHOTO FILM CO., LTD., Japan). The results are shown in FIG. 20. For the resins to which no antibodies had been immobilized, only plasma-derived non-specific signals were observed. However, regarding the products immunoprecipitated using the 2C3B antibody, a band was detected at 32 kDa, and was suspected to represent the full-length FGF-23 in the plasma of tumor-induced osteomalacia patients. Furthermore, no bands of 22 kDa corresponding to products cleaved by thrombin were detected at all. In the meantime, in normal subjects, neither 22 kD band nor 32 kD band was observed. From these results, it was revealed that FGF-23 expressing at high levels in tumor-induced osteomalacia exists in its full-length form without being cleaved in blood.

Example 27

Figures 21A, 21B:
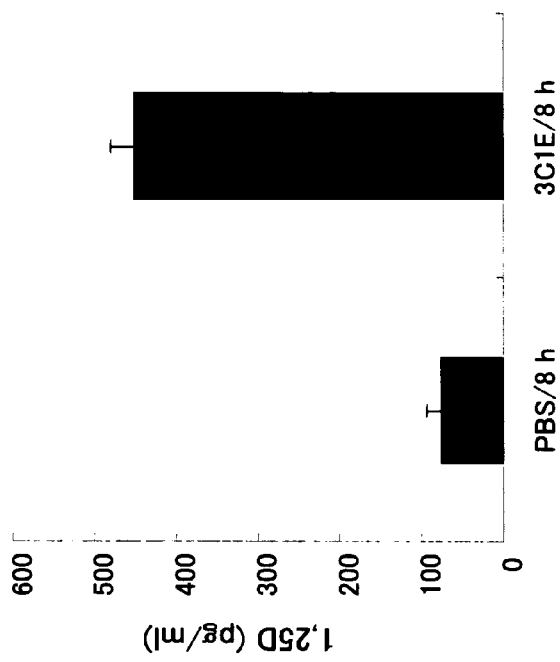
FIG. 21A shows the concentrations of serum phosphate, calcium, and 1,25-dihydroxy vitamin D at 24 hours after administration of various monoclonal antibodies and a vehicle. (Example 27)
FIG. 21B shows serum 1,25-dihydroxy vitamin D concentrations 8 hours after the administration of the 3C1E monoclonal antibody and a vehicle. (Example 28)

Experiment of Administration of Anti-Human FGF-23 Monoclonal Antibodies to Normal Mice To examine the effect of the anti-human FGF-23 monoclonal antibodies on normal mice, the following experiment was conducted. Normal mice (BALB/c, male, 12-week-old) were randomly divided into 5 groups, each of which consisted of 4 mice. As shown in FIG. 21A, single administration of 0.15 ml of PBS as a vehicle was performed via the caudal vein per mouse of group 1, that of 0.67 mg/ml anti-human FGF-23 monoclonal antibodies (1D6A antibody, 2C3B antibody, and 3C1E antibody) was performed via the caudal vein per mouse of groups 2, 3, and 4, respectively, and that of 0.67 mg/ml anti-TPO monoclonal antibodies as a control was performed via the caudal vein per mouse of group 5. 24 hours after the administration, blood was collected from the heart under ether anesthesia, and then serum was separated using a microtainer (Becton Dickinson, U.S.A.). Phosphate concentrations in the thus obtained serum were measured using P (phosphorus)-Test Wako (Wako Pure Chemical Industries, Ltd., Japan), the serum calcium concentrations were measured using a Calcium-Test Wako (Wako Pure Chemical Industries, Ltd., Japan), and serum 1,25D concentrations were measured using a 1,25(OH)2D RIA Kit TFB (TFB, U.S.A.) according to the attached documents. During the period from administration to blood collection, each group of mice was kept in a plastic cage, and fed ad libitum with CE-2 solid feed (CLEA Japan, Inc., Japan) containing 1% phosphorus and 1% calcium, along with tap water.

The results are shown in FIG. 21A. Measured values are expressed with average value+/−standard deviation of each group. Groups marked with a "*" symbol showed p<0.01 for both the group to which the vehicle (PBS) had been administered and the group to which anti-TPO antibody had been administered when tests of significance were conducted by Student-t.

Example 28

In Example 27, although increases were observed in serum phosphorus concentrations in the case of the 3C1E antibody, decreases were observed in serum 1,25D concentrations. However, it is known that blood 1,25D concentrations change rapidly, such that when a 1,25D concentration is temporarily increased, it can exhibit a lower concentration thereafter. Hence, an experiment of administration of the 3C1E antibody was conducted again. The 3C1E antibody was administered intravenously at 400 µg/head to 6 normal mice. 8 hours after the administration, serum 1,25D concentrations were measured. As a control, serum 1,25D concentrations of mice similarly treated by administration of PBS were measured. The results are shown in FIG. 21B. In this experiment, significant increases resulting from the administration of the 3C1E antibody were observed in serum 1,25D concentrations.

Example 29

Figure 22A:
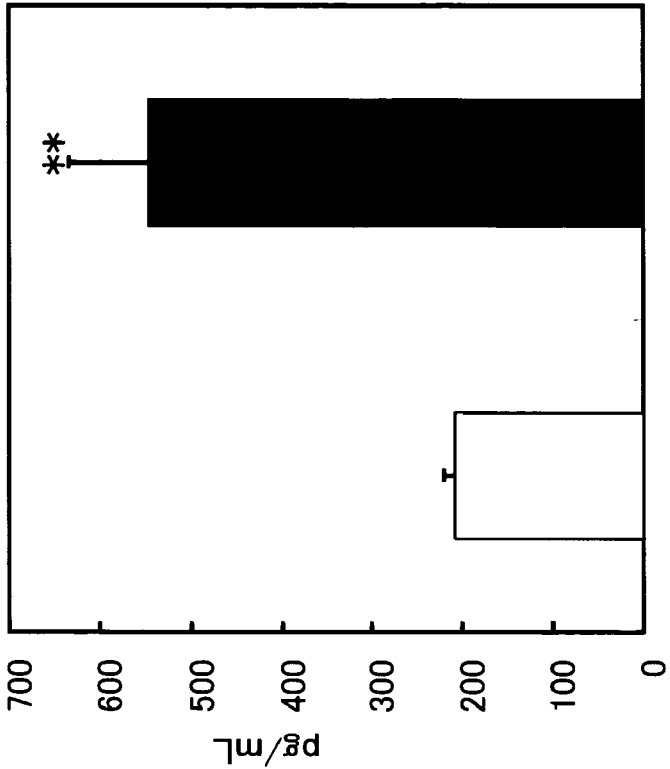
FIG. 22A shows serum 1,25-dihydroxy vitamin D concentrations on day 7 after the start of keeping in a group (adenine) to which feed mixed with adenine had been given, or a group (control) to which general feed had been given. Measured values are expressed with average value+/−standard deviation. "*" and "**" indicate p<0.05 and p<0.01, respectively, which are the results of tests of significance conducted by Student-t. (Example 29)

Effect of Anti-FGF-23 Antibody (3C1E Antibody) to Recover 1,25(OH)$_2$D in Rats Having Renal Failure Induced by Adenine As described in Example 25, in rats having renal failure induced by adenine, on week 3 after the production of the model, significant increases were observed in serum phosphorus concentrations and blood FGF-23 concentrations. Furthermore, in this model, already on day 7 after administration of adenine, decreases were also observed in blood 1,25D concentrations as renal functions decreased (FIG. 22A). Hence, to compare and examine blood FGF-23 concentrations in the early stage of a disorder of renal functions, quantification was conducted in the manner described below.

In ELISA assay, the 2C3B antibody was used as an immobilized antibody, and the biotin-labeled 3C1E antibody was used as an antibody for detection. First, the purified 2C3B antibody was diluted to 5 µg/ml with a 50 mM sodium hydrogen carbonate solution. 50 µl of the resultant solution was added per well of a 96-well plate for ELISA (Maxisorp (trademark), Nunc, U.S.A.), and then incubated at 4° C. for 12 hours for immobilization. Subsequently, the reaction solutions were removed, 250 µl of a blocking solution (SuperBlock (trademark), PIERCE, U.S.A.) was added per well, and then the resultant was incubated at room temperature for 30 minutes, thereby performing blocking. After the solutions were removed, the wells were washed 2 times with TBS (T-TBS) containing 0.1% Tween 20. The serum was prepared and diluted 2-fold with T-TBS. In addition, standard products were diluted using rat serum that had been subjected to the anti-2C3B-antibody-immobilized resins prepared in Example 14 so as to remove endogenous FGF-23, and then diluted 2-fold with T-TBS. 50 µl of each sample was added per well of a microtiter plate, and then the samples were incubated at room temperature for 1 hour, thereby causing the FGF-23 protein in the analytes to react with the immobilized antibodies. After antibody reaction, the wells were washed 4 times with T-TBS, and then the 3C1E antibody diluted to 1.5 µg/ml with T-TBS containing a 10% blocking solution (Blockace (trademark), DAINIPPON PHARMACEUTICAL CO., LTD. Japan) were added. The solutions were incubated at room temperature for 30 minutes, thereby performing secondary antibody reaction. After each well was washed 4 times with T-TBS, 50 µl of HRP-labeled streptavidin (DAKO, Denmark) diluted 5000-fold with T-TBS containing a 10% blocking solution (Blockace (trademark), DAINIPPON PHARMACEUTICAL CO., LTD. Japan) was added per well. The solutions were incubated at room temperature for 30 minutes, so as to bind the streptavidin with the biotin-labeled antibodies. Each well was washed 4 times with T-TBS, and then 50 µl of tetramethylbenzidine (DAKO, Denmark), which is a peroxidase chromogenic substrate, was added per well, followed by incubation at room temperature. 30 minutes later, 50 µl of 0.5 M sulfuric acid solution was added per well, so as to stop reaction. Measurement was conducted using a system for measuring absorbance for a 96-well plate, and values (A450-A570) were obtained by subtracting absorbance at 570 nm from absorbance at 450 nm. Concentrations were calculated by converting the values into values denoting concentrations of the purified products of recombinant human FGF-23 protein based on the calibration curve.

Figure 22B:
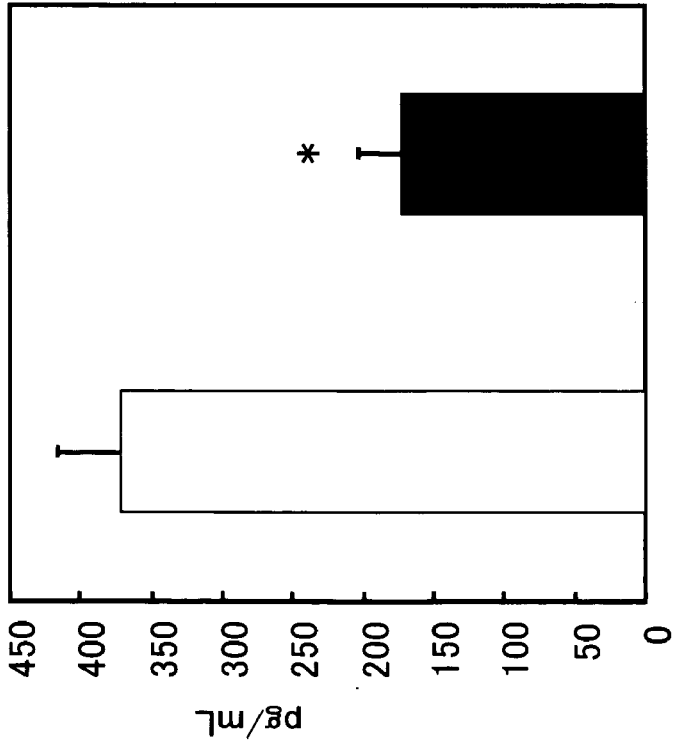
FIG. 22B shows serum FGF-23 concentrations on day 7 after the start of keeping in a group (adenine) to which feed mixed with adenine had been given, or in a group (control) to which general feed had been given. Measured values are denoted with average value+/− standard deviation. "*" and "**" indicate p<0.05 and p<0.01, respectively, which are the results of tests of significance conducted by Student-t. (Example 29)
Figure 22C:
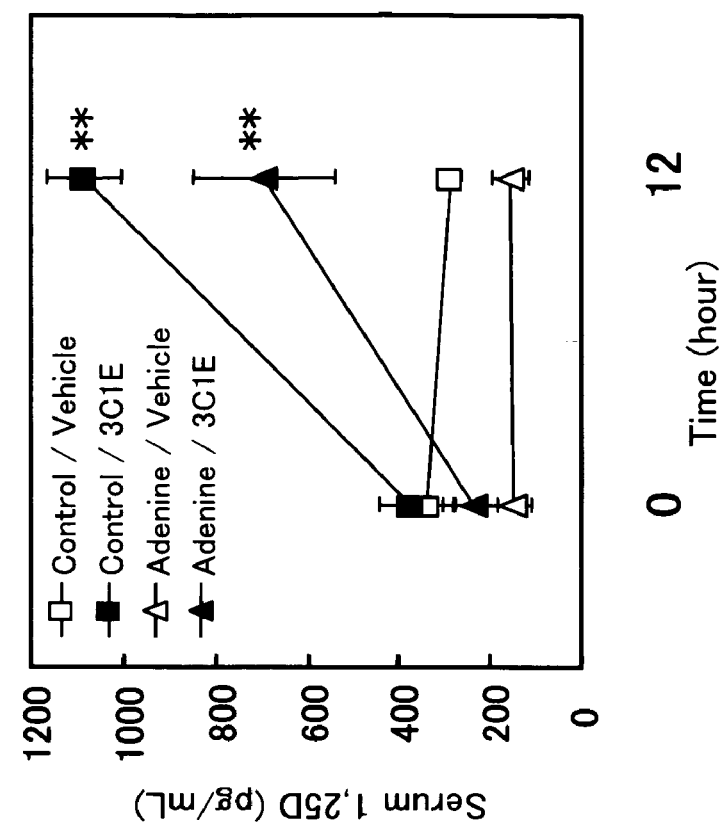
FIG. 22C is a correlation diagram wherein the serum FGF-23 concentrations and 1,25-dihydroxy vitamin D concentrations on day 7 after the start of keeping in a group to which feed mixed with adenine had been given are plotted by individual mice. (Example 29)

As a result, as shown in FIG. 22B, a significant increase was observed in the blood FGF-23 concentrations of the group to which feed mixed with adenine had been given. As shown in Example 24, administration of FGF-23 to normal mice can cause a rapid decrease in blood 1,25D concentration, suggesting the presence of some relationship between a decrease in blood 1,25D and an increase in blood FGF-23 concentration when renal functions decrease. To verify the possibility, blood 1,25D concentrations and blood FGF-23 concentrations after feeding of feed mixed with adenine were plotted for individual rats. Thus, it was revealed that they show a significant negative linear correlation (FIG. 22C). These results suggested the possibility that controlling blood FGF-23 concentrations can correct decreases in blood 1,25D. Hence, an experiment of administration of antibodies neutralizing anti-FGF-23 to this model was conducted in the manner described below.

Twelve 7-week-old male Wister rats were fed ad lititum for 7 days with mixed feed prepared by compounding adenine (6-aminopurine, Sigma, U.S.A.) to a final concentration of 0.75% with CE-2 commercial powder feed for rodents (CLEA Japan, Inc., Japan), thereby producing a model having decreased renal functions. To 12 mice of a control group, only CE-2 was fed. To make the degree of the disorder of renal functions equivalent using a blood creatine level on day 7 after the production of the model, the rats of each group fed with feed mixed with adenine and the rats of the control group were each divided into 2 groups (6 rats/group), and then single administration of the 3C1E antibody was performed at 1 mg/kg or that of PBS (vehicle) was performed at 1 ml/kg, via the caudal vein. 12 hours later, partial blood collection was performed via the caudal artery, and then the blood was subjected to centrifugation, thereby obtaining serum. 1,25D concentration in the obtained serum was measured using a 1,25(OH)2D RIA kit TFB (TFB, U.S.A.), and creatinine concentration in the obtained serum was measured using CREEN Kainos ((trademark), KAINOS LABORATORIES, INC., Japan).

Figure 22D:
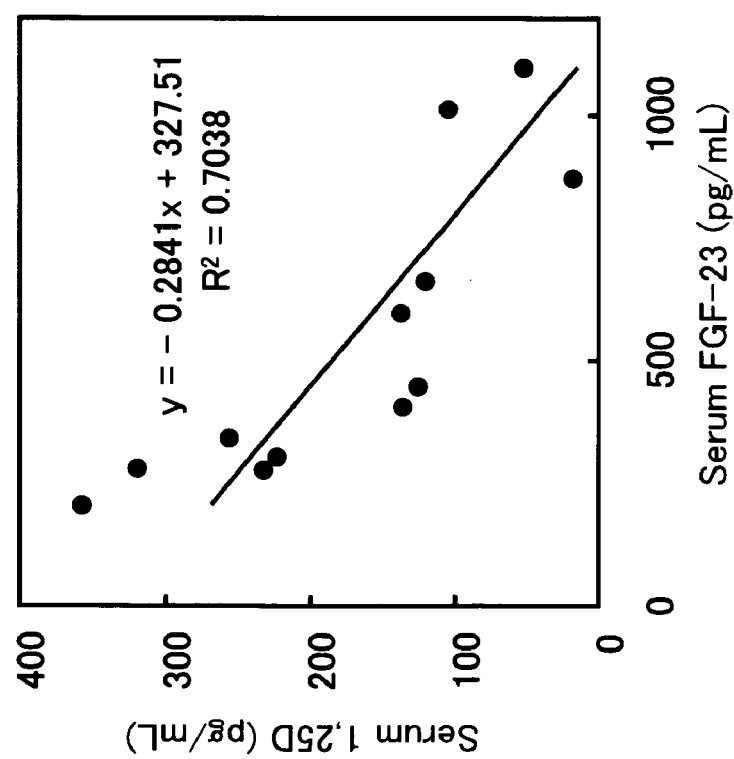
FIG. 22D shows changes in serum 1,25-dihydroxy vitamin D concentrations at 12 hours after administering the 3C1E antibody or a vehicle on day 7 after the start of keeping to a group (adenine) to which feed mixed with adenine had been given, or a group (control) to which general feed had been given. Measured values are expressed with average value+/− standard deviation. "*" and "**" indicate p<0.05 and p<0.01, respectively, which are the results of tests of significance conducted by Student-t. (Example 29)

As a result, as shown in FIG. 22D, in all of the control groups and the groups fed with feed mixed with adenine, significant increases were observed in 1,25D concentrations compared with each group given with a vehicle. The above results suggested that FGF-23 is involved in hypovitaminosis D (disease with low levels of 1,25D in blood) accompanying decreased renal functions, and at this time the suppression of the action of FGF-23 can improve hypovitaminosis D.

Example 30

Detection of Blood FGF-23 Protein in a X-Linked Hypophosphatemic Rickets (XLH) Patient XLH is a form of hypophosphatemic rickets showing an X-linked inherited character, and the morbidity thereof shares many points in common with that of tumor-induced osteomalacia. In recent years, phex belonging to the metalloendopeptidase family has been identified as the causative gene of this disease, and a putative substrate thereof has been suggested to be a factor inducing morbidity. In the meantime, as shown in Example 23, it was revealed that blood FGF-23 concentrations are extremely high in Hyp mice, which are hereditary hypophosphatemia model mice having a gene mutation in phex that is the same as that in XLH. These phenomena suggested the possibility that hypophosphatemia in XLH, similarly to that in tumor-induced osteomalacia, is caused by elevated blood FGF-23 concentrations. Hence, first, for the purpose of examining the involvement of FGF-23 in this disease, FGF-23 concentrations in the serum of normal subjects and XLH patients were measured. In addition, serum subjected to measurement had been provided after having obtained the sufficient prior approval of normal subjects and XLH patients confirmed to have gene mutations in phex. The age, gender, and mutation position of the phex gene of the patients are described in FIG. 23.

In ELISA assay, the 2C3B antibody was used as an immobilized antibody, and the biotin-labeled 3C1E antibody was used as an antibody for detection. First, the purified 2C3B antibody was diluted to 10 µg/ml with a 50 mM sodium hydrogen carbonate solution. 50 µl of the resultant solution was added per well of a 96-well plate for ELISA (Maxisorp (trademark), Nunc, U.S.A.), and then incubated at 4° C. for 12 hours for immobilization. Subsequently, the reaction solutions were removed, 250 µl of a blocking solution (SuperBlock (trademark), PIERCE, U.S.A.) was added per well, and then the resultant was incubated at room temperature for 30 minutes, thereby performing blocking. After the solutions were removed, the wells were washed 2 times with TBS (T-PBS) containing 0.1% Tween 20. The serum collected from XLH patients were prepared, and diluted 2-fold with T-TBS containing a mouse IgG1 antibody not binding to FGF-23 at a concentration of 100 µg/ml. In addition, standard products were diluted using the serum of normal subjects (from which endogenous FGF-23 had been removed by subjecting the serum to the anti-2C3B-antibody-immobilized resins prepared in Example 14) diluted 2-fold with T-TBS containing the mouse IgG1 antibody not binding to FGF-23 at a concentration of 100 µg/ml. 50 µl of each sample was added per well of a microtiter plate, and then the samples were incubated at room temperature for 1 hour, thereby causing the FGF-23 protein in the analytes to react with the immobilized antibodies. After antibody reaction, the wells were washed 4 times with T-TBS, and then the biotin-labeled 3C1E antibody diluted to 1.5 µg/ml with T-TBS containing a 10% blocking solution (Blockace (trademark), DAINIPPON PHARMACEUTICAL CO., LTD. Japan) was added. The solutions were incubated at room temperature for 30 minutes, thereby performing secondary antibody reaction. After each well was washed 4 times with T-TBS, 50 µl of HRP-labeled streptavidin (DAKO, Denmark) diluted 5000-fold with T-TBS containing a 10% blocking solution (Blockace (trademark), DAINIPPON PHARMACEUTICAL CO., LTD. Japan) were added per well. The solutions were incubated at room temperature for 30 minutes, so as to bind the streptavidin with the biotin-labeled antibodies. Each well was washed 4 times with T-TBS, and then 50 µl of tetramethylbenzidine (DAKO, Denmark), which is a peroxidase chromogenic substrate, was added per well, followed by incubation at room temperature. 30 minutes later, 50 µl of 0.5 M sulfuric acid solution was added per well, so as to stop reaction. Measurement was conducted using a system for measuring absorbance for a 96-well plate, and values (A450-A595) were obtained by subtracting absorbance at 595 nm from absorbance at 450 nm.

As a result, blood FGF-23 concentrations of 104 normal adults (30 men and 74 women) were aggregated in a range from 8.2 to 54.3 ng/l, and the average value and the standard error thereof were 28.9±1.1 ng/l. In the meantime, as shown in FIG. 23, all of the serum FGF-23 concentrations in XLH patients were higher than the average values for normal subjects, and even the average concentration in XLH patients was also significantly higher than that of normal subjects ($p<0.0001$, calculated by Student-t). These results strongly suggested the possibility that FGF-23 at high concentrations in the serum of XLH patients acts as a factor inducing the disease.

Example 31

Action Augmenting Neutralization Activity when 2 Different Types of Neutralization Antibody are Mixed Changes in physiological action when neutralization antibodies recognizing different sites were mixed were examined using normal mice.

8-week-old male C57BL/6 mice were randomly divided into 4 groups, each consisting of 6 mice. Single administration of PBS as a vehicle was performed per mouse via the caudal vein for group 1, that of 100 µg of the 2C3B antibody was performed per mouse via the caudal vein for group 2, that of 100 µg of the 3C1E antibody was performed per mouse via the caudal vein for group 3, and that of the admixture of antibodies (50 µg of the 2C3B antibody and 50 µg of the 3C1E antibody) was performed per mouse via the caudal vein for group 4. On days 1 and 2 after administration, blood was collected from the eye sockets under ether anesthesia, and then serum was separated using a microtainer (Becton Dickinson, U.S.A.). Phosphate concentrations in the thus obtained serum were measured using P (phosphorus)-Test Wako (Wako Pure Chemical Industries, Ltd., Japan) according to the attached document. During the period from administration to blood collection, each group of mice was kept in a plastic cage, and fed ad libitum with CE-2 (CLEA Japan, Inc., Japan) along with tap water.

Figure 24:
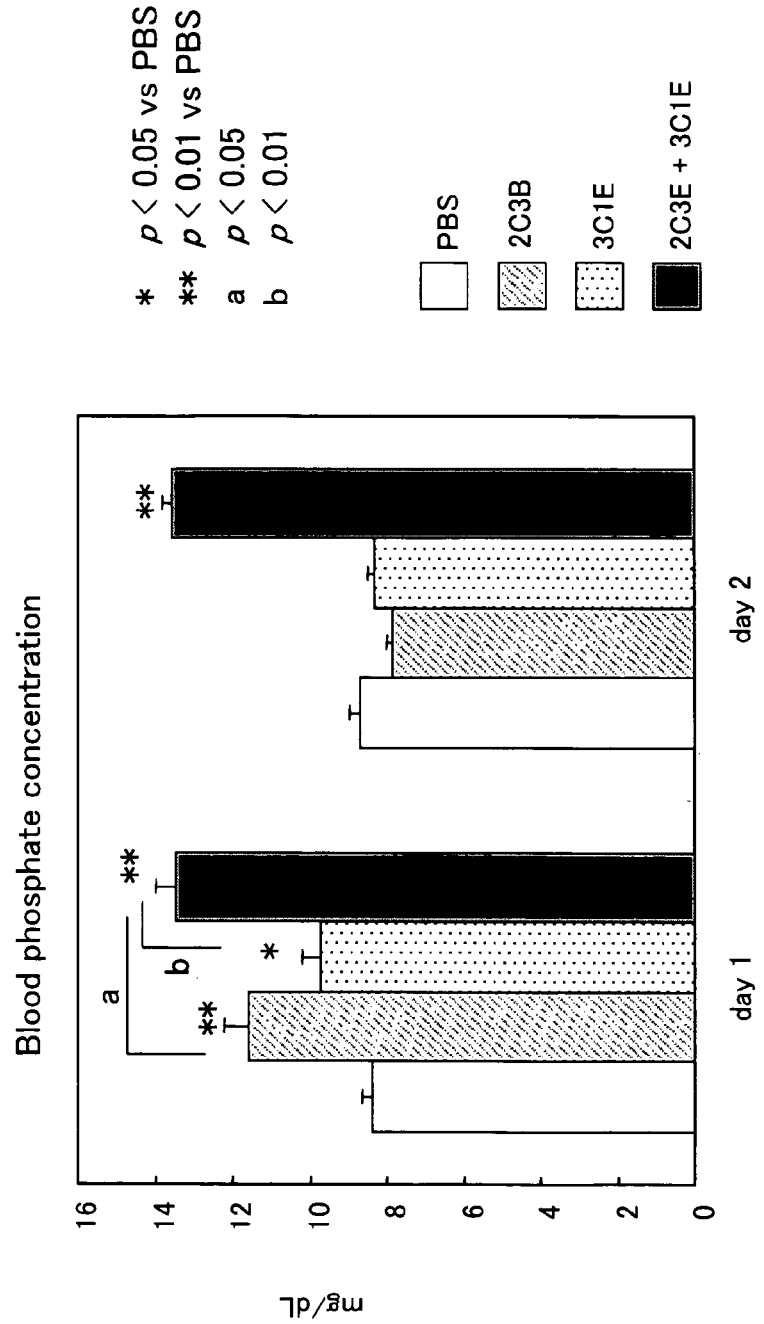
FIG. 24 shows serum phosphate concentrations on day 1 and day 2 after administering the mixture of 2 antibodies (2C3B and 3C1E antibodies) or a vehicle (PBS) to normal mice. Measured values are expressed with average value+/− standard deviation. "*" and "**" indicate p<0.05 and p<0.01, respectively, which are the results of tests of significance conducted by Student-t, compared with the group to which vehicles had been administered. "a" and "b" indicate p<0.05 and p<0.01, respectively, which are the results of tests of significance conducted by Student-t. (Example 31)

The obtained results are shown in FIG. 24. 100 µg of the 2C3B antibody or the 3C1E antibody alone caused a significant increase in serum phosphorus concentrations on day 1 after administration. On the other hand, in the group to which the mixture of the antibodies had been administered, although the dose of each antibody had been reduced by half, action to significantly increase serum phosphorus concentrations was shown, and significantly high serum phosphorus concentrations were shown compared with any group to which a single type of antibody had been administered. Furthermore, on day 2 after administration, whereas in the group to which the 2C3B antibody or the 3C1E antibody had been administered, action increasing serum phosphorus concentrations disappeared, serum phosphorus concentrations in the group to which the mixture of the antibodies had been administered were still significantly increased. The above results showed that the mixture of 2 types of antibodies recognizing different sites can further augment neutralization activity and maintain the action time longer than in cases where 1 type of antibody alone was administered.

Example 32

Experiment of Administration of FGF-23 Neutralization Antibodies to Hereditary Hypophosphatemia Model Mice As shown in Examples 23 and 30, increases in blood FGF-23 concentrations were shown in XLH and Hyp mice, suggesting the possibility that FGF-23 is a responsible factor of hypophosphatemia, abnormal vitamin D metabolism, or disorders of bone calcification, which are morbidities of the diseases. Hence, anti-FGF-23 neutralization monoclonal antibodies were administered to Hyp mice, and then whether or not the above morbidities could be improved was examined.

(1) Experiment of Repeated Administration of anti-FGF-23 Neutralization Antibodies Using 4- to 7-week-old male C57BL/6-Hyp mice and wild-type male C57BL/6 mice in same littermates, effects by the repeated administration of neutralization antibodies on blood phosphate concentrations and blood 1,25D concentrations in Hyp mice were examined. Four groups established in this experiment were composed of a group of wild-type mice to which vehicles were administered, a group of wild-type mice to which antibodies were administered, a group of Hyp mice to which vehicles were administered, and a group of Hyp mice to which antibodies were administered. Each group consisted of 4 mice. In the case of the groups to which antibodies were administered, specifically, the 3C1E antibody was admixed with the 2C3B antibody, so that each of their final concentrations would be 1.7 mg/ml, and then the resultant was administered at a dose of 17 mg/kg subcutaneously to the dorsal region of each mouse. 10 mg/kg PBS in a volume equivalent to that of antibodies administered to the groups to which the antibodies were administered was administered per mouse. On days 2, 4, and 6 after the initial administration, similar administration was performed. On days 1 and 7 after the initial administration, the ends of the tail portions were incised, and then partial blood collection was performed under ether anesthesia. For the measurement of blood phosphate and 1,25D concentrations, as well as blood total alkaline phosphatase activity, P (phosphorus)-Test Wako (trademark, Wako Pure Chemical Industries, Ltd., Japan), Calcium-Test Wako (trademark, Wako Pure Chemical Industries, Ltd., Japan), a 1,25(OH)2D RIA Kit TFB (TFB, U.S.A.), and Alkaline Phospha B-Test Wako (trademark, Wako Pure Chemical Industries, Ltd., Japan) were used, respectively.

Figure 25A:
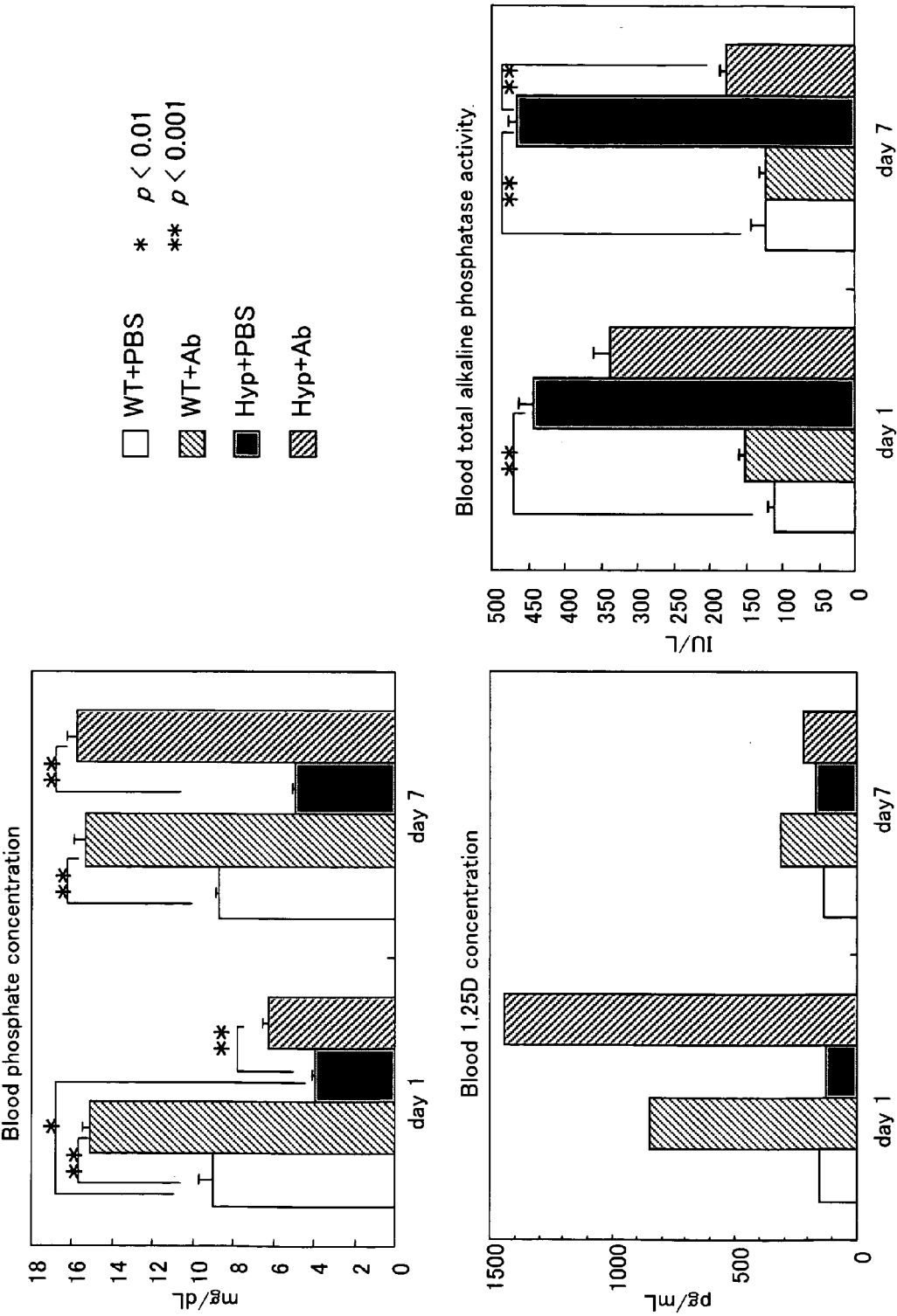
FIG. 25A shows blood phosphate concentrations, 1,25-dihydroxy vitamin D concentrations, and total alkaline phosphatase activity on days 1 and 7 after repeatedly administering the mixture of antibodies (Ab), comprised of the 2C3B antibody and the 3C1E antibody, or a vehicle (PBS) to wild-type mice (WT) and Hyp mice (Hyp). Blood phosphorus concentrations and alkaline phosphatase activity values are expressed with average value+/−standard deviation. "*" and "**" indicate p<0.01 and p<0.001, respectively, which are the results of tests of significance conducted by Student-t. Blood 1,25-dihydroxy vitamin D concentration was measured using plasma prepared by admixing an equivalent volume of plasma samples collected from each group. (Example 32)

The results are shown in FIG. 25A. In the group of wild-type mice to which the antibodies had been administered, significant increases were observed in serum phosphate concentrations during day 1 to day 7 after administration. In the group of Hyp mice to which the antibodies had been administered, significant increases were also observed in blood phosphate concentrations compared with those in the groups to which vehicles had been administered on day 1 after administration. These increases became more significant on day 7 after administration, showing concentrations to the same degree as those of the group of wild-type mice to which the antibodies had been administered. Moreover, by the administration of the neutralization antibodies, significant increases were observed in blood 1,25D concentrations on day 1 after administration in both wild-type mice and Hyp mice. In the meantime, abnormal increases in blood total alkaline phosphatase activity have been reported in Hyp mice or in patients with hyphophosphatemic rickets such as XLH. It was revealed that administration of the neutralization antibodies to Hyp mice attenuated, from 24 hours after the administration, this blood total alkaline phosphatase activity at abnormally higher levels than those in normal mice, and further caused the activity to significantly decrease to the same degree as that in wild-type mice on day 7 after initial administration.

Using 4- to 7-week-old male C57BL/6J-Hyp mice (Hyp mice) and wild-type male C57BL/6J mice (wild-type littermate mice) and of the normal control group, effects of repeated administration of anti-FGF-23 neutralization antibodies on the bone tissues of Hyp mice were examined. The four groups established in this experiment were: a group of wild-type mice to which vehicles were administered, a group of wild-type mice to which antibodies were administered, a group of Hyp mice to which a vehicle was administered, and a group of Hyp mice to which antibodies were administered. Each group consisted of 4 mice. In the case of the groups to which antibodies were administered, specifically, the 3C1E antibody was admixed with the 2C3B antibody, so that each of their final concentrations would be 1.7 mg/ml, and then the resultant was administered at a dose of 17 mg/kg subcutaneously to the dorsal region of each mouse. In the case of the group of mice to which vehicles were administered, specifically, 10 ml/kg PBS was administered subcutaneously to the dorsal region of each mouse. When the day of the initial administration is denoted day 0, on days 2, 4, 6, 8, 21, and 40, similar administration was performed. On day 49 after the initial administration, blood was collected from the heart under ether anesthesia, and right femur samples, and right tibia samples, costa samples were collected. X-ray magnified images of the excised femur, tibia, and costa samples were taken by X-ray irradiation using a μF FX-1000 Microfocus X-ray magnified imaging system (FUJI PHOTO FILM CO., LTD., Japan) under outgoing conditions of 100 μA and 25 kV for 5 seconds, and then obtained after digital imaging using a BAS imaging analyzer (FUJI PHOTO FILM CO., LTD., Japan).

Figure 27:
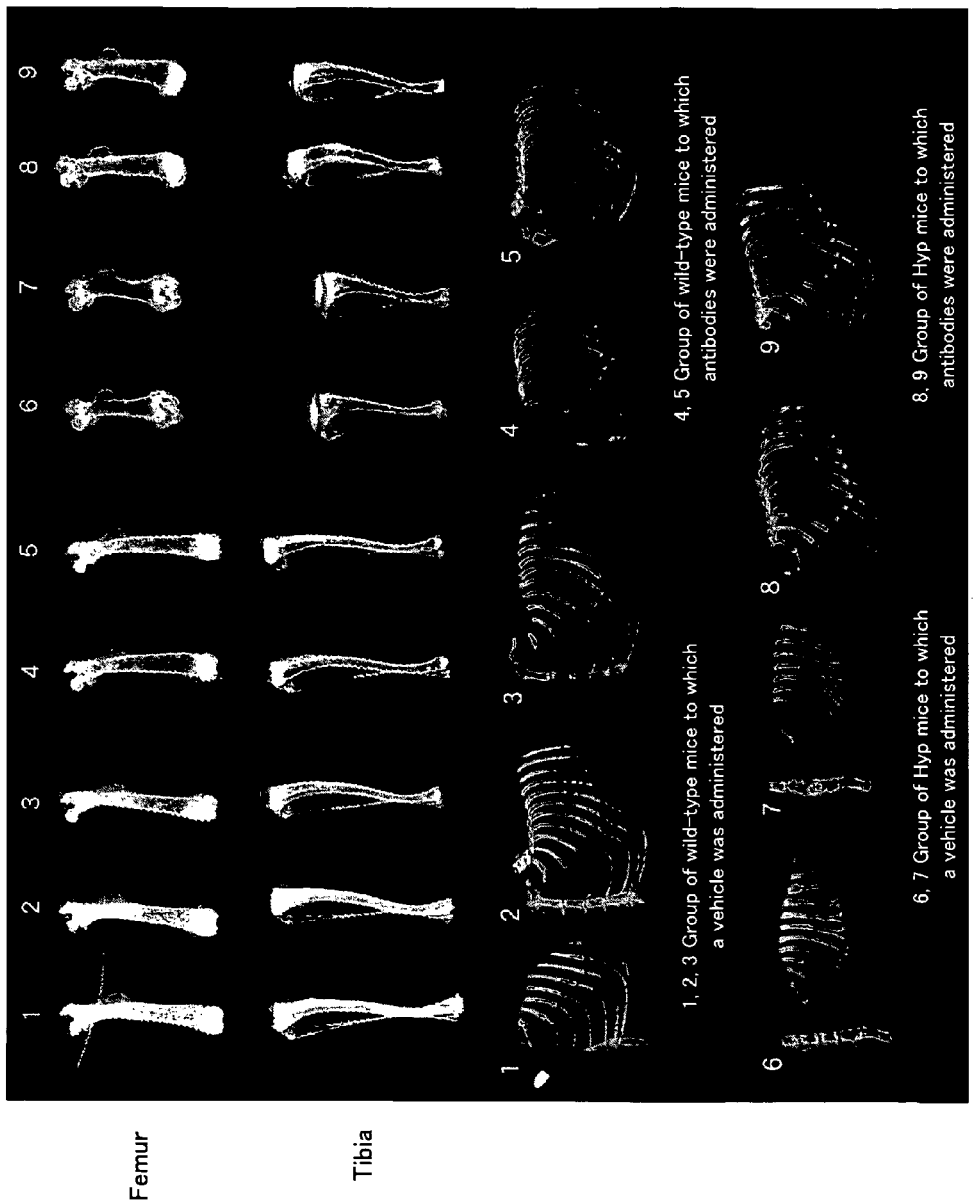
FIG. 27 shows magnified X-ray images of femora, tibiae, and costae extracted after administration of the mixture of antibodies (Ab), comprised of the 2C3B antibody and the 3C1E antibody, or a vehicle (PBS) to wild-type mice (WT) and Hyp mice (Hyp). (Example 32)

The thus obtained X-ray magnified images of extracted femora, tibiae, and costae are shown in FIG. 27. In Hyp mice or in the case of hypophosphatemic rickets such as XLH, increased chondrocytes observed in association with calcification disorders and enlargement of the metaphysis of long bones or osseocartilaginous junction in costae have been reported. As a result of X-ray imaging analysis, alleviation was recognized in the group of Hyp mice to which the antibodies had been administered for enlargement of the metaphysis, decreased bone density, and thinning of cortical bones of the femora and tibia that were recognized in the group of mice to which the vehicles were administered. Furthermore, alleviation was also recognized in the group of Hyp mice to which the antibodies had been administered for failure of extension in the longitudinal direction of femora and tibia observed in the group of Hyp mice to which the vehicle had been administered. Moreover, enlargement of the junctions of costae and of costal cartilages observed in the group of Hyp mice to which the vehicle had been administered disappeared in the group of Hyp mice to which the antibodies had been administered. It was revealed that repeated administration of anti-FGF-23 neutralization antibodies to Hyp mice improves disorders of bone extension and disorders of bone calcification.

Figure 28:
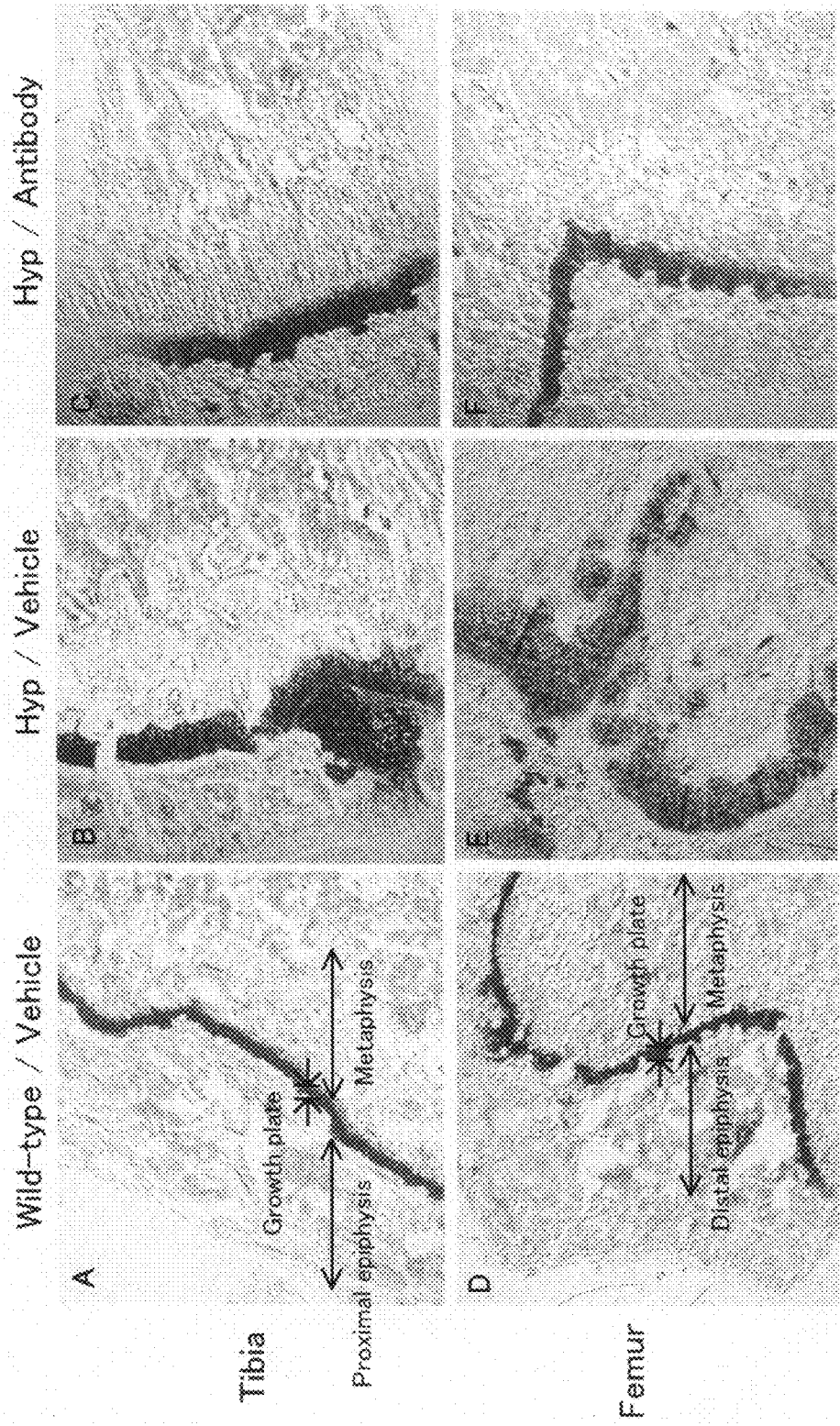
FIG. 28 shows comparison of images of bone tissues of the proximal part of the tibia and the distal part of the femur of Hyp mice (Hyp/antibody) to which the mixture of antibodies (the 2C3B antibody and the 3C1E antibody) was repeatedly administered, with images of the tissues of the relevant regions of Hyp (Hyp/vehicle) and wild-type mice (Wild-type/vehicle) to which vehicles were administered. The extracted tibiae and femora were subjected to Villanueva Bone staining. They were resin-embedded, and then prepared to result in 5 μm-thick nondecalcification sections. These samples were stained differently: osteoid is purple, calcified bone is light orange, low-calcified bone is light brown, and embedded cells are light purple under visible light. (Example 32)

Furthermore, for the purpose of examining in detail the action of the anti-FGF-23 antibodies on bone tissues, bone tissue samples of animals subjected to this experiment were prepared. After sacrifice, the left tibiae and the left femora were extracted, fixed with 70% ethanol, subjected to Villanueva Bone staining (Villanueva Bone Stain Powder, MARUTO INSTRUMENT CO., LTD. Japan), dehydrated with ethanol solutions having sequentially elevated concentrations, and then embedded in Technovit 7100 (Kulzer, Germany). The resultants were sectioned to have an approximate thickness of 5 μm, and then the sections of the proximal region of the tibia and the distal region of the femora were observed under a microscope. The images of the bone tissue samples are shown in FIG. 28. Whereas growth plates where chondrocytes are aligned in an orderly manner were observed in wild-type mice (FIGS. 28A and D), in the bone tissues of Hyp mice, regions with a disturbed column structure, characterized by enlarged regions of the growth plates and irregular sequences of chondrocytes (FIGS. 28B and E) were observed. In contrast, in Hyp mice to which the neutralization antibodies against FGF-23 had been repeatedly administered, suppressed enlargement of the width of the growth plate and disappearance of the irregular sequences of chondrocyts were observed (FIGS. 28C and F).

(2) Experiment of Single Administration of Anti-FGF-23 Neutralization Antibodies Using 12- to 20-week-old male C57BL/6-Hyp mice and wild-type male C57BL/6 littermate mice, effects of single administration of neutralization antibodies on blood phosphate concentrations and blood 1,25D concentrations in Hyp mice were examined. The four groups established in this experiment were: a group (n=4) of wild-type mice to which a vehicle was administered, a group (n=5) of wild-type mice to which antibodies were administered, a group (n=3) of Hyp mice to which a vehicle were administered, and a group (n=3) of Hyp mice to which antibodies were administered. In the case of the groups to which antibodies were administered, specifically, the 3C1E antibody was admixed with the 2C3B antibody, so that each of their final concentrations would be 1.7 mg/ml, and then the resultant was administered once at a dose of 17 mg/kg subcutaneously to the dorsal region of each mouse. In the case of the group of mice to which a vehicle was administered, specifically, PBS was administered at a dose of 10 ml/kg. On day 4 after administration, blood was collected from the hearts and the kidneys were extracted under ether anesthesia.

Figure 25B:
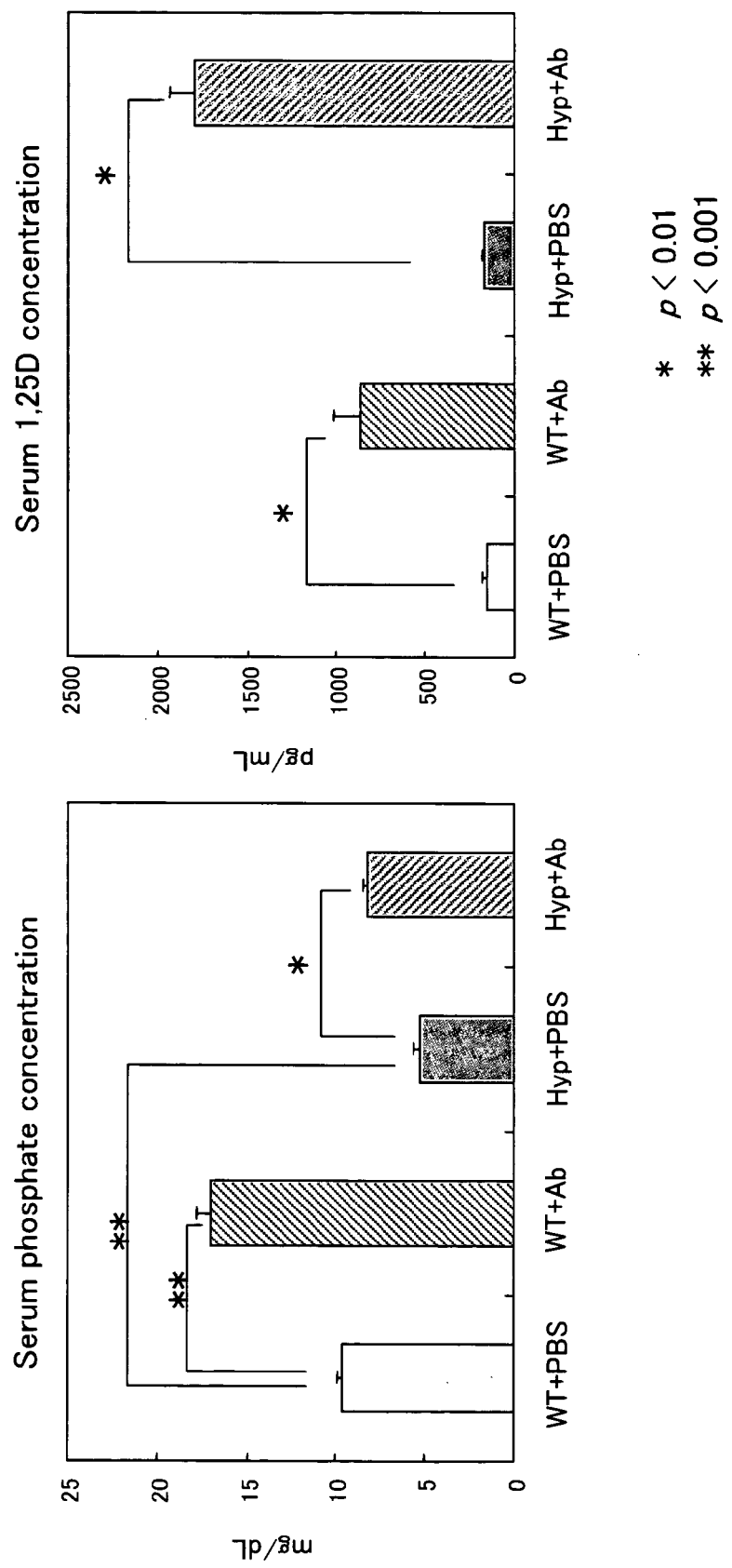
FIG. 25B shows blood phosphate concentrations and 1,25-dihydroxy vitamin D concentrations on day 4 after single administration of the mixture of antibodies (Ab), comprised of the 2C3B antibody and the 3C1E antibody, or a vehicle (PBS) to wild-type mice (WT) and Hyp mice (Hyp). Results are expressed with average value +/− standard deviation. "*" and "**" indicate p<0.01 and p<0.001, respectively, which are the results of tests of significance conducted by Student-t. (Example 32)

The thus obtained results of measuring serum phosphate and 1,25D concentrations are shown in FIG. 25B. By the single administration of the antibodies to wild-type mice, both serum phosphate and 1,25D showed significant increases on day 4. This effect of increasing the concentrations was also observed in Hyp mice. By the administration of the antibodies, the serum phosphate concentration was corrected from the lowered level to the normal level and the 1,25D concentration showed a significant increase.

(3) Effect of Controlling the Expression of NaPi2a and 1αOHase by Anti-FGF-23 Neutralization Antibodies A serum phosphate concentration is determined by the reabsorption rate by sodium-dependent phosphate cotransporters (NaPi2a) that are mainly present in the renal proximal tubule. Furthermore, it has already been reported that the reabsorption rate is controlled depending on the expression level of NaPi2a itself or the localization ratio of NaPi2a protein. Hence, whether or not the effect of anti-FGF-23 neutralization antibodies to increase serum phosphate concentrations is mediated by NaPi2a was examined.

Renal proximal tubule brush border membrane vesicles (BBMV) where the NaPi2a was localized were prepared using a kidney subjected to freeze-thawing, according to a calcium precipitation method as previously reported by Katai et al. in J. Biol. Chem. 274, pp. 28845-28848, 1999. 20 µg of each obtained BBMV was subjected to Western blotting according to the method described in Example 16. The NaPi2a protein was detected using anti-mouse NaPi2a rabbit polyclonal antibodies purified from anti-serum that had been obtained by immunizing rabbits similarly to the case of Example 5 with the C-terminal partial peptide (SEQ ID NO: 32) of a mouse NaPi2a protein. The results are shown in FIG. 25C. It has already been reported that NaPi2a protein levels are significantly lowered in the BBMV of Hyp mice. However, by the administration of anti-FGF-23 neutralization antibodies, the expression of the NaPi2a was significantly increased.

Also in the wild-type mice, further increase was observed in the NaPi2a protein concentrations. Moreover, the phosphate transport activity by the NaPi2a protein was measured using the above BBMV. Using 0.1 mg of each BBMV prepared from each individual, sodium-dependent phosphate-uptake activity for 60 seconds was measured by a rapid filtration method. Reagent and reaction conditions were employed according to the method as reported by Katai et al. in J. Biol. Chem. 274, pp. 28845-28848, 1999.

As a result, as shown in FIG. 25C, increases in phosphate transport activity resulting from the administration of the antibodies were observed in both wild-type mice and Hyp mice. These results suggested that the action of increasing serum phosphate concentrations in wild-type mice or Hyp mice by the anti-FGF-23 neutralization antibodies is caused by increase of the levels of NaPi2a protein existing in the renal proximal tubule. mNpt2C: LALPAHHNATRLC (SEQ ID NO: 32)

Figure 25D:
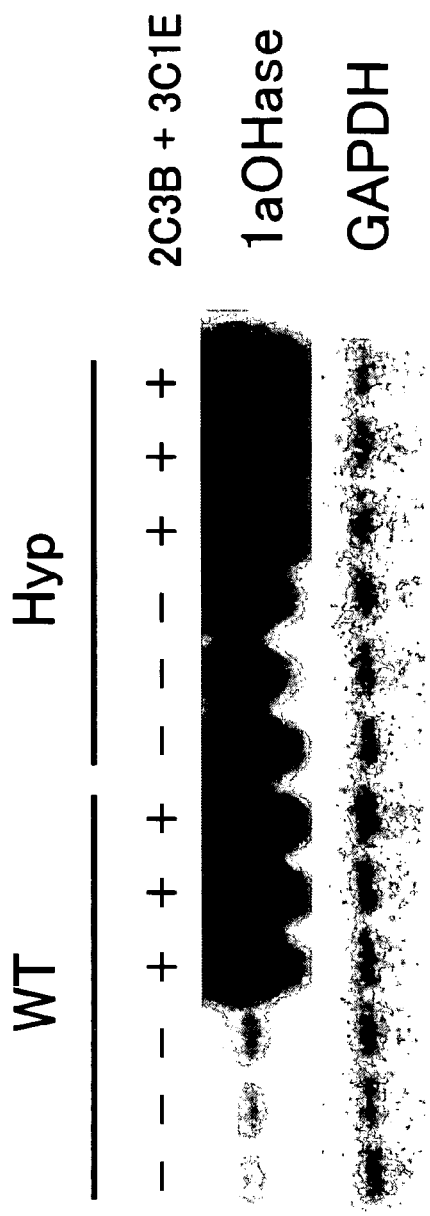
FIG. 25D shows changes in the expression of a 1αOHase gene as analyzed by Northern blotting using RNA prepared from the kidney on day 4 after single administration of the mixture of antibodies (Ab), the 2C3B antibody and the 3C1E antibody, or a vehicle (PBS) was performed for wild-type mice (WT) and Hyp mice (Hyp). (Example 32)

Next, to elucidate the mechanism of action to increase serum 1,25D concentrations, the expression pattern of kidney 25 hydroxyvitamin D-1α hydroxylase (1αOHase) was analyzed. Total RNA was extracted using an ISOGEN reagent (NIPPON GENE CO., LTD., Japan) from a frozen kidney. 20 µg of each obtained RNA was subjected to Northern blotting according to the standard method. A PerfectHyb reagent (Toyobo Co., Ltd., Japan) was used for hybridization, and reaction and washing of blots were conducted according to the attached documents. A probe used herein was prepared by amplifying a mouse 1αOHase partial cDNA by the PCR method using cDNA library prepared from a mouse kidney as a template, and oligonucleotides represented by SEQ ID NOS: 33 and 34 as primers, or amplifying as an internal standard a glyceraldehyde-3-phosphate dehydrogenase (GAPDH) partial cDNA by the PCR method using oligonucleotides represented by SEQ ID NOS: 35 and 36 as primers, and then labeling the cDNA with $^{32}P$ using a Megaprime DNA labeling system (Amersham bioscience, U.S.A.). Signal detection was performed using a BAS imaging analyzer (FUJI PHOTO FILM CO., LTD., Japan). The results are shown in FIG. 25D. By the administration of the neutralization antibodies, significantly enhanced expression of 1αOHase was confirmed in wild-type mice and Hyp mice. These results suggested that the action of the anti-FGF-23 neutralization antibodies to increase serum 1,25D concentrations in wild-type mice or Hyp mice was due to enhanced gene expression levels of 1αOHase existing in the kidney.

m1alphaFW: cagacagagacatccgtgtag (SEQ ID NO: 33)
m1alphaRV: ccacatggtccaggttcagtc (SEQ ID NO: 34)
gapdhFW: accacagtccatgccatcac (SEQ ID NO: 35)
gapdhRV: tccaccaccctgttgctgta (SEQ ID NO: 36)

The above results suggested that FGF-23 is strongly involved in decreases in blood phosphate concentrations and blood 1,25D concentrations in Hyp mice, that is, in the case of human XLH, and suggested the possibility that inhibition of the FGF-23 action by the administration of the anti-FGF-23 antibodies can improve the morbidity thereof. Moreover, abnormally high levels of blood total alkaline phosphatase activity in Hyp mice along with disorders of bone extension and disorders of bone calcification were also normalized by the administration of the anti-FGF-23 antibodies. Hence, remission of osteomalacia accompanied by normalization of bone remodeling is expected.

Example 33

Action of Anti-FGF-23 Antibody (3C1E) on Bone Remolding

Figure 26:
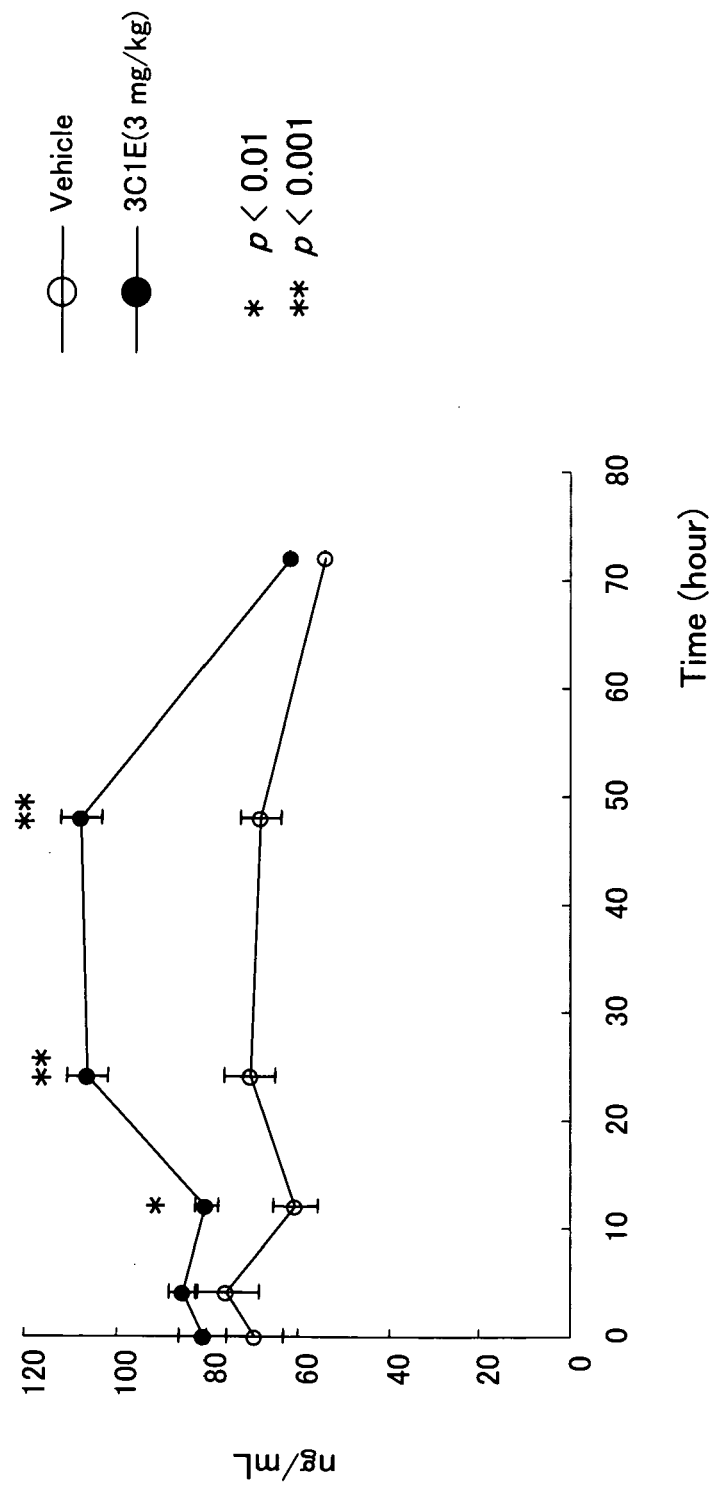
FIG. 26 shows changes with time in blood osteocalcin concentrations when the 3C1E antibody or a vehicle was administered to normal rats. Results are expressed with average value+/−standard deviation. "*" and "**" indicate p<0.01 and p<0.001, respectively, which are the results of tests of significance conducted by Student-t. (Example 33)

As described in Example 32(1), the action of the anti-FGF-23 antibodies on bone remodeling was suggested. To further examine this suggestion, changes in serum osteocalcin concentrations after administration of the anti-FGF-23 antibodies were analyzed with time. The experiment was conducted as follows. Single administration of the 3C1E antibody at 3 mg/kg, or that of vehicles (PBS) at 1.1 ml/kg was performed via the caudal veins of 7-week-old male S.D. rats. At 4, 12, 24, 48, and 72 hours after administration, blood was partially collected from the caudal arteries, and then serum was prepared. Serum osteocalcin concentrations were measured using an osteocalcin ELISA kit (Amersham bioscience, Japan). The results are shown in FIG. 26. At 12, 24, and 48 hours after administration of the antibodies, significant increases were observed in serum osteocalcin concentrations. These results suggested the possibility that the administration of the anti-FGF-23 antibodies can have a direct or indirect effect on bone remodeling.

Example 34

Action of Anti-FGF-23 Neutralization Antibodies (Mixture of 2C3B and 3C1E Antibody) on Osteoporosis Model Mice For the purpose of further examining the action of the anti-FGF-23 neutralization antibodies on bone metabolism as described in Example 33, the action of the anti-FGF-23 antibodies on post-ovariectomy reduced-bone-mass model mice that were thought to reflect reduced bone mass observed in the case of postmenopausal osteoporosis was examined. Ovaries were extracted from 8-week-old female ddy mice, and the mice were divided into 2 groups: a group to which a vehicle was administered, and a group to which the anti-FGF-23 antibodies were administered. In addition, as an operation control group, a sham operation group subjected to sham operation was established. For the group (n=10) to which the antibodies were administered, administration was begun on day 3 after operation, and anti-FGF-23 antibodies prepared by mixing an equivalent volume of the 2C3B antibody and the 3C1E antibody (3 mg/kg; 1.5 mg/kg each of the 2C3B antibody and the 3C1E antibody) were administered subcutaneously to the dorsal region of the mice 3 times a week for 4 weeks. Furthermore, to the group (n=9) of mice to which a vehicle was administered and the group (n=10) of mice which were subjected to sham operation, PBS was administered as a vehicle in the same quantity (10 ml/kg) as that of the solution of the antibodies. On week 2 after ovariectomy, blood was collected from the eye sockets under ether anesthesia, and on week 4 after ovariectomy, blood was collected from the hearts under ether anesthesia. Serum was prepared from the collected blood by centrifugation at 8000 rpm×10 minutes, and then subjected to the measurement of serum osteocalcin (IRMA kit, Immutopics, Inc.). After sacrifice by collecting blood from the hearts on week 4 after ovariectomy, the femora were extracted, and then bone mineral content and bone mineral densities (Bone Densitometer, Model DCS-600, ALOKA CO., LTD.) were measured.

As shown in FIGS. 29A and B, in both cases on weeks 2 and 4 after ovariectomy, significantly increased serum osteocalcin levels were was observed in the group to which the anti-FGF-23 antibodies (the mixture of 2C3B and 3C1E) had been repeatedly administered, compared with those in the group to which the vehicle had been administered. Osteocalcin is a protein that is specifically produced by osteoblasts. Since elevated levels of serum osteocalcin in vivo are thought to be an indicator of bone formation, a possibility was shown that the administration of the anti-FGF-23 antibodies promotes bone formation.

Figure 30B:
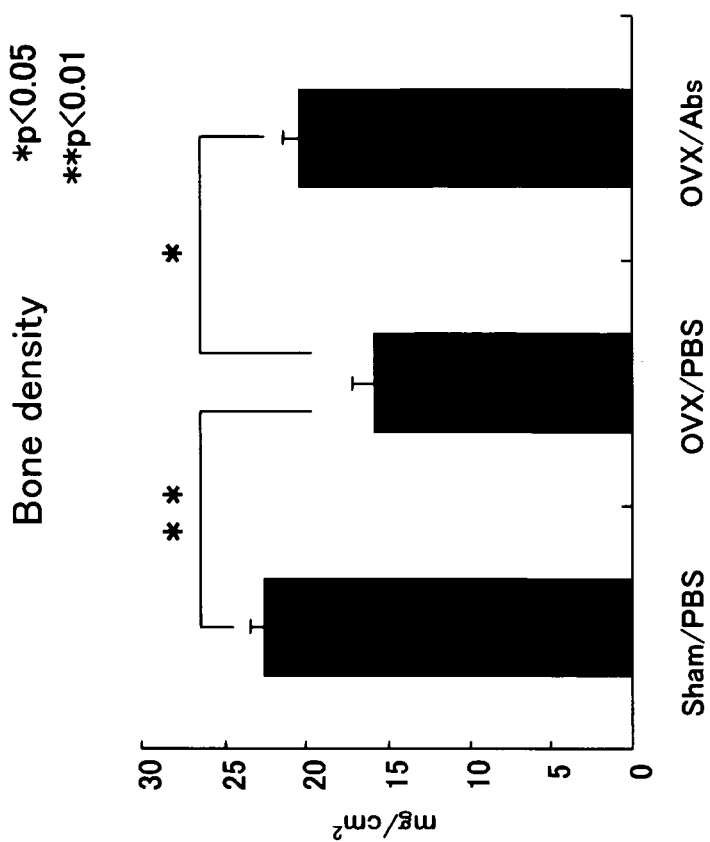
FIG. 30B shows bone densities (Bone Densitometer, Model DCS-600, ALOKA CO., LTD.) on week 4 after ovariectomy of established groups: a group (sham/PBS) of mice subjected to sham operation to which a vehicle (PBS) was administered, a group (OVX/Abs) of mice subjected to ovariectomy to which the mixture of antibodies, comprised of the 2C3B antibody and the 3C1E antibody, were administered, or a group (OVX/PBS) of mice subjected to ovariectomy to which a vehicle (PBS) was administered. Bone-salt quantities and bone densities of the femora are expressed with average value+/−standard error. "*" and "**" indicate p<0.05 and p<0.01, respectively, which are the results of tests of significance conducted by Student-t. (Example 34)
Figure 30A:
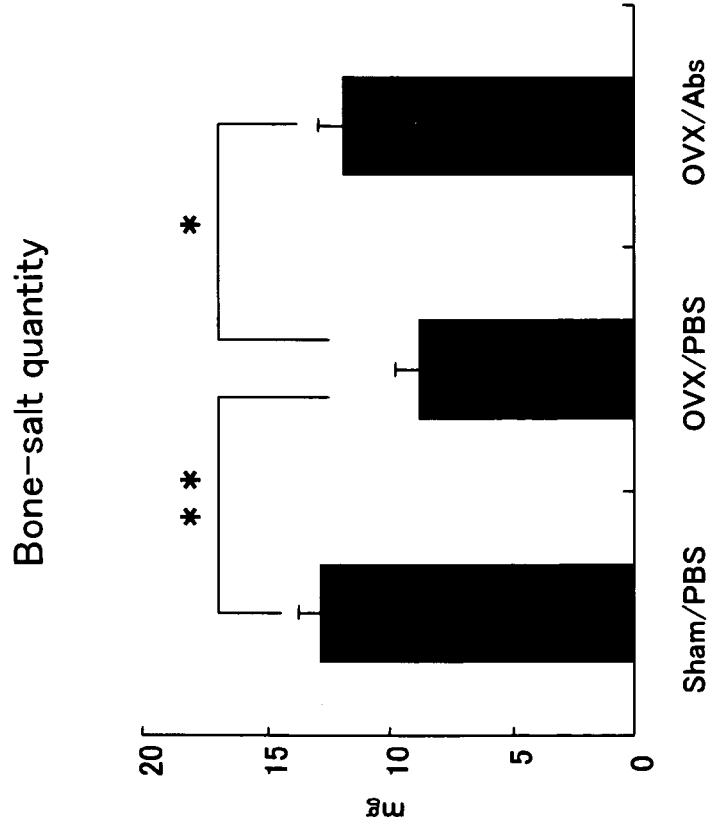
FIG. 30A shows bone-salt quantities in the femora on week 4 after ovariectomy of established groups: a group (sham/PBS) of mice subjected to sham operation to which a vehicle (PBS) was administered, a group (OVX/Abs) of mice subjected to ovariectomy to which the mixture of antibodies comprised of the 2C3B antibody and the 3C1E antibody, were administered, or a group (OVX/PBS) of mice subjected to ovariectomy to which a vehicle (PBS) was administered. Bone-salt quantities and bone densities of the femora are expressed with average value+/−standard error. "*" and "**" indicate p<0.05 and p<0.01, respectively, which are the results of tests of significance conducted by Student-t. (Example 34)

Moreover, as shown in FIGS. 30A and B, the group which had been subjected to overiectomy and to which the vehicle had been administered showed significantly reduced bone quantity compared with the group which had been subjected to sham operation and to which the vehicle had been administered. In contrast to the significantly decreased bone mineral content and bone mineral density by ovariectomy, the group which had been subjected to overiectomy and to which the anti-FGF-23 antibodies had been administered showed significantly high levels of bone mineral content and bone mineral density. Based on these results, it was considered that the administration of anti-FGF-23 antibodies suppressed the reduction in bone quantity resulting from overiectomy.

Example 35

Experiment of Administration of Anti-FGF-23 Neutralization Antibodies (Mixture of 2C3B Antibody and 3C1E Antibody) to Hereditary Hypophosphatemic Rickets Model Mice As shown in Example 32, the anti-FGF-23 neutralization antibodies were shown to alleviate disorders of bone extension and disorders of bone calcification in Hyp mice. Hence, the action of the above anti-FGF-23 neutralization antibodies on disorders of bone extension and disorders of bone calcification in Hyp mice was further examined in detail using 4-week-old male C57BL/6-Hyp mice and wild-type male C57BL/6 littermate mice that were younger in week age than mice used in Example 32, and thus were growing significantly. Four groups established in this experiment were: a group of wild-type mice to which a vehicle (PBS) was administered, a group of Hyp mice to which a vehicle (PBS) was administered, a group of Hyp mice to which antibodies were administered at a low dose, and a group of Hyp mice to which antibodies were administered at a high dose. Each group consisted of 6 to 7 mice. As neutralization antibodies, a solution containing a mixture of the 2C3B antibody and the 3C1E antibody at the same concentration to each other was used. The solution was prepared so that the total quantity of the 2 types of antibodies was 4 mg/kg for the low-dose group and 16 mg/kg for the high-dose group. The neutralization antibodies or the vehicle was repeatedly administered subcutaneously at a volume of 10 mL/kg to the dorsal region of each mouse on days 7, 14, 21, and 28 when the day of the initial administration was denoted day 0. Body weight, the length of the tail, and thel length of the tibia were measured on the day same as the day on which the antibodies were administered. Furthermore, on day 31 after the initial administration, mice were sacrificed by collecting blood from the hearts under ether anesthesia, and then the femora and the tibiae on the left and the right were extracted.

Figure 31B:
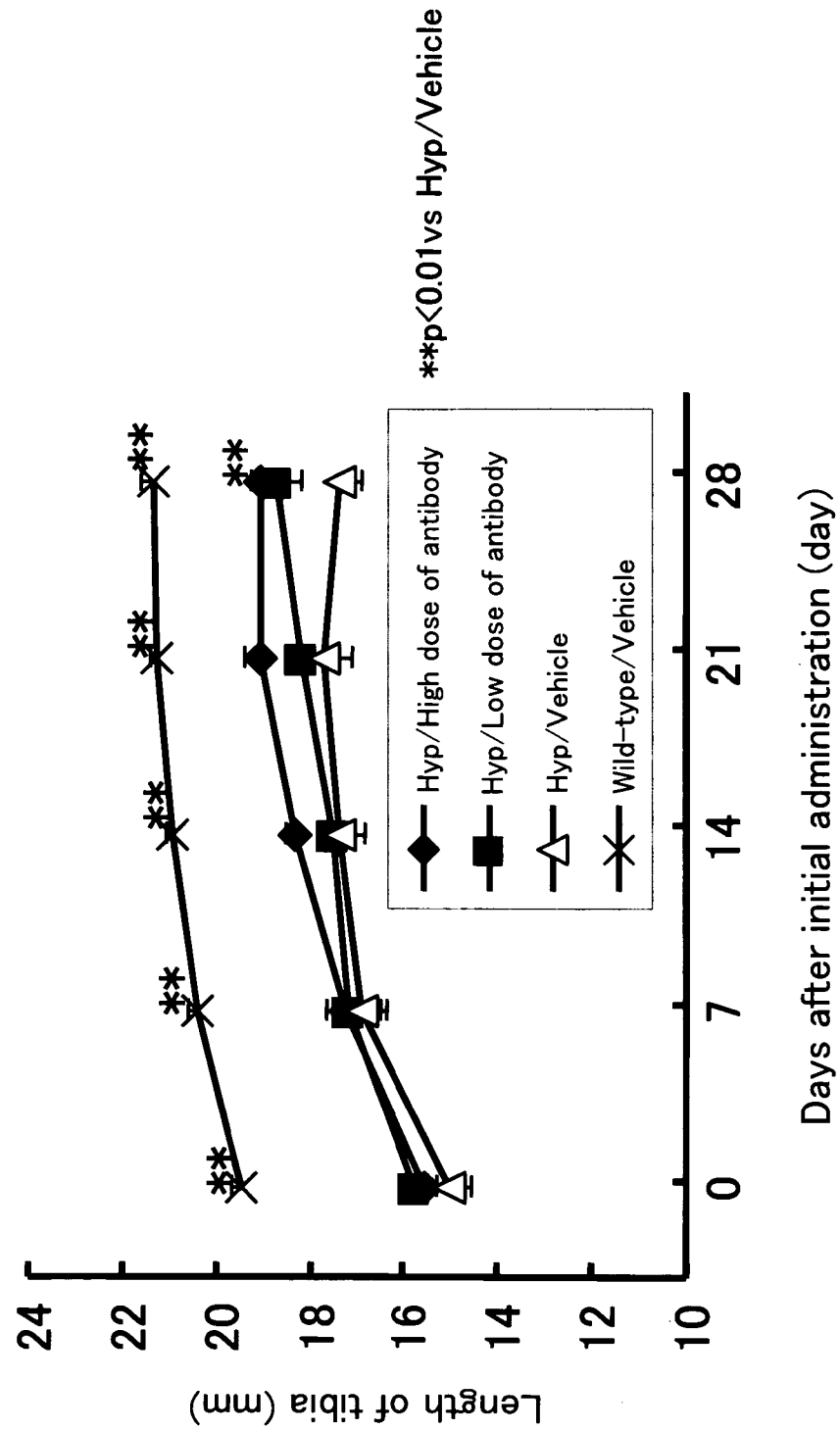
FIG. 31B shows the lengths of tibia as periodically measured after repeated subcutaneous administration (once a week) of a vehicle to Hyp mice (Hyp/vehicle), the mixture of antibodies, comprised of the 2C3B antibody and the 3C1E antibody, at 4 mg/kg to Hyp mice (Hyp/low dose of antibodies), or the same mixture at 16 mg/kg to Hyp mice (Hyp/high dose of antibodies), and a vehicle to wild-type mice (wild-type/vehicle). Results are expressed with average value+/−standard deviation. "**" indicates p<0.01 which is the result of a test of significant conducted by Student-t, when compared with the Hyp group to which a vehicle was administered. (Example 35)

(1) Action of Anti-FGF-23 Neutralization Antibodies to Extend the Length of the Tail and the Length of Tibia and to Increase Body Weight The bones of Hyp mice present rachitic bone phenotypes accompanied by characteristic impaired bone development such as disorders of extension of long bones in the longitudinal direction. As an individual mouse, an Hyp mouse is obviously shorter in body length and of lower in body weight than wild-type mice. To examine the effect of the administration of the anti-FGF-23 neutralization antibodies on such impaired bone development in Hyp mice, measurement of the length of the tail portion and the length of the tibia and changes in body weight in Hyp mice used in the experiment were examined. The results are shown in FIGS. 31A, B, and C. Also in this experiment, in contrast to normal mice, Hyp mice presented significantly low degrees of extension of the tail portions and of tibiae, and low body weights. Furthermore, compared with the group of Hyp mice to which the vehicle had been administered, the neutralization antibodies administered to Hyp mice exerted action to extend the length of the tail portions and the length of the tibiae and action to increase body weights in a dose-dependent manner.

(2) Bone Calcification Action by Anti-FGF-23 Neutralization Antibodies

Figure 32:
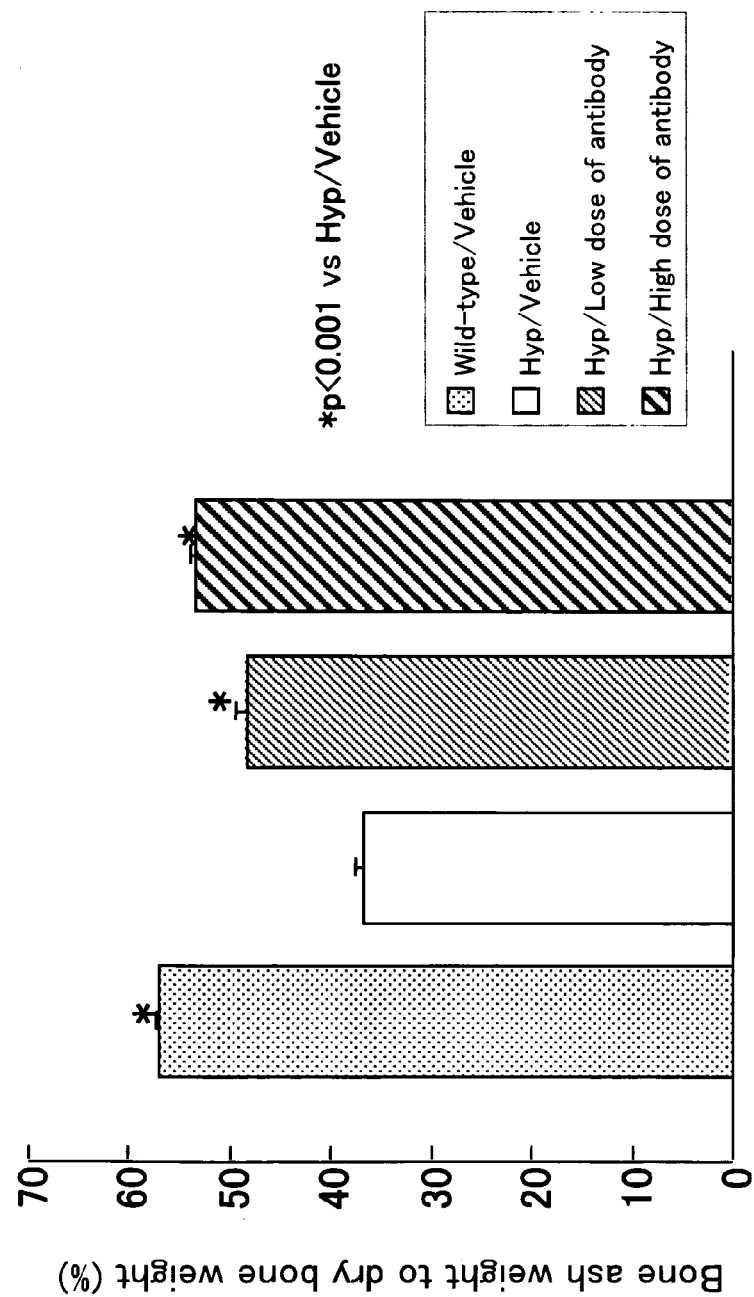
FIG. 32 shows the proportions of bone ash weight in dry bone weight when the femora were extracted and incinerated on day 31 after repeated subcutaneous administration (once a week) of a vehicle to Hyp mice (Hyp/vehicle), the mixture of antibodies, comprised of the 2C3B antibody and the 3C1E antibody, at 4 mg/kg to Hyp mice (Hyp/low dose of antibodies), or the same mixture of antibodies at 16 mg/kg to Hyp mice (Hyp/high dose of antibodies), and a vehicle to wild-type mice (wild-type/vehicle). Results are expressed with average value+/−standard deviation. "*" indicates p<0.001 which is the result of a test of significant conducted by Student-t, when compared with the Hyp group to which a vehicle was administered.

The bone tissue of Hyp mice is known to be rich in terms of the proportions of uncalcified and low-calcified bone, but in poor in mineral content compared with the case of a normal mouse. Hence, it was examined whether or not action of the anti-FGF-23 neutralization antibodies to increase the bone mineral content in the Hyp mouse femora could be obtained. In this experiment, the extracted left femora were dried with a dryer at 100° C. for 12 hours, and then weighed, thereby obtaining the dried bone weight. Next, the dried bone was incinerated by heating in a muffle furnace at 600° C. for 12 hours. The resultants were weighed so as to obtain bone ash weights. The results are shown in FIG. 32. The ratio of bone ash weight to dried bone weight was very low in Hyp mice, compared with the case of wild-type mice. The ratio of bone ash weight to dried bone weight in the group of Hyp mice to which the antibodies had been administered significantly increased in a manner depending on the dose of the neutralization antibodies repeatedly administered. In particular, the group to which the antibodies had been administered at a high dose showed improvement to the extent of showing values at almost the same levels as those in the group of wild-type mice.

These results reveled that inhibiting the action of FGF-23 by the administration of anti-FGF-23 neutralization antibodies can improve disorders of bone extension and disorders of bone calcification presented by Hyp mice.

Example 36

Figure 33:
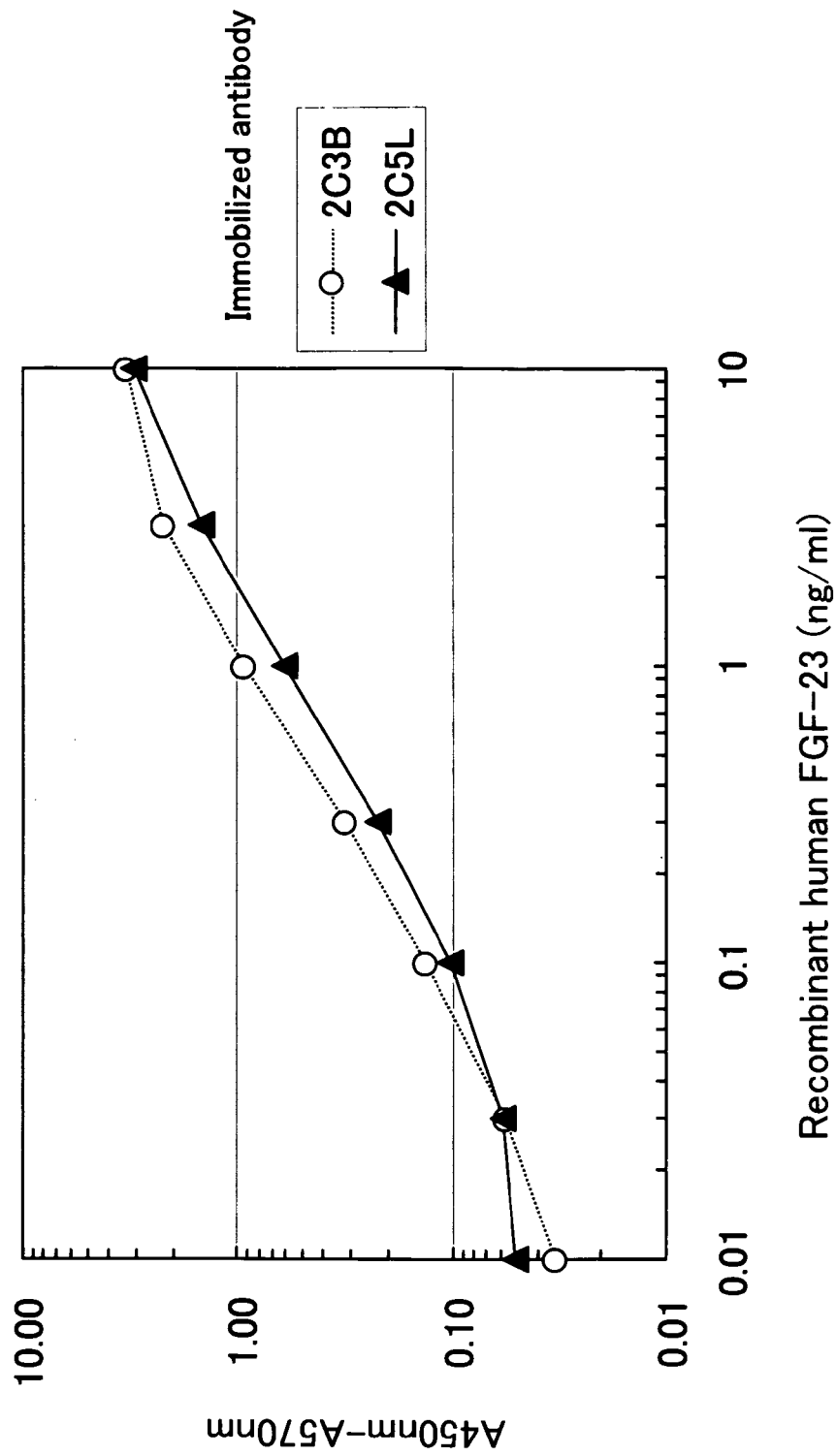
FIG. 33 shows the results of quantitatively measuring purified FGF-23 protein by the ELISA system using the 2C3B or the 2C5L antibody as an immobilized antibody, and the 3C1E antibody as an antibody for detection. (Example 36)

Quantitative Measurement of Human FGF-23 Protein by Sandwich ELISA Method Using 2C5L Antibody The 2C5L antibody produced by the 2C5L cloned hybridoma obtained in Example 3 was purified according to Example 4. Analysis of the recognition site thereof by the method described in Example 10 revealed that the 2C5L antibody has a recognition site within the N-terminal side fragment polypeptide corresponding to a region between the 25th and the 179th amino acid residues of SEQ ID NO: 1 in the same manner as the 2C3B antibody, and forms an immunocomplex with the N-terminal side fragment polypeptide and a full-length FGF-23 protein. Moreover, in a manner described in Example 12, establishment of a sandwich ELISA method using a combination of the 2C5L antibody and the 2C3B antibody was attempted. Upon binding of each antibody with the FGF-23 protein, both antibodies were shown not to competitively inhibit each other. According to this result, the 2C5L antibody has a recognition site within the N-terminal side fragment polypeptide corresponding to a region between the 25th to 179th amino acid residues, but the recognition site thereof is different from that of the 2C3B antibody having a recognition site also within the N-terminal side fragment polypeptide. This revealed that an ELISA method using a combination of the two types of antibodies is possible. Next, by the method described in Example 13, the ability to detect FGF-23 protein was examined when biotin-labeled 3C1E antibody was used as antibodies for detection, and the 2C3B or 2C5L antibodies were used as immobilized antibodies. The results are shown in FIG. 33. It was confirmed that the 2C5L antibody, in concentrations ranging from 10 pg/ml to 10 ng/ml, recognizes purified products of recombinant human FGF-23 in a concentration-dependent manner.

Example 37

Cross Reactivity Between 2C5L Antibody and Mouse FGF-23

In the sandwich ELISA system using a combination of the 2C3B antibody and the 3C1E antibody as shown in Examples 22 and 23, mouse FGF-23 could also been recognized similarly to human FGF-23. Hence, whether or not the 2C5L antibody could recognize mouse FGF-23 was examined. Similarly to Example 24, mouse serum with high levels of blood FGF-23 was obtained and then measured with a combination of the 2C3B and biotin-labeled 3C1E antibody, thereby obtaining a sample showing approximately 600 pg/ml. For this sample, a sandwich ELISA system similar to that in Example 36 was examined using a combination of the 2C5L antibody and the biotin-labeled 3C1E antibody. However, no reactivity was observed. This result showed that the 2C5L antibody has strong binding ability to human FGF-23, but has very weak or no binding ability to mouse FGF-23.

Example 38

Measurement of Ability of Neutralization Activity of 2C5L Antibody for Human FGF-23

The results in Example 37 suggested that since the binding ability of the 2C5L antibody to mouse FGF-23 is very low compared with that of the 2C3B antibody or the 3C1E antibody, the ability of neutralization activity of the 2C5L antibody for mouse endogenous FGF-23 would also not be significant. However, according to the result in Example 36, since the 2C5L antibody has strong binding ability to human FGF-23, the 2C5L antibody may have the ability of neutralization activity for human endogenous FGF-23. To verify the possibility, a system for measuring activity to neutralize human FGF-23 using animals was constructed by the following procedures, and then the activity of the 2C5L antibody to neutralize human endogenous FGF-23 was examined using this system.

An osmotic mini pump (alzet micro-osmotic pump model 1007D, DURECT, Canada) that had been adjusted to gradually release human FGF-23 recombinants at a dose of 1.2 μg/day was transplanted subcutaneously into the dorsal region of a 7-week-old male C57BL/6 mouse, thereby constructing a model to which the human FGF-23 recombinant was continuously administered. An anti-FGF-23 neutralization antibody containing 2C5L or a vehicle was administered intraperitoneally on day 3 after the transplantation of the pump, and then whether or not the action of the continuously existing human FGF-23 recombinant to decrease serum phosphate concentration could be suppressed was examined. The four groups established in this experiment were: a group (untreated/vehicle) of untreated mice to which a vehicle was administered, a group (FGF-23/vehicle) of the human-FGF-23-recombinant-continuously-administered model mice to which a vehicle was administered, a group (FGF-23/2C5L) of the human-FGF-23-recombinant-continuously-administered model mice to which the 2C5L antibody was administered, and a group (FGF-23/2C3B) of the human-FGF-23-recombinant-continuously-administered model mice to which the 2C3B antibody was administered. PBS was used as vehicle and for diluting the antibody. Anti-FGF-23 neutralization antibodies were administered at a dose of 20 mg/kg. The vehicle and the neutralization antibody were administered at a volume of 0.1 mL per 10 g of body weight. Before antibody administration and 24 hours after antibody administration, blood was collected from the eye sockets under ether anesthesia, so as to obtain serum. Serum phosphate concentration was measured using P-Test Wako (trademark, Wako Pure Chemical Industries, Ltd., Japan).

The results are as shown below. By the continuous administration of the human FGF-23 recombinants using the osmotic mini pump, on day 3 after transplantation of the pump, a significant decrease in blood phosphorus concentration was recognized compared with the group of untreated mice to which the vehicle had been administered (FIG. 34, left). When the 2C5L antibody was administered to the human-FGF-23-recombinant-administered group (FGF-23/2C5L group), 24 hours later, the action to decrease serum phosphate concentration was significantly suppressed compared with the FGF-23/vehicle-administered group or that before antibody administration. The concentration was alleviated to the same degree as that of the serum phosphorus concentration of the untreated/vehicle-administered group (FIG. 34, right). According to the above results and results in Example 37, it became clear that the 2C5L antibody exhibited neutralization activity against the action of decreasing blood phosphate depending on the continuously administered human FGF-23 recombinants. On the other hand, in the group to which the 2C3B antibody had been administered, the serum phosphorus concentration 24 hours later was significantly higher than that of untreated/vehicle-administered group. This result may be due to the fact that the 2C3B antibody having strong binding ability with mouse FGF-23 exhibited neutralization activity not only with regard to the administered human FGF-23 recombinant, but also with regard to endogenous mouse FGF-23.

INDUSTRIAL APPLICABILITY

According to the present invention, antibodies against FGF-23 are provided. The antibodies of the present invention are useful in diagnosing diseases or pathological conditions accompanying accumulation or decreases of the FGF-23 protein by appropriately detecting and measuring FGF-23 in vivo. Furthermore, the antibodies of the present invention have activity of neutralizing the action of FGF-23, so as to be able to treat or alleviate diseases or pathological conditions resulting from excessive action of FGF-23 by suppressing the action of FGF-23.

All publications, patents, and patent applications cited herein are incorporated herein by reference in their entirety. It will be readily apparent to persons skilled in the art that certain changes and modifications may be made without departing from the technical idea or scope of the invention.

The present invention intends to encompass such changes and modifications.

The invention claimed is:

1. An antibody produced by a hybridoma whose accession number is FERM BP-7838 or FERM BP-7839.

2. A pharmaceutical composition, which comprises the antibody of claim 1 as an active ingredient.

3. A pharmaceutical composition comprising an antibody produced by a hybridoma whose accession number is FERM BP-7838 or FERM-7839, wherein the composition is effective against at least one disease selected from the group consisting of X-linked hypophosphatemic rickets, hypophosphatemia, and osteoporosis.

* * * * *

SEQUENCE LISTING

```
<160> NUMBER OF SEQ ID NOS: 36

<210> SEQ ID NO 1
<211> LENGTH: 251
<212> TYPE: PRT
<213> ORGANISM: Homo sapiens

<400> SEQUENCE: 1

Met Leu Gly Ala Arg Leu Arg Leu Trp Val Cys Ala Leu Cys Ser Val
 1               5                  10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 2
ccggaattca gccactcaga gcagggcacg                                         30
```

```
<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 3
ataagaatgc ggccgctcaa tggtgatggt gatgatggat gaacttggcg aa          52

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4
ataagaatgc ggccgctcag atgaacttgg cgaa                              34

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
ataccacggc agcacaccca gagcgccgag                                   30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6
ctcggcgctc tgggtgtgct gccgtggtat                                   30

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
atgaattcca ccatgttggg ggcccgcctc agg                               33

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 8
atgcggccgc ctaatgatga tgatgatgat ggatgaactt ggcgaaggg              49
```

```
<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Tyr Pro Asn Ala Ser Pro Leu Leu Gly Ser Ser Trp Gly Gly Leu Cys
 1               5                  10                  15

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

Arg Asn Ser Tyr His Leu Gln Ile His Lys Asn Gly His Val Asp Gly
 1               5                  10                  15

Ala Pro His Gln Cys
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Arg Phe Gln His Gln Thr Leu Glu Asn Gly Tyr Asp Val Tyr His Ser
 1               5                  10                  15

Pro Gln Tyr His Cys
            20

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Gly Met Asn Pro Pro Pro Tyr Ser Gln Phe Leu Ser Arg Arg Asn Glu
 1               5                  10                  15

Cys

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Cys Asn Thr Pro Ile Pro Arg Arg His Thr Arg
 1               5                  10

<210> SEQ ID NO 14
<211> LENGTH: 15
```

```
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Pro Arg Arg His Thr Arg Ser Ala Glu Asp Asp Ser Glu Arg Cys
 1               5                  10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Ser Ala Glu Asp Asp Ser Glu Arg Asp Pro Leu Asn Val Leu Lys Cys
 1               5                  10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

Leu Pro Ser Ala Glu Asp Asn Ser Pro Met Ala Ser Asp Cys
 1               5                  10

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Gly Gly Thr Gly Pro Glu Gly Cys Arg Pro Phe Ala Lys Phe Ile
 1               5                  10                  15

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

Gly Leu Ile His Leu Tyr Thr Ala Thr Ala Arg Asn Ser Cys
 1               5                  10

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 19

Thr Ile Tyr Ser Ala Leu Met Ile Arg Ser Glu Asp Ala Gly Phe Val
 1               5                  10                  15
```

```
Val Ile Thr Gly Val Met Ser Arg Arg Tyr Leu Cys
            20                  25

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 20

Met Asp Phe Arg Gly Asn Ile Phe Gly Ser His Tyr Phe Asp Pro Glu
  1               5                  10                  15

Asn Cys

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 21

Ser Pro Gln Tyr His Phe Leu Val Ser Leu Gly Arg Ala Lys Arg Ala
  1               5                  10                  15

Phe Leu Pro Gly Met Asn Cys
            20

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 22

Arg Asn Glu Ile Pro Leu Ile His Phe Asn Thr Pro Ile Cys
  1               5                  10

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

Ala Arg Met Thr Pro Ala Pro Ala Ser Cys Ser Gln Glu Leu Pro Ser
  1               5                  10                  15

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

Ser Asp Pro Leu Gly Val Val Arg Gly Gly Arg Val Asn Thr His Ala
  1               5                  10                  15

Gly Gly Thr Gly Pro Glu Gly Cys
```

-continued

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: synthetic DNA

<400> SEQUENCE: 25
attagccact cagtgctgtg caatg                                          25

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: synthetic DNA

<400> SEQUENCE: 26
gcagcctggc ctggggacct a                                              21

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: synthetic DNA

<400> SEQUENCE: 27
ggaattccac catgctaggg acctgcctta gactc                               35

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: synthetic DNA

<400> SEQUENCE: 28
atagtttagc ggccgcctag acgaacctgg gaaaggggcg aca                      43

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: synthetic DNA

<400> SEQUENCE: 29
ttcgcccacg gcaacacacg caaagcgccg aggac                               35

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: synthetic DNA

<400> SEQUENCE: 30
gtcctcggcg ctttgcgtgt gttgccgtgg gcgaa                               35

```
<210> SEQ ID NO 31
<211> LENGTH: 4
<212> TYPE: PRT
<213> ORGANISM: Homo sapiens

<400> SEQUENCE: 31

Arg His Thr Arg
  1

<210> SEQ ID NO 32
<211> LENGTH: 13
<212> TYPE: PRT
<213> ORGANISM: Mus musculus

<400> SEQUENCE: 32

Leu Ala Leu Pro Ala His His Asn Ala Thr Arg Leu Cys
  1               5                  10

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 33
cagacagaga catccgtgta g                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 34
ccacatggtc caggttcagt c                                              21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 35
accacagtcc atgccatcac                                                20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 36
tccaccaccc tgttgctgta                                                20
```